US009951328B2

(12) United States Patent
Biffi et al.

(10) Patent No.: US 9,951,328 B2
(45) Date of Patent: Apr. 24, 2018

(54) GENE VECTOR

(71) Applicants: Fondazione Telethon, Rome (IT); Ospedale San Raffaele S.r.l., Milan (IT)

(72) Inventors: Alessandra Biffi, Milan (IT); Bernhard Rudolf Gentner, Milan (IT); Luigi Naldini, Milan (IT)

(73) Assignees: Fondazione Telethon, Rome (IT); Ospedale San Raffaele S.r.l., Milan (IT)

( * ) Notice: Subject to any disclaimer, the term of this patent is extended or adjusted under 35 U.S.C. 154(b) by 0 days.

(21) Appl. No.: 15/693,112

(22) Filed: Aug. 31, 2017

(65) Prior Publication Data

US 2018/0044670 A1    Feb. 15, 2018

Related U.S. Application Data

(62) Division of application No. 13/266,381, filed as application No. PCT/IB2010/001166 on Apr. 30, 2010.

(60) Provisional application No. 61/174,124, filed on Apr. 30, 2009.

(51) Int. Cl.
| | |
|---|---|
| *C12N 15/63* | (2006.01) |
| *C12N 15/113* | (2010.01) |
| *C12N 15/86* | (2006.01) |
| *C12N 15/11* | (2006.01) |
| *A61K 48/00* | (2006.01) |

(52) U.S. Cl.
CPC ............ *C12N 15/111* (2013.01); *A61K 48/00* (2013.01); *C12N 2310/141* (2013.01); *C12N 2310/51* (2013.01); *C12N 2320/32* (2013.01); *C12N 2330/51* (2013.01); *C12N 2799/027* (2013.01)

(58) Field of Classification Search
None
See application file for complete search history.

(56) References Cited

U.S. PATENT DOCUMENTS

| | | |
|---|---|---|
| 2006/0134784 A1 | 6/2006 | Basch et al. |
| 2007/0196922 A1 | 8/2007 | Trono et al. |
| 2009/0180989 A1 | 7/2009 | Harvey |

FOREIGN PATENT DOCUMENTS

| | | |
|---|---|---|
| JP | 2008-545406 | 1/2007 |
| JP | 2008-545406 | 12/2008 |
| WO | WO-2005118806 A2 | 12/2005 |
| WO | WO-2006128245 A1 | 12/2006 |
| WO | WO-2007/000668 A2 | 1/2007 |
| WO | WO-2007081740 A2 | 7/2007 |
| WO | WO-2008008114 A2 | 1/2008 |
| WO | WO-2008073921 A2 | 6/2008 |
| WO | WO-2008154198 A1 | 12/2008 |

OTHER PUBLICATIONS

Mullokandov et al. High-Throughput Assessment of MicroRNA activity and Function Using microRNA Sensor and Decoy Libraries. Nature, 2012. 9(8):840-846.*
Gentner et al., "Stable knockdown of microRNA in vivo by lentiviral vectors." Nature Methods. (Jan. 2009); 6(1): pp. 63-66. (Published online Nov. 30, 2008).
Jin et al. "Differentiation of Two Types of Mobilized Peripheral Blood Stem Cells by MicroRNA and cDNA Expression Analysis," J. Translational Med., 6:39 (12 pp). (2008).
Papapetrou et al., "MicroRNA-Mediated Gene Regulation Effectively Restricts In Vivo Transgene Expression in Hematopoietic Stem Cell Progeny," Blood (2007), vol. 110, No. 11, part 1, p. 64a-65a, Abstract 193 (49th Annual meeting of the American Society of Hematology, Atlanta, Dec. 8-11, 2007).
Visigalli et al. "Development of an effective and safe hematopoietic stem cell gene therapy for globoid cell leukodystrophy: The unexpected issue of GALC toxicity," Molecular Genetics and Metabolism, 2008, 93, S14 -S46 (Abstract 103 on p. S41).
Abonour et al. Efficient retrovirus-mediated transfer of the multidrug resistance 1 gene into autologous human long-term rep opulating hematopoietic stem cells. Nat Med. 2000;6:652-658.
Biffi et al. Gene therapy of metachromatic leukodystrophy reverses neurological damage and deficits in mice. J Clin Invest. 2006;1 16:3070-3082.
Biffi et al. Correction of Metachromatic Leukodystrophy in the Mouse Model by Transplantation of Genetically Modified Hematopoietic Stem Cells. J Clin Invest. 2004;113:1118-1129.
Bjorgvinsdottir et al., Retroviral-Mediated Gene Transfer of gp91$^{phox}$ Into Bone Marrow Cells Rescues Defect in Host Defense Against Aspergillus fumigatus in Murine X-Linked Chronic Granulomatous Disease, Blood, vol. 89, No. 1, pp. 41-48 (1997).
Brady et al., Enzyme-replacement therapy for metabolic storage disorders. Lancet Neurol. 2004;3:752-756.
Brady, Enzyme replacement for lysosomal diseases. Annu Rev Med. 2006;57:283-296.
Brown et al. A microRNA -regulated lentiviral vector mediates stable correction of hemophilia B mice. Blood. 2007;110:4144-4152.
Brown et al., Endogenous microRNA regulation suppresses transgene expression in hematopoietic lineages and enables stable gene transfer. Nat Med. 2006;12:585-591.
Brown al., Endogenous microRNA can be broadly exploited to regulate transgene expression according to tissue, lieage and differentiation state, Nature Biotechnology, 2007, vol. 25, No. 12, p. 1457-1467.

(Continued)

*Primary Examiner* — Christopher M Babic
*Assistant Examiner* — Kimberly A Aron
(74) *Attorney, Agent, or Firm* — Marshall, Gerstein & Borun LLP

(57) ABSTRACT

A gene vector for use in gene therapy comprising at least one miRNA sequence target operably linked to a nucleotide sequence having a corresponding miRNA in a hematopoietic progenitor cell (HSPC) or hematopoietic stem cell (HSC) which prevents or reduces expression of the nucleotide sequence in a HSPC or HSC but not in a differentiated cell.

12 Claims, 41 Drawing Sheets

(56) References Cited

OTHER PUBLICATIONS

Brown, The Myelin Project Annual Meeting—2008, Novel Strategy for Gene Therapy of Globoid Cell Leukodystrophy.
Cartier et al., Hematopoietic stem cell gene therapy in Hurler syndrome, globoid cell leukodystrophy, metachromatic leukodystrophy and X-adrenoleukodystrophy, Current Opinion in Molecular Therapeutics Oct. 2008, vol. 10, No. 5, p. 471-478.
Catarinella et al. IFNα gene/cell therapy curbs colorectal cancer colonization of the liver by acting on the hepatic microenvironment, EMBO Molecular Medicine 8(2):155-170 (2016).
Chen et al., MicroRNAs modulate hematopoietic lineage differentiation. Science. 2004;303:83-86.
Chiriaco et al. Dual-regulated Lentiviral Vector for Gene Therapy of X-linked Chronic Granulomatosis, Molecular Therapy 22(8):1472-1483 (2014).
Declaration of Ilaria Visigalli under Rule 1.132 executed on Mar. 27, 2013.
Declaration of Kathryn Mitchell under Rule 1.132 executed on Apr. 3, 2013.
Declaration of Laura Tei under Rule 1.132 executed on Mar. 27, 2013.
Divaka et al., The emerging role of microRNAs in cardiac remodeling and heart failure. Circ Res. 2008;1 03:1072-1083.
Escobar et al. Genetic Engineering of Hematopoiesis for Targeted IFN-α Delivery Inhibits Breast Cancer Progression, Science Translational Medicine, 6(217):1-13 (2014).
Escolar et al., Transplantation of umbilical-cord blood in babies with infantile Krabbe's disease. NEJM 2005, 352; 20, 2069-2081.
European Examination Report dated Jun. 29, 2017, in corresponding EP Appl. No. 10723305.8 (6 pages).
Fazi et al. A minicircuitry comprised of microRNA-223 and transcription factors NFI-A and C/EBPalpha regulates human granulopoiesis. Cell. 2005;123:819-831.
Fish et al. MiR-126 regulates angiogenic signaling and vascular integrity. Dev Cell. 2008;15:272-284.
Garzon et al., MicroRNA fingerprints during human megakaryocytopoiesis, Proceedings of the National Academy of Sciences of the United States, Mar. 28, 2006, vol. 103, No. 13, p. 5078-5083 XP002465978.
Gentner et al. Stable knockdown of microRNA in vivo by lentiviral vectors. Nature Methods. 2009;6:63-66. Published online Nov. 30, 2008.
Gentner et al., Exploiting microRNA expression profiles for lineage- and differentiation state-specific transgene expression in hematopoietic, neutral and embryionic stem cells, Blood Cells, Molecules and Diseases, Feb. 12, 2008, vol. 40., No. 2, p267.
Gentner et al., Characterization of Hematopoietic Stem Cell Specific microRNA: From Physiologic Function to Gene Therapy Applications, Molecular Therapy, May 2009, vo.. 17, No. suppl. 1, p. S20.
Gritti et al. Multipotential stem cells from the adult mouse brain proliferate and self-renew in response to basic fibroblast growth factor. J Neurosci. 1996;16:1091-1100.
Hofling et al., Human CD34+ hematopoietic progenitor cell-directed lentiviral-mediated gene therapy in a xenotransplantation model of lysosomal storage disease. Mol Ther. 2004;9:856-865.
Houbaviy et al., Embryonic stem cell-specific MicroRNAs, Dev. Cell, 5(2):351-8 (2003).
International Search Report issued in PCT/IB2010/001166, dated Oct. 20, 2010.
Jin et al. Differentiation of Two Types of Mobilized Peripheral Blood Stem Cells by MicroRNA and cDNA Expression Analysis, J.Transl.Med. 2008, vol. 6(39): 1-12.
Johnnidis et al. Regulation of progenitor cell proliferation and granulocyte function by microRNA—223. Nature. 2008;451:1 125-1129.
Jordan, The leukemic stem cell, Best Practice & Research Clinical Haematology, vol. 20, No. 1, pp. 13-18 (2007).
Krutzfeldt et al. Silencing of microRNAs in vivo with 'antagomirs'. Nature. 2005;438:685-689.
Krutzfeldt et al., MicroRNAs: a new class of regulatory genes affecting metabolism. Cell Metab. 2006;4:9-12.
Kuehbacher et al., Role of Dicer and Drosha for endothelial microRNA expression and angiogenesis. Circ Res. 2007;1 01:59-68.
Lagos-Quintana et al., New microRNAs from mouse and human. RNA. 2003;9:1 75-179.
Landgraf et al. A mammalian microRNA expression atlas based on small RNA library sequencing. Cell. 200 7;1 29:1401-1414.
Lechman et al., High levels of MicroRNA-126 Bioactivity Specify the LSC Compartment in AML, Blood, Nov. 2008, vol. 112, No. 11, p. 193 (50th Annual Meeting of the American Society of Hematology, San Fransicos, Dec. 6, 2008).
Lin et al, Central nervous system-directed AAV2/5-mediated gene therapy synergizes with bone marrow transplantation in the murine model of globoid-cell leukodystrophy. Mol Ther 2007, vol. 15 No. 1, 44-52.
Malik et al., Retroviral-mediated gene expression in human myelomonocytic cells: a comparison of hematopoietic cell promoters to viral promoters, Blood, 86(8):2993-3005 (1995).
Mansfield et al., MicroRNA-responsive 'sensor' transgenes uncover Hox-like and other developmentally regulated patterns of vertebrate microRNA expression, Nat. Genet., 36(10)1079-83 (2004).
McDermott et al., Comparison of human cord blood engraftment between immunocompromised mouse strains, Blood, vol. 116, No. 2, pp. 193-200 (Jul. 15, 2010).
Mechtcheriakova et al. Sphingosine 1-phosp hate phosphatase 2 is induced during inflammatory responses. Cell Signal. 2007;19:748-760.
Meng et al., GALC transduction leads to morphological improvement of the twitcher oligodendrocytes in vivo. Mol Genet Metab. Apr. 2005;84(4):332-43. Epub Jan. 24, 2005.
Papapetrou et al., MicroRNA-mediated gene regulation effectively restricts in vivo transgene expression in hematopoietic stem cell progeny, Blood, 2007, vol. 110, No. 11, part 1, p. 64a-65a, (49th Annual meeting of the Merican-Society of Hematology, Atlanta, Dec. 8-11, 2007).
Papapetrou et al. Harnessing Endogenous miR-181a to Segregate Transgenic Antigen Receptor Expression in developing Versus Post-Thymic T Cells in Murine Hematopoietic Chimeras, J. Clinical Investigation, 119(1): 157-168 (Jan. 2009).
Pellegatta et al, The therapeutic potential of neural stem/progenitor cells in murine globoid cell leukodystrophy is conditioned by macrophage/microglia activation Neurobiol Dis 2006, 21, 314-323.
Rohrbach et al., Treatment of lysosomal storage disorders : progress with enzyme replacement therapy. Drugs. 2007;67:2697-271 6.
Rosa et al. The interplay between the master transcription factor PU.1 and miR-424 regulates human monocyte/macrophage differentiation. Proc Natl Acad Sci U S A. 2007;1 04:19849-19854.
Ryser et al., Gene therapy for chronic granulomatous disease, Expert Opinion in Biological Therapy, Dec. 2007, vol. 7, No. 12, p. 1799-1809.
Sadelain et al., Progress toward the genetic treatment of the beta-thalassemias. Ann N Y Acad Sci. 2005;1054:78-91.
Sadelain, Recent advances in globin gene transfer for the treatment of beta-thalassemia and sickle cell anemia. Curr Opin Hematol 2006;13:142-148.
Sands et al. Murine mucopolysaccharidosis type VII: long term therapeutic effects of enzyme replacement and enzyme replacement followed by bone marrow transplantation. J Clin Invest. 1997;99:1596-1605.
Sano et al., Chemokine-induced recruitment of genetically modified bone marrow cells into the CNS of GM1-gangliosidosis mice corrects neuronal pathology. Blood. 2005;1 06:2259-22 68.
Shen et al., MicroRNA-126 regulates HOXA9 by binding to the homeobox. Mol Cell Biol. Jul. 2008;28(14):4609-19. Epub May 12, 2008.
Taylor et al, Intrinsic resistance of neural stem cells to toxic metabolites may make them well suited for cell non-autonomous disorders: evidence from a mouse model of Krabbe leukodystrophy. J Neurochem 2006, 97, 1585-1599.

(56) References Cited

OTHER PUBLICATIONS

Torchiana et al.,Retroviral-mediated transfer of the galactocerebrosidase gene in neural progenitor cells. Neuroreport. Dec. 1, 1998;9(17):3823-7.

Visigalli et al. Development of an effective and safe hematopoietic stem cell gene therapy for globoid cell leukodystrophy: The unexpected issue of GALC toxicity Program and Abstracts for the Lysosomal Disease Network's World Symposium 2008 Feb. 13-15, 2008, Molecular Genetics and Metabolism vol. 93, Issue 2, Feb. 2008, p. S41, 103 Available online Jan. 14, 2008.

Visigalli et al. GALC Over-Expression Toxicity in Hematopoietic Stem Cells Is Rescued by microRNA Regulation: New Perspectives for Gene Therapy of Globoid Leukodystrophy. Molecular Therapy vol. 16, Supplement 1, May 2008.

Visigalli, Ex Vivo Gene Therapy Approaches for the Treatment of Globoid Cell Leukodystrophy, Ph.D. thesis in fulfillment of the requirements of the Open University for the degree of Doctor of Philosophy in Molecular and Cellular Biology (2009).

Wang et al. The endothelial-specific microRNA miR-126 governs vascular integrity and angiogenesis. Dev Cell. 2008;15:261-271.

Weil et al. Genetic correction of p67phox deficient chronic granulomatous disease using peripheral blood progenitor cells as a target for ret rovirus mediated gene transfer. Blood. 1997;89:1754-1761.

Wing et al, Enzyme replacement therapy results in substantial improvements in early clinical phenotype in a mouse model of globoid cell leukodystrophy FASEB J. Sep. 2005;19(11):1549-51. Epub Jun. 29, 2005.

Woods et al., Gene therapy: therapeutic gene causing lymphoma. Nature. 2006;440:1123.

Xiao et al., MicroRNA control in the immune system: basic principles. Cell. 2009;136:26-36.

Yeager et al. Prolonged survival and remyelination after hematopoietic cell transplantation in the twitcher mouse. Science. Sep. 7, 1984;225(4666):1052-4.

Zhang et al., The cell growth suppressor, mir-126, targets IRS-1, Biochemical and Biophysical Research Communications, vol. 377, pp. 136-140 (2008).

Notice of Reasons for Rejection (with English translation), Japanese patent application No. 2012-507847, dated Nov. 29, 2016.

Gentner et al., Identification of hematopoietic stem cell-specific miRNAs enables gene therapy of globoid cell leukodystrophy, Sci. Transl. Med., 2(58):58ra84 (2010).

Kuchenbauer et al., Comprehensive Profiling of Micrornas in Murine Hematopoietic Stem Cells and Lineages Using a Microfluidics Approach, Blood, 112(11):2468 (2008) [abstract only].

Liao et al., MicroRNAs play a role in the development of human hematopoietic stem cells, J. Cell Bochem., 104(3):805-17 (2008).

\* cited by examiner

| Transplanted cells | Host | VCN (20 days) | VCN (≥120 days) |
|---|---|---|---|
| (°)GALC -/- HSPC (§) | +/- | 0.01±0 | - |
| GALC -/- HSPC (§) | -/- | 0.02±0 | - |
| GALC -/- HSPC (§) | -/- | 2.3±1 | 2±0.5 |

Table 2 c d

GENE VECTOR

FIELD OF THE INVENTION

The present invention relates to gene vectors for use in gene transfer and therapy applications, and to methods of producing them, and uses thereof.

BACKGROUND TO THE INVENTION

Hematopoietic cell transplantation (HCT) from normal donors is a curative therapy for several inherited and acquired disorders. However, the transplant is limited by the poor availability of matched donors and the mortality associated with the allogenic procedure (mostly related to graft versus host disease—GvHD). HCT has a very low efficacy in some disorders such as lysosomal storage diseases (LSD). In order to improve the safety and efficacy of allogeneic transplants and to identify alternative protocols for patients lacking a matched donor, a gene therapy approach based on the transplantation of gene corrected, autologous hematopoietic stem cell (HSC) is required.

As an alternative to allogeneic HCT an inherited genetic defect can be corrected in the patient's own hematopoietic cells by gene therapy. However, delivery of a functional copy of the relevant gene into all affected cells of the body is difficult. The concept of stem cell gene therapy is based on the genetic modification of a relatively small number of stem cells, which remain long-term in the body by undergoing self-renewal divisions, and generate huge numbers of genetically corrected progeny, thus ensuring a continuous supply of corrected cells for the rest of the patient's lifetime. Hematopoietic stem cells (HSC) constitute an excellent target population for gene therapy, since they can be easily and safely obtained from bone marrow (BM) or mobilized peripheral blood. The isolated HSC can be genetically modified and returned to the patient as an autologous transplant. Long-term benefit requires the transplantation of a sufficiently high number of gene-modified HSC, which can repopulate the conditioned BM, giving rise to corrected blood cells of all hematopoietic lineages. Autologous allogeneic HSC make the transplant procedure available to all patients and avoids immunological compatibility problems leading to GvHD. In addition, some diseases like primary immunodefficiencies require the correction of a fraction of HSC and their progeny. The intensity of the conditioning regimen (so-called "non-myeloablative" or "mini" conditioning regimen) is reduced which results in better tolerability and fewer side effects for the patient. A reduced conditioning regimen is less compatible with a standard allogeneic transplant, because mixed donor chimerism is usually unstable in the allogeneic setting due to immunological antagonism with host-derived immune cells.

Efficient long-term gene modification of HSC and their progeny requires a technology which permits stable integration of the corrective DNA into the genome, without affecting HSC function. The most efficient delivery systems are viral vectors.

For example, gene transfer and expression in hematopoietic progenitor cell (HSPC) of the lysosomal enzyme galactocerebrosidase (lacking in Globoid Leukodystrophy—GLD—or Krabbe disease) causes apoptosis and functional impairment of the transduced cells, preventing the development of HSPC based gene therapy approaches for treating the disorder (see below). Thus, future expression cassettes used for gene therapy should resemble physiologic expression patterns and avoid ectopic and/or non-physiologic transgene expression, which can result in toxicity, elimination or even malignant transformation of the transduced cells. This is particularly important for stem cells, the key target cell type guaranteeing long-term efficacy of gene therapy, whose biology must not be disturbed by the genetic intervention.

To summarize, current hematopoietic gene therapy strategies require transduction of HSC to guarantee long-term correction of the hematopoietic system, but would significantly benefit from regulated transgene expression cassettes that do not ectopically express the transgene product in HSC, but "switch on" only in the differentiated progeny that are the target of the genetic disease, e.g. lymphocytes in SCID, granulocytes in CGD and monocytes/macrophages in GLD.

One way to achieve this is the use of lineage-specific transcriptional control elements, e.g. the endogenous promoter of the locus, to drive expression of the therapeutic gene in the vector. However, promoters are often spread over a long range of DNA and poorly characterized, and can thus not be easily reconstituted in their entirety in a vector construct. Furthermore, expression levels from tissue-specific promoters reconstituted in gene-transfer vectors are often not sufficient to achieve phenotypic correction, most likely because of imperfect reconstitution and/or detrimental influence of the chromatin at the semi-random vector integration site. Thus, additional strategies to regulate a transgene are direly needed.

STATEMENTS OF THE INVENTION

According to one aspect of the present invention there is provided a gene vector for use in gene therapy comprising at least one miRNA sequence target operably linked to a nucleotide sequence having a corresponding miRNA in a hematopoietic progenitor cell (HSPC) which prevents or reduces expression of the nucleotide sequence in a HSPC but not in a differentiated cell.

According to another aspect of the present invention there is provided a gene vector for use in gene therapy comprising at least one miRNA sequence target operably linked to a nucleotide sequence having a corresponding miRNA in a hematopoietic stem cell (HSC) which prevents or reduces expression of the nucleotide sequence in a HSC but not in a differentiated cell.

In other words, the present invention provides a gene vector suitable for use in hematopoietic gene therapy comprising at least one miRNA sequence target for a miRNA which is present in an effective amount in a hematopoietic progenitor cell or hematopoietic stem cell and optionally a transgene. By effective amount we mean that the concentration of the endogenous miRNA is sufficient to reduce or prevent expression of a transgene which is operably linked to the corresponding miRNA target sequence. Thus the present invention employs the use of miRNA which is strongly expressed in cells, such as HSPC and HSC but not in differentiated progeny of e.g. the myeloid and lymphoid lineage, preventing or reducing expression of a potentially toxic transgene in sensitive stem cell populations, whilst maintain expression and therapeutic efficacy in the diseased progeny.

The miRNA is "operably linked" to the transgene. The term "operably linked" means that the components described are in a relationship permitting them to function in their intended manner.

A stem cell is able to differentiate into many cell types. A cell that is able to differentiate into all cell types is known as totipotent. In mammals, only the zygote and early embryonic cells are totipotent. Stem cells are cells found in most, if not all, multi-cellular organisms. They are characterized by the ability to renew themselves through mitotic cell division and differentiating into a diverse range of specialized cell types. The two broad types of mammalian stem cells are: embryonic stem cells that are isolated from the inner cell mass of blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues.

Hematopoietic stem cells (HSCs) are multipotent stem cells that give rise to all the blood cell types including myeloid (monocytes and macrophages, neutrophils, basophils, eosinophils, erythrocytes, megakaryocytes/platelets, dendritic cells), and lymphoid lineages (T-cells, B-cells, NK-cells).

Progenitor cells have a capacity to differentiate into a specific type of cell. In contrast to stem cells, however, they are already far more specific: they are pushed to differentiate into their "target" cell. The most important difference between stem cells and progenitor cells is that stem cells can replicate indefinitely, whereas progenitor cells can only divide a limited number of times. HSPC can be rigorously distinguished from HSC only by functional in vivo assay, i.e. transplantation and demonstration that they can give rise to all blood lineages over prolonged time periods. The detection of cell surface markers such as c-Kit (CD117), Sca-1 and the absence/low-expression of a panel of lineage markers, combined with a recently described set of molecules belonging to the SLAM receptor family (CD150 and CD48), can enrich for HSC and HSPC subpopulations, reaching a purity of 50% when assayed against standard functional assays (Kiel et al).

A differentiated cell is a cell which has become more specialized in comparison to the stem cell or progenitor cell. Differentiation occurs during the development of a multi-cellular organism as the organism changes from a single zygote to a complex system of tissues and cell types. Differentiation is also a common process in adults: adult stem cells divide and create fully-differentiated daughter cells during tissue repair and during normal cell turnover. Differentiation dramatically changes a cell's size, shape, membrane potential, metabolic activity, and responsiveness to signals. These changes are largely due to highly-controlled modifications in gene expression. In other words a differentiated cell is a cell which which has specific structures and performs certain functions due to a developmental process which involves the activation and deactivation of specific genes. Here, a differentiated cell includes differentiated cells of the hematopoetic lineage such as monocytes, macrophages, neutrophils, basophils, eosinophils, erythrocytes, megakaryocytes/platelets, dendritic cells, T-cells, B-cells and NK-cells. For example, differentiated cells of the hematopoetic lineage can be distinguished from HSC and HSPC by detection of cell surface molecules which are not or less expressed on undifferentiated cells. Examples of suitable lineage markers such as CD11b, Gr1, CD19, Ter119 and CD3.

According to another aspect of the present invention there is provided a gene vector for use in gene therapy comprising at least one miRNA sequence target corresponding to a miRNA selected from the group comprising mir-130a, mir-126 and mir-223 operably linked to a nucleotide sequence.

miR-126 target blocks expression most effectively in the more primitive HSPC and (in humans) in the erythroid lineage. miR-126 would be particularly suitable for gene therapy applications relying on robust transgene expression in the myeloid and lymphoid lineage.

miR-130a target blocks expression most effectively in the more primitive HSPC (similar to miR-126), miR-130a would be most particularly suitable for gene therapy applications relying on robust transgene expression in the myeloid, lymphoid and erythroid lineage.

miR-126 may be stronger than miR-130a in human CD34 cells, but may have also non-specific activity in the differentiated progeny. A combination target comprising miR-130aT sequences (preferably 2-4 copies) and "half" miR-126T (preferably 2 copies) maximizes the operating window determined by the ratio of repression in HSPC and expression in the myeloid progeny. Furthermore, when using the combination target, transgene downregulation in HSPC is assured by 2 independent miRNAs, and the risk of interfering with endogenous miRNA regulation is reduced, thus increasing safety and efficacy of the target sequence. miR-223 target blocks expression most effectively in myeloid committed progenitors and at least partially in the more primitive HSPC. At variance to miR-126 and miR-130a, miR-223 target fully and strongly blocks expression in differentiated myeloid cells including granulocytes, monocytes, macrophages, myeloid dentritic cells. miR-223 target would be particularly suitable for gene therapy applications relying on robust transgene expression in the lymphoid or erythroid lineage. miR-223 target may block expression also very effectively in human HSC.

Preferably, the miRNA sequence targets correspond to mir-130a and mir-126.

In one embodiment the gene vector comprises the nucleotide sequence which controls the expression of the vector. In other words, the endogenous microRNA prevents expression or proliferation of the virus in certain cell types (HSC and HSPC) but allows the expression or proliferation in other cell types. For example, mir-126, mir-130 and mir-223 prevent expression of a gene vector or oncloytic virus in a hematopoietic stem cell or progenitor cell.

In one embodiment the gene vector comprises the nucleotide sequence which is a transgene.

In another embodiment the gene transfer vector is in the form of a non-viral gene transfer vector. In this embodiment, the gene transfer vector may comprise, or be in the form of, an expression vector or plasmid which comprises the miRNA target sequence operationally linked to a nucleotide sequence.

Expression vectors as described herein comprise regions of nucleic acid containing sequences capable of being transcribed. Thus, sequences encoding mRNA, tRNA and rRNA are included within this definition.

The gene vector or gene transfer vector of the present invention may be used to deliver a transgene to a site or cell of interest. The vector of the present invention may be delivered to a target site by a viral or non-viral vector.

A vector is a tool that allows or facilitates the transfer of an entity from one environment to another. By way of example, some vectors used in recombinant DNA techniques allow entities, such as a segment of DNA (such as a heterologous DNA segment, such as a heterologous cDNA segment), to be transferred into a target cell. Optionally, once within the target cell, the vector may then serve to maintain the heterologous DNA within the cell or may act as a unit of DNA replication. Examples of vectors used in recombinant DNA techniques include plasmids, chromosomes, artificial chromosomes or viruses.

Non-viral delivery systems include but are not limited to DNA transfection methods. Here, transfection includes a process using a non-viral vector to deliver a gene to a target mammalian cell.

Typical transfection methods include electroporation, DNA biolistics, lipid-mediated transfection, compacted DNA-mediated transfection, liposomes, immunoliposomes, lipofectin, cationic agent-mediated, cationic facial amphiphiles (CFAs) (Nature Biotechnology 1996 14; 556), and combinations thereof.

In one embodiment the gene vector is a viral vector.

Viral delivery systems include but are not limited to adenovirus vector, an adeno-associated viral (AAV) vector, a herpes viral vector, retroviral vector, lentiviral vector, baculoviral vector. Other examples of vectors include ex vivo delivery systems, which include but are not limited to DNA transfection methods such as electroporation, DNA biolistics, lipid-mediated transfection, compacted DNA-mediated transfection.

The term "vector particle" refers to the packaged retroviral vector, that is preferably capable of binding to and entering target cells. The components of the particle, as already discussed for the vector, may be modified with respect to the wild type retrovirus. For example, the Env proteins in the proteinaceous coat of the particle may be genetically modified in order to alter their targeting specificity or achieve some other desired function.

Preferably, the viral vector preferentially transduces a certain cell type or cell types.

More preferably, the viral vector is a targeted vector, that is it has a tissue tropism which is altered compared to the native virus, so that the vector is targeted to particular cells.

In a preferred embodiment the gene vector is derivable from a lentivirus.

In one embodiment the gene vector comprises a tissue specific promoter. Preferably, the tissue specific promoter is selected from the group comprising CD11b and c-Fes, and promoters derived from the cytochrome b-245 heavy chain (CYBB, gp91 phox) locus and TEK (Tie2). TEK (Tie2) promoter could be combined with the miR-126 target sequence, this combination would allow specific transgene expression in a subset of tumor-infiltrating myeloid cells.

In one embodiment the gene vector comprises a transgene which codes for an enzyme. Preferably, the enzyme is selected from the group lysosomal enzyme galactocerebrosidase and gp91 phox. According to the present invention can be used to deliver immunomodulatory molecules, such as interferon-alpha. Preferably these vectors deliver the immunomodulatory molecules into tumor cells upon bone marrow transplantation. Preferably these vectors contain the Tie2 promoter plus, a miR-126T sequence.

Importantly, the Tie2 promoter possesses activity in hematopoietic stem cells, and immunomodulatory molecules such as interferon-alpha are known to be toxic to HSC. Thus, the use of HSC-specific miRTs—as described in this patent application—becomes obligatory rather than an option in order to specifically deliver bioactive molecules by Tie2 expressing, tumor infiltrating macrophages without interfering with HSC function. Given that the Tie2 promoter is weaker in HSC than the PGK promoter which has been used throuhout our studies, we expect that 126T/130aT sequences fully prevent toxicity of transgenes expressed from the Tie2 promoter in HSC.

According to another aspect of the invention there is provided a set of DNA constructs for producing a viral vector particle comprising a DNA construct encoding a packagable viral vector genome comprising at least one miRNA sequence target according to the present invention, and optionally a transgene. By packagable vector genome we mean that the vector genome is in an environment where it can be packaged into a viral vector particle. This generally requires the present of Gag-Pol and Env.

According to another aspect of the invention there is provided a process for preparing a viral vector particle comprising introducing the set of DNA constructs of the present invention into a host cell, and obtaining the viral vector particle.

In one embodiment the host cell comprises the corresponding miRNA.

According to another aspect of the invention there is provided a viral vector particle produced by the process of the present invention.

According to another aspect of the invention there is provided a pharmaceutical composition comprising the gene vector or particle according to the present invention together with a pharmaceutically acceptable diluent, excipient or carrier.

According to another aspect of the invention there is provided a cell infected or transduced with the gene vector or particle according to the present invention. The cell may be transduced or infected in an in vivo or in vitro scenario. The cell may be derived from or form part of an animal, preferably a mammal, such as a human or mouse. Thus it will be appreciated that the present invention is useful in providing transgenic animals e.g., for use as disease models. In one embodiment, the mammal is a non-human mammal.

In one embodiment the cell is a hematopoietic stem cell or a hematopoietic progenitor cell.

According to another aspect of the invention there is provided a combination of at least two different miRNAs sequence targets corresponding to miRNAs selected from the group comprising mir-130a, mir-126 and mir-223.

In one embodiment the miRNA sequence targets are for simultaneous, separate or sequential use.

According to another aspect of the invention there is provided a gene vector according to the present invention, a particle according to the present invention, a pharmaceutical composition according to the present invention, a cell according to claims the present invention or a combination according to the present invention for preventing or reducing expression of a transgene in a hematopoietic stem cell or a hematopoietic progenitor cell.

According to another aspect of the invention there is provided a gene vector according to the present invention, a particle according to the present invention, a pharmaceutical composition according to the present invention, a cell according to claims the present invention or a combination according to the present invention for treating a disease selected from Globoid Cell Leukodystrophy, Chronic Granulomatous Disease and Severe Combined Immunodeficiency (SCID).

According to another aspect of the invention there is provided a gene vector according to the present invention, a particle according to the present invention, a pharmaceutical composition according to the present invention, a cell according to claims the present invention or a combination according to the present invention for increasing the chances of survival of a hematopoietic stem cell or a hematopoietic progenitor cell in relation to gene therapy.

The chances of survival of an HSC or HSPC can be increased by specifically detargeting expression of genes from these cells. In particular, the detargeting of expression of transgenes which are toxic for HSC or HSPC could be beneficial for the survival of these cells. Also, detargeting of expression of transgenes which could cause an unwanted immune reaction in the host could result in an increased chance of survival of the cell.

According to another aspect of the invention there is provided a gene vector according to the present invention, a particle according to the present invention, a pharmaceutical composition according to the present invention, a cell according to claims the present invention or a combination according to the present invention for increasing the safety and/or efficacy of gene therapy.

An increase in safety of gene therapy includes the prevention or reduction of unwanted expression of transgenes or expression of the vector in certain cell types such as HSC and HSPC. Detargeting of expression of a transgene or vector from specific cell types can reduce unwanted reaction or side effects which may accompany gene therapy. An increase in efficacy of gene therapy includes that transgenes are more effectively expressed in the desired cell types such as differentiated hematopoietic cells, because these cells are more effectively generated from gene-modified undifferentiated cells which are protected from transgene toxicity and unwanted immune reactions by the microRNA target sequence. In particular, gene therapy involving the transplantation of HSC or HSPC can be safer and more efficient if expression of the transgene can be avoided until the cells have differentiated.

According to another aspect of the invention there is provided a gene vector according to the present invention, a particle according to the present invention, a pharmaceutical composition according to the present invention, a cell according to claims the present invention or a combination according to the present invention for preventing apoptosis of a hematopoietic stem cell or a hematopoietic progenitor cell, whereby the apoptosis is caused by expression of the transgene.

According to another aspect of the invention there is provided a gene vector according to the present invention, a particle according to the present invention, a pharmaceutical composition according to the present invention, a cell according to claims the present invention or a combination according to the present invention for monitoring a stage of differentiation of a hematopoietic stem cell or a hematopoietic progenitor cell.

The presence of mir-126, mir-223 and mir-130a is indicative of an HSC or HSPC. More specifically mir-126 is indicative of primitive HSPC and, in humans, also of cells of the erythroid lineage. Mir-130a is indicative of the more primitive HSPC. Mir-223 is indicative of myeloid committed progenitor cells and the more primitive HSPC. Mir-223 is also indicative of differentiated myeloid cells including granulocytes, monocytes, marcophages and myeloid dentritic cells.

In one embodiment the gene vector is for use in hematopoietic cell therapy. Hematopoietic cell therapy includes hematopoetic stem cell transplantation.

According to another aspect of the invention there is provided a miRNA sequence target corresponding to a miRNA selected from the group of mir-130a, mir-126 and mir-223 for use in gene therapy.

According to another aspect of the invention there is provided a method of determining the differentiation stage of a hematopoietic stem cell or a hematopoietic progenitor cell, comprising determining the level of expression of a miRNA in the cell, wherein the miRNA corresponds to a miRNA target sequence operably linked to a nucleotides sequences, wherein the miRNA prevents or reduces expression of the nucleotide sequence in a hematopoietic progenitor cell (HSPC) or a hematopoietic stem cell (HSC) but not in a differentiated cell. For example, expression of mir-130a and mir-126 indicates that the cell is a HSPC or HSC, while expression of miR-223 indicates affiliation to the myeloid lineage, i.e. granulocytes and monocytes, including their precursors and derivatives.

According to another aspect of the invention there is provided a method of determining the differentiation stage of a hematopoietic stem cell or a hematopoietic progenitor cell, comprising determining the level of expression of at least two different miRNAs in the cell, wherein the miRNAs correspond to miRNA target sequences operably linked to nucleotide sequences, wherein the miRNAs prevent or reduce expression of the nucleotide sequences in a hematopoietic progenitor cell (HSPC) or a hematopoietic stem cell (HSC) but not in a differentiated cell and comparing the expression level of the different miRNAs. Moreover, the expression of two microRNAs can be assayed contemporaneously and independently from each other using a bidirectional vector which expresses two marker genes, each one containing a different microRNA target sequence. For example, the different micro RNAs could be linked to different marker such as fluorescent markers. Different colours would indicate different mixtures of expression of the microRNAs which represent different differentiations stages (e.g. green marker+miR–126T, red marker+miR–223T. If cells are red or black:-->HSPC; if cells are yellow:-->lymphocytes; if cells are green: differentiated myeloid lineage cells.)

According to another aspect of the invention there is provided a method of determining the differentiation stage of a hematopoietic stem cell or a hematopoietic progenitor cell, comprising determining the expression level of a transgene in said hematopoietic stem cell or said hematopoietic progenitor cell, wherein the transgene is operably linked to a miRNA sequence target, whereby the corresponding miRNA prevents or reduces expression of the transgene in a hematopoietic progenitor cell (HSPC) or a hematopoietic stem cell (HSC) but not in a differentiated cell.

Furthermore, reporter vectors for miRNAs selected from the group containing miR-126, miR-130a and miR-223 might be applied to identify hematopoietic stem cells and/or their immediate precursors in culture systems aimed at obtaining hematopoietic lineage cells from induced pluripotent cells (iPS) or embryonic stem cells (ES)

In one embodiment of the present invention the miRNAs used in the methods of the present invention comprise the miRNA selected from the group comprising mir-130a, mir-126 and mir-223.

Some Further Key Advantages of the Invention

The invention teaches how gene vectors suitable for gene therapy can be designed to be regulated by miRNAs endogenous for HSC and HSPC for controlling transgene expression to achieve specific expression profiles of the vector. The invention provides broad application of these vectors as they will help to prevent transgene toxicity in HSC and HSPC and thus facilitate the development of gene therapy strategies for the treatment of various diseases. The vectors are particularly suitable for gene therapies which involve the expression of a transgene which is toxic for HSC or HSPC.

The inventors provide a novel method to profile the activity of selected miRNAs across multiple hematopoietic cell subsets including rare HSPC populations, thus adding a new dimension to conventional miRNA expression profiling approaches, which are broad but limited to a previously purified bulk population. This method is based on the transduction of HSPC with lentiviral miRNA reporter vectors, which serve as a live genetic indicator for the activity of a miRNA, easily quantifiable at the single cell level and in multiple cell populations in parallel by flow cytometry. Using this approach, the inventors identified two miRNAs that are highly functional in mouse and human HSPC, including subsets enriched for the most primitive stem cells. Upon differentiation, one miRNA is rapidly down-regulated at the early progenitor cell level, while the other one is further induced during granulo- and monopoiesis, but sharply down-regulated in lymphocytes and during megakaryocyte/erythrocyte differentiation.

Furthermore, the inventors applied one of the two miRNAs highly expressed in HSPC to overcome a major issue preventing efficacious treatment of globoid leukodystrophy (GLD)(a lysosomal storage disorder due to defective activity of the lysosomal enzyme galactocerebrosidase—GALC) in the murine model by lentiviral vector-based hematopoietic stem cell gene therapy. In contrast to other lysosomal enzymes, GALC gene transfer and expression in HSPC causes apoptosis and functional impairment of the transduced cells due to an imbalance of the intracellular content in bioactive sphingolipids consequent to enzyme expression. Differentiated cells of the myeloid and lymphoid lineages are not affected by GALC expression, suggesting a unique sensitivity of HSPC to enzyme toxicity. The miRNA-responsive sequences used for the reporter vectors allowed regulating the expression profile of the therapeutically relevant GALC transgene, de-targeting transgene expression from cells where the cognate miRNA is expressed (HSPC), while permitting full therapeutic expression in the differentiated progeny that is not affected by the GALC-expression toxicity. The HSPC transduced with the miRNA-regulated GALC lentiviral vectors were protected from enzyme toxicity and retained their function both in vitro and in vivo. Preliminary results indicate therapeutic efficacy of this approach in correcting disease manifestations in the mouse model.

Preferably, the following miRNA target sequences are employed to achieve regulated transgene expression in the human hematopoietic system: gene therapy applications which require expression in the myeloid lineage (e.g. chronic granulomatous disease, lysosomal storage disorders such as Krabbe disease, metachromatic leukodystrophy, adrenoleukodystrophy, etc): 126T/130aT (2+2 target sequences)—optimized for maximal repression in HSPC; 126T (2 target sequences)—optimized for minimal background activity in the myeloid progeny.

Gene therapy applications which require expression in the erythroid lineage (e.g. thalassemia, glucose-6-phosphate dehydrogenase deficiency, sickle cell disease): 130aT (4 target sequences), or 223T (2 or 4 target sequences). The latter target might exhibit some activity (<5x) in more primitive BFU-E and CFU-E.

Gene therapy applications which require expression in the lymphoid lineage (e.g. RAG1/RAG2 deficiency, BTK deficiency, X-SCID, ADA-SCID): 223T (2 or 4 target sequences), possibly in combination with 126T/130aT (2+2 target sequences) or 126T (2 target sequences).

Vectors, such as viral including lentiviral vectors, for transgene expression for gene transfer and therapy can be engineered with miRNAs target sequence in order to be recognized by endogenous miRNAs cell endogenous to HSC and HSPC, thus regulating transgene expression in a subset of cells. Moreover, combinations of miRNA target sequences can be used to obtain vectors with highly specific cell expression patterns.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

DESCRIPTION OF THE FIGURES

The present invention will be described further, by way of example only, with reference to preferred embodiments thereof as illustrated in the accompanying drawings, in which.

The indicated LVs (A) were used to transduce murine and human HSPC obtained from Galc−/− (—/—) and wild type (+/+) mice, as well as cord blood (CB) and bone marrow (BM) from normal donors, respectively. GALC activity (B) and vector copy number (VCN) (C) were measured in the in vitro culture progeny of the transduced murine (top panels) and human (bottom panels) HSPC (pooled data from −/− and +/+ HSPC are shown in top panel C). (D) The number (#) of colonies retrieved from clonogenic assays (CFC) performed at the end of transduction with the indicated LV on murine −/− (top panel) and human (bottom panel) HSPC is reported. (E) TUNEL assay was performed two days after transduction with the indicated LV on murine −/− HSPC (top panel) and CD34+ cells from normal donors' CB and BM (bottom panel). The frequency of apoptosis among transduced cells was assessed (% TUNEL+ cells). Each dot represents an individual sample (B-E). In E, ≥8 fields and ≥100 cells were counted for each sample. *:p<0.05: p<0.01; *: p<0.001. (F) Representative TUNEL staining on GFP LV- and GALC LV-transduced HSPC is shown.

Magnification 100×.

Figure 5:
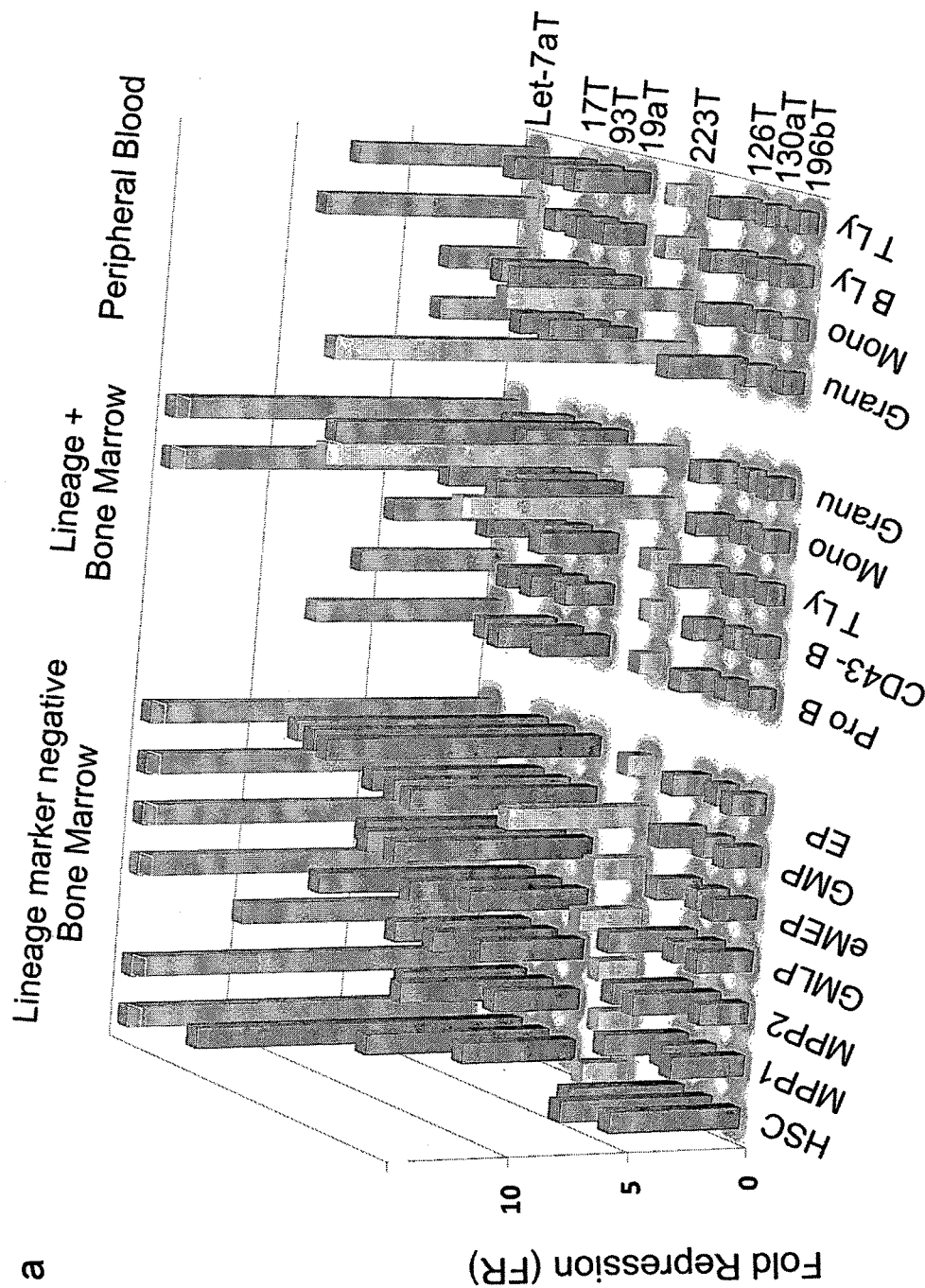
FIG. 5: (a) Hematopoietic activity of 8 miRNAs as measured by the mean fold repression (FR) of indicated reporter BdLVs in multiple cell populations isolated from transplanted mice. Lineage$^-$ BM subsets: as described in FIG. 4; Lineage$^+$ BM subsets: Pro B: CD19$^+$CD43$^+$; CD43$^-$ B: CD19$^+$CD43$^-$; T Ly: CD3$^+$; Mono: CD11b$^+$CD48$^+$; Granu: CD11b$^+$CD48$^{lo}$; Peripheral blood: Granu: CD11b$^+$ side scatter$^{hi}$; Mono: CD11b$^+$ side scatter$^{lo}$; B Ly: CD19$^+$; T L$_y$: CD3. (b) A combination target sequence containing 4 copies of miR-130aT and 2 copies of miR-126T (130a/126T; n=4 mice) was compared to either 4 copies of miR-126T (126T; n=10 mice) or 4 copies of miR-130aT (130aT; n=4 mice). The bars show the fold repression±sem obtained by these miRT sequences in Lineage marker negative bone marrow populations (legend as in FIG. 4) and in peripheral blood leukocytes. Note that the 130a/126T achieves a better repression in HSC than 126T alone, while background repression in PB leukocytes is reduced.
Figure 5:
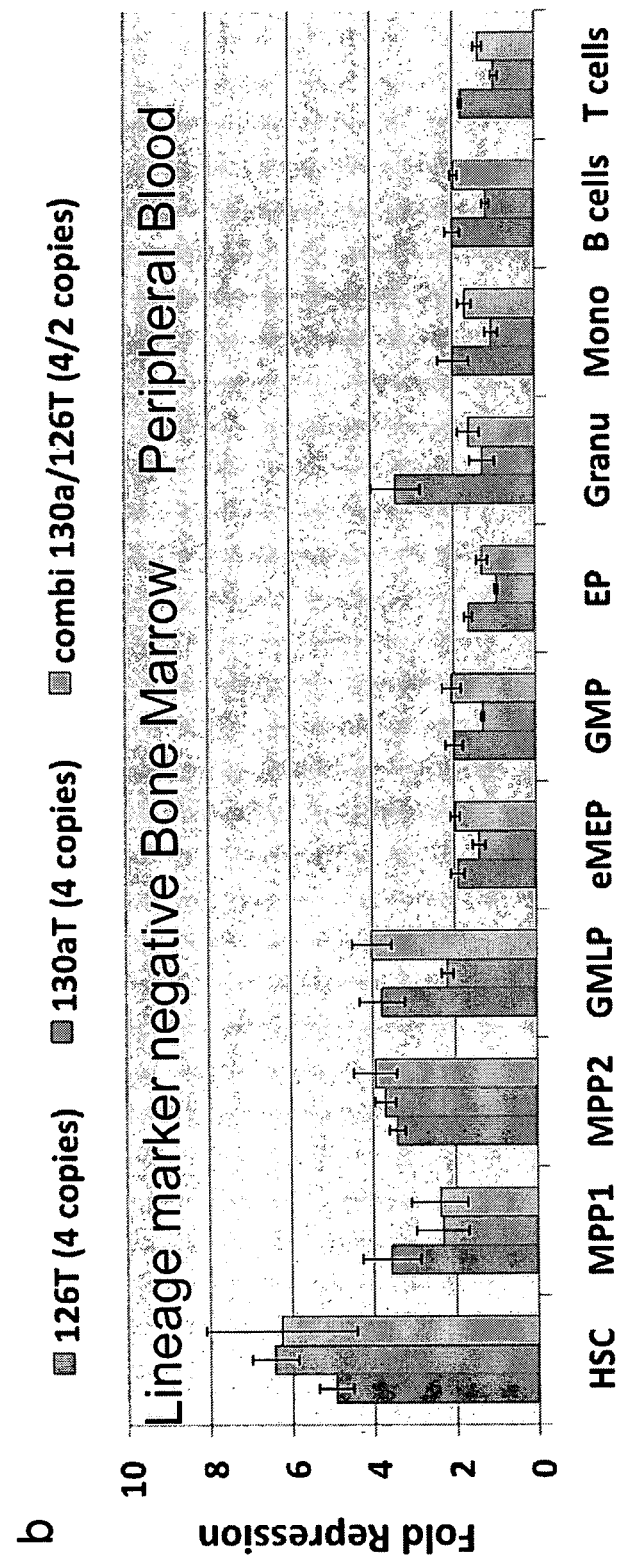
Figure 24:
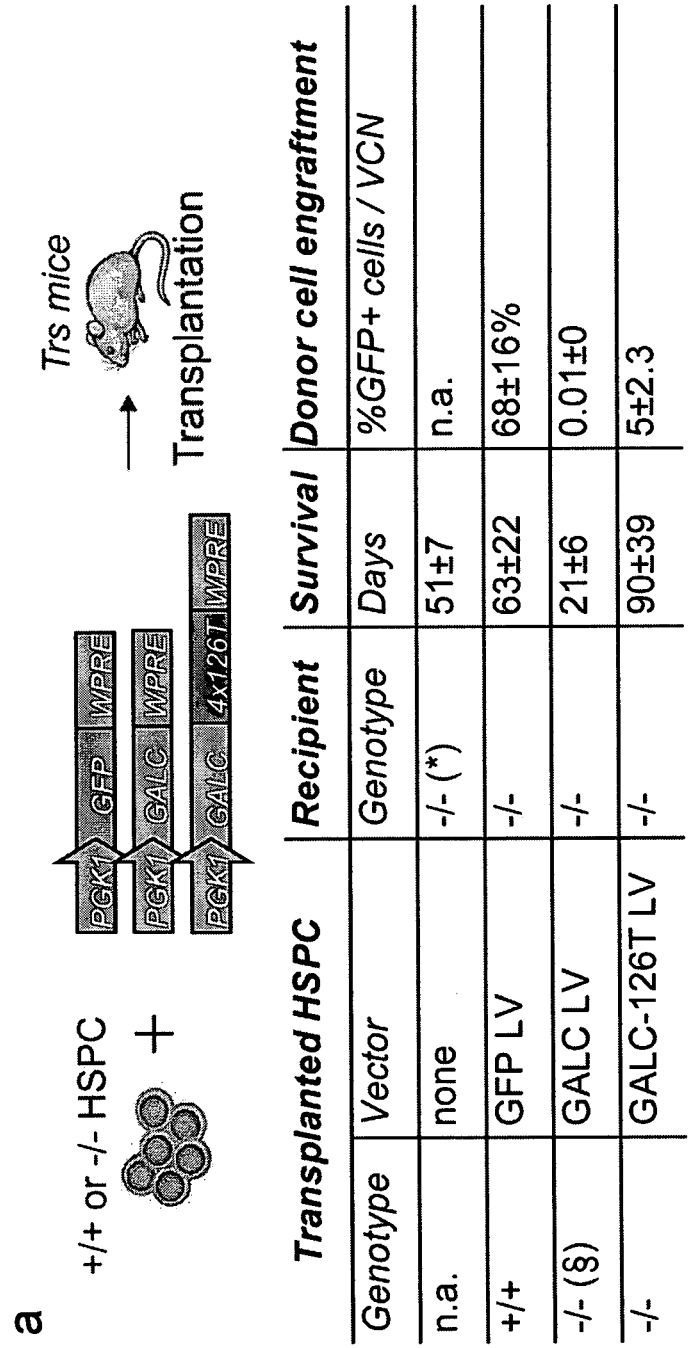
Figure 24:
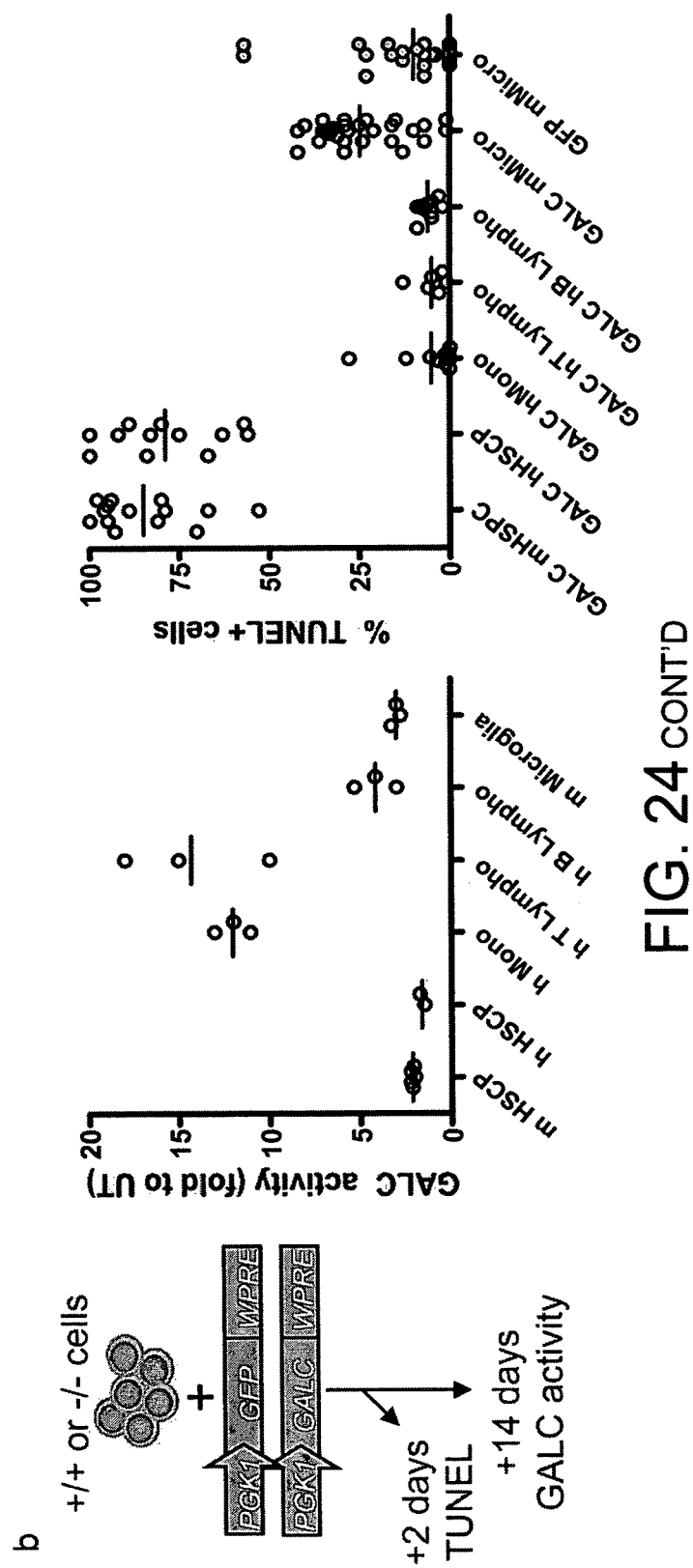
Figure 24:
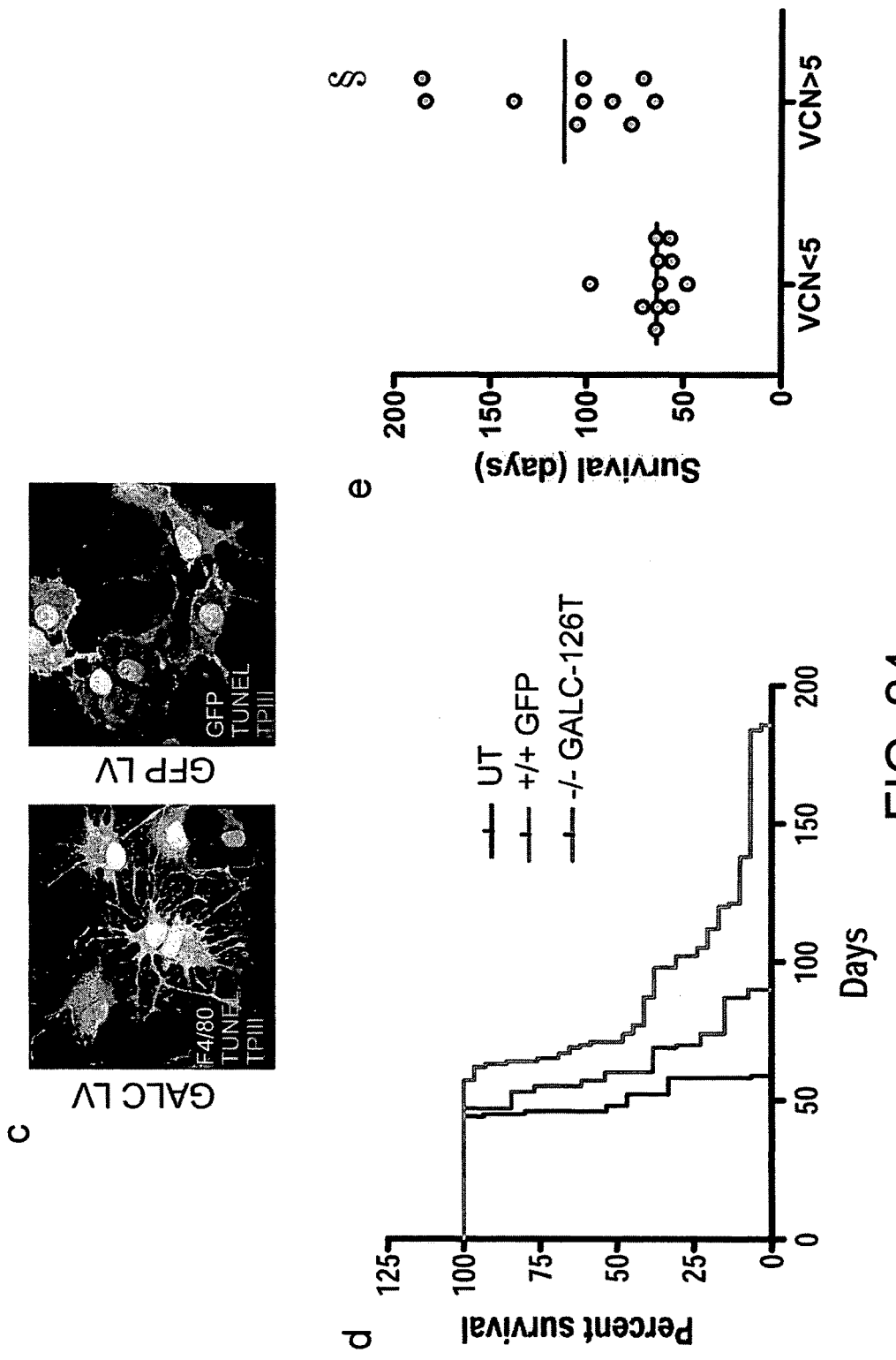

FIG. 24. Improved survival of GLD mice after HSC gene therapy. Galc−/− or +/+ murine HSPC were transduced with the indicated vectors and intravenously transplanted into Trs mice according to the experimental scheme in (A). Average survival ±SD and average engraftment of the transduced cells, measured as % of GFP+ cells or VCN detected in the BM of transplanted mice (±SD) at 120 days or at death; are shown (n=4-26 per group). (§) Similar results were obtained using +/+ mHSPC. The survival of untreated GLD mice is shown in the first row (*=Not-irradiated; n.a.=non applicable). (B) Human primary monocytes, B and T lymphocytes and murine microglia were transduced with the indicated vectors. GALC activity (expressed as fold to untransduced cells—UT) was measured on the cultured cells ≥5 days post-transduction (center panel) and TUNEL assay (expressed as % TUNEL+ cells) was performed 2 days post-transduction (right panel). Data from GALC-transduced murine and human HSPC (from FIG. 5) and % TUNEL+ cells in GFP-transduced microglia are reported for comparison. Each dot represents an individual sample, in which ≥6 fields and ≥250 cells were counted. (C) Representative images of TUNEL staining on microglia cells transduced with GALC LV or GFP LV, as indicated, and stained for the microglia marker F4/80 (GALC transduced cells) or GFP. Nuclei were labeled with ToproIII (TPIII). Magnification 100×. (D) Kaplan-Meier survival curves of Trs mice transplanted with either Galc−/− HSPC transduced by GALC-126T LV (n=26) or Galc+/+ HSPC transduced by GFP LV (n=10) and of untreated affected controls (UT) (n=15). GALC-126T versus GFP at log rank tests for pair wise comparison: p=0.002; GALC-126 versus UT: p<0.0001. (E) GALC-126T transplanted mice were divided into two groups according to the VCN measured on total BM cells at the time of death. Survival is shown for animals carrying less (mean±SD=67±13 days) or more (mean±SD=117±43 days) than 5 LV copies in BM cells, being 5 the average VCN measured in the BM of the entire population of treated mice. (F-I) GALC activity (light blue) was qualitatively evaluated on brain sections from GALC-126T transplanted and control mice. Representative sections from the hippocampus (F, G) and pons (H, I) of GALC-126T transplanted mice, as compared to WT and untreated Trs mice are shown. GALC assay was coupled to the microglia/macrophage Ibal marker (F, G) and to the hematopoietic marker CD45 (H, I). A marked infiltration of activated hematopoietic cells is present in untreated and GALC-126T transplanted Trs mice, the latter showing GALC activity both within the transduced HSPC hematopoietic progeny (arrowheads in G and I showing co-staining of GALC [in blue] and Ibal [G] and CD45 [I] in brown) and in Ibal−, CD45− non-hematopoietic cells. Magnification 20× in (F, H) and 40× in (G, I).

MicroRNAs (miRNAs)

It has long been a central dogma of biology that genetic information flows from DNA to mRNA to protein. In other words, it has been assumed that genes code for proteins, and that proteins fulfil all cellular functions, including the regulation of gene expression programs. However, only a minority of RNA transcripts (2-3%) code for proteins in higher eukaryotes, calling into question the central dogma that proteins are the only effectors of cell function (Mercer et al., 2009). In fact, there is now emerging evidence that a class of non-coding small RNAs, called "microRNAs", fulfil a fundamental role in the regulation of gene expression. MicroRNAs (miRNAs) are (Biffi et al., 2004; Sadelain M., 2006; Sadelain et al., 2005; Gaziev et al., 2005; Yesilipek M A., 2006; Abonour et al., 2000) nucleotide long, non-coding RNAs that negatively regulate gene expression at the post-transcriptional level by triggering a process called RNA interference (RNAi, see below) (Bartel D P., 2004). MicroRNAs were first discovered in *Caenorhabditis elegans* in the form of lin-4 and let-7, and they were shown to regulate the timing of larval development. (Lee et al., 1993; Reinhart et al., 2000). This finding led to the search for similar non-coding RNAs controlling gene expression in higher eukaryotes. The discovery that all organisms express miRNAs, many of which are phylogenetically conserved across species, has been conceived as a revolution in the field of biology. According to the reference microRNA database (http://microma.sanger.ac.uld) 695 different miRNAs have been identified in humans at the time of writing. MicroRNAs have been implicated in almost all biological processes, including development, differentiation, proliferation and apoptosis (Xiao and Rajewsky, 2009). They also play important roles in diseases such as cancer, heart failure and metabolic disorders (Xiao et al., 2009; Divaka et al., 2008; Krutzfeldt et al., 2006).

MicroRNA genes are scattered across all human chromosomes, except for the Y chromosome. They can be either located in non-coding regions of the genome or within introns of protein-coding genes. Around 50% of miRNAs appear in clusters which are transcribed as polycistronic primary transcripts (Lagos-Quintana et al., 2003). Similar to protein-coding genes, miRNAs are usually transcribed from polymerase-II promoters, generating a so-called primary miRNA transcript (pri-miRNA). This pri-miRNA is then processed through a series of endonucleolytic cleavage steps, performed by two enzymes belonging to the RNAse Type III family, Drosha and Dicer. From the pri-miRNA, a stem loop of about 60 nucleotides in length, called mima precursor (pre-mirna), is excised by a specific nuclear complex, composed of Drosha and DiGeorge syndrome critical region gene (DGCR8), which crops both strands near the base of the primary stem loop and leaves a 5' phosphate and a 2 bp long, 3' overhang. The pre-mirna is then actively transported from the nucleus to the cytoplasm by RAN-GTP and Exportin—(Yi et al., 2003; Lund et al., 2004). Then, Dicer performs a double strand cut at the end of the stem loop not defined by the Drosha cut, generating a 19-24 bp duplex, which is composed of the mature miRNA and the opposite strand of the duplex, called miRNA* (Bartel D P., 2004). In agreement with the thermodynamic asymmetry rule, only one strand of the duplex is selectively loaded into the RNA-induced silencing complex (RISC), and accumulates as the mature microRNA. This strand is usually the one whose 5'end is less tightly paired to its complement, as was demonstrated by single-nucleotide mismatches introduced into the 5'end of each strand of siRNA duplexes (Tomari et al., 2005). However, there are some miRNAs that support accumulation of both duplex strands to similar extent (Schwarz et al., 2003).

MicroRNAs trigger RNAi, very much like small interfering RNAs (siRNA) which are extensively being used for experimental gene knockdown. The main difference between miRNA and siRNA is their biogenesis. Once loaded into RISC, the guide strand of the small RNA molecule interacts with mRNA target sequences preferentially found in the 3' untranslated region (3'UTR) of protein-coding genes. It has been shown that nucleotides 2-8 counted from the 5'end of the miRNA, the so-called seed sequence, are essential for triggering RNAi (Brennecke et al., 2005). If the whole guide strand sequence is perfectly complementary to the mRNA target, as is usually the case for siRNAs and plant miRNAs, the mRNA is endonucleolytically cleaved by involvement of the Argonaute (Ago) protein, also called "slicer". of the small RNA duplex into the RNA-induced silencing complex (RISC). DGRC (DiGeorge syndrome critical region gene 8) and TRBP (TAR (HW) RNA binding protein 2) are double-stranded RNA-binding proteins that facilitate mature miRNA biogenesis by Drosha and Dicer RNase III emzymes, respectively. The guide strand of the miRNA duplex gets incorporated into the effector complex RISC, which recognizes specific targets through imperfect base-pairing and induces post-transcriptional gene silencing. Several mechanisms have been proposed for this mode of regulation: miRNAs can induce the repression of translation initiation, mark target mRNAs for degradation by dead-enylation, or sequester targets into the cytoplasmis P-body.

On the other hand, if only the seed is perfectly complementary to the target mRNA but the remaining bases show incomplete pairing, RNAi acts through multiple mechanisms leading to translational repression (Bartel D P., 2004; Pillai R S., 2005; Bartel D P., 2009). Eukaryotic mRNA degradation mainly occurs through the shortening of the polyA tail at the 3' end of the mRNA, and de-capping at the 5'end, followed by 5'-3' exonuclease digestion and accumulation of the miRNA in discrete cytoplasmic areas, the so called P-bodies, enriched in components of the mRNA decay pathway (Lui et al., 2005).

MiRNAs which are useful in the present invention are miRNAs which are expressed in hematopoietic stem and/or progenitor cells but which are not expressed extensively in differentiated cells. Preferred examples include mir-130a, mir-126 and mir-223. Other suitable microRNAs include microRNAs expressed in embryonic stem cells and the so-called iPS cells. For example, miR-302a, miR-373 and miR-292 are specifically expressed in pluripotent cells (ES, iPS) but not in adult-type stem cells or differentiated cells. let-7 family microRNAs are expressed in all cells except from pluripotent ones (ES, iPS). miR-124a is specifically expressed in neurons.

Gene Vectors

The miRNA may be used with a suitable gene vector, i.e. a vector suitable for delivering a gene (transgene) of interest, such as a viral vector. Viral vectors suitable for gene therapy are well known in the art. Examples of viral vectors useful for the present invention are described in WO2007/000668.

Viruses from several different families have been modified to generate viral vectors for gene delivery. Viruses which can be used in the present invention include retroviruses, lentivirus, adenoviruses, adeno-associated viruses, herpes simplex viruses, picornaviruses, and alphaviruses. The present invention preferably employs retroviruses, including lentiviruses.

The present invention can be used to control expression of a transgene included in the vector. The invention can also be used to control expression of the vector. For example, a vector which can be controlled by the mir-RNAs of the present invention is an oncolytic virus.

Hematopoietic Stem Cell Transplantation

Hematopoietic stem cell transplantation (HSCT) is the transplantation of blood stem cells derived from the bone marrow (in this case known as bone marrow transplantation) or blood. Stem cell transplantation is a medical procedure in the fields of hematology and oncology, most often performed for people with diseases of the blood, bone marrow, or certain types of cancer.

With the availability of the stem cell growth factors GM-CSF and G-CSF, most hematopoietic stem cell transplantation procedures are now performed using stem cells collected from the peripheral blood, rather than from the bone marrow. Collecting peripheral blood stem cells provides a bigger graft, does not require that the donor be subjected to general anesthesia to collect the graft, results in a shorter time to engraftment, and may provide for a lower long-term relapse rate.

Hematopoietic stem cell transplantation remains a risky procedure with many possible complications; it has traditionally been reserved for patients with life-threatening diseases. While occasionally used experimentally in non-malignant and nonhematologic indications such as severe disabling auto-immune disease and cardiovascular disease, the risk of fatal complications appears too high to gain wider acceptance.

Many recipients of HSCTs are multiple myeloma or leukemia patients who would not benefit from prolonged treatment with, or are already resistant to, chemotherapy. Candidates for HSCTs include pediatric cases where the patient has an inborn defect such as severe combined immunodeficiency or congenital neutropenia with defective stem cells, and also children or adults with aplastic anemia who have lost their stem cells after birth. Other conditions treated with stem cell transplants include sickle-cell disease, myelodysplastic syndrome, neuroblastoma, lymphoma, Ewing's Sarcoma, Desmoplastic small round cell tumor and Hodgkin's disease. More recently non-myeloablative, or so-called "mini transplant," procedures have been developed that require smaller doses of preparative chemo and radiation. This has allowed HSCT to be conducted in the elderly and other patients who would otherwise be considered too weak to withstand a conventional treatment regimen. The present invention aims to widen the therapeutic application of such treatments by improving their safety and/or efficacy.

Diseases

The present invention is particularly useful in gene therapy. In particular those therapies which involve the expression of a potentially toxic transgene. Diseases which can be treated in accordance with the present invention include lysosomal storage disorders (LSD) such as globoid Cell Leukodystrophy (GLD). Another example of a disease treatable by the present invention is chronic granulomatous disease (CGD).

Globoid Cell Leukodystrophy (GLD) or Krabbe disease is caused by mutations in the GALC gene, which causes a deficiency of an enzyme called galactosylceramidase. The buildup of unmetabolized lipids affects the growth of the nerve's protective myelin sheath (the covering that insulates many nerves) and causes severe degeneration of motor skills. As part of a group of disorders known as leukodystrophies, Krabbe disease results from the imperfect growth and development of myelin. A gene therapy treatment of GLD involves inducing the GALC gene into the patient. For example, the GALC could be intoduced into HSPC or HSC which is then transplanted into the patient. The present inventors found toxicity and in vitro and in vivo functional impairment of murine and human HSPC after LV-mediated GALC gene transfer and expression. This toxicity could be overcome by using the gene vectors of the present invention.

The delivery of one or more therapeutic genes by a vector system according to the present invention may be used alone or in combination with other treatments or components of the treatment.

For example, the vector of the present invention may be used to deliver one or more transgene(s) useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the vector of the present invention may be used to deliver one or more transgene(s) useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the retroviral vector of the present invention may be used to deliver one or more transgenes(s) useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimoorchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

The present invention also provides a pharmaceutical composition for treating an individual by gene therapy, wherein the composition comprises a therapeutically effective amount of the vector of the present invention comprising one or more deliverable therapeutic and/or diagnostic transgenes(s) or a viral particle produced by or obtained from same. The pharmaceutical composition may be for human or animal usage. Typically, a physician will determine the actual dosage which will be most suitable for an individual subject and it will vary with the age, weight and response of the particular individual.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant (s), suspending agent(s), coating agent(s), solubilising agent (s), and other carrier agents that may aid or increase the viral entry into the target site (such as for example a lipid delivery system).

Where appropriate, the pharmaceutical compositions can be administered by any one or more of: inhalation, in the form of a suppository or pessary; topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The delivery of one or more therapeutic genes by a vector system according to the invention may be used alone or in combination with other treatments or components of the treatment. Diseases which may be treated include, but are not limited to: cancer, neurological diseases, inherited diseases, heart disease, stroke, arthritis, viral infections and diseases of the immune system. Suitable therapeutic genes include those coding for tumour suppressor proteins, enzymes, pro-drug activating enzymes, immunomodulatory molecules, antibodies, engineered immunoglobulin-like molecules, fusion proteins, hormones, membrane proteins, vasoactive proteins or peptides, cytokines, chemokines, antiviral proteins, antisense RNA and ribozymes.

EXAMPLES

Nucleotide sequences: in bold: target sequence complementary to the miRNA. In general, we use 4 copies of miRNA targets separated by a 4-6 nucleotide linker. This can, however, be optimized.

```
                                           (SEQ ID NO: 1)
miR-126: UCGUACCGUGAGUAAUAAUGCG miR-126T sequence:
                                           (SEQ ID NO: 2)
GCATTATTACTCACGGTACGACGATGCATTATTACTCACGGTACGAACG

CGTGCATTATTACTCACGGTACGATCACGCATTATTACTCACGGTACGA (SEQ ID NO: 3)
miR-130a: CAGUGCAAUGUUAAAAGGGCAU miR-130aT sequence:
                                           (SEQ ID NO: 4)
ATGCCCTTTTAACATTGCACTGTTCGAAATGCCCTTTTAACATTGCACTG

ACGCGTATGCCCTTTTAACATTGCACTGATGCATATGCCCTTTTAACATT

GCACTG (SEQ ID NO: 5)
miR-223: UGUCAGUUUGUCAAAUACCCA
```

-continued miR-223T sequence:
(SEQ ID NO: 6)
GGGGTATTTGACAAACTGACACGATGGGGTATTTGACAAACTGACAACC

GGTGGGGTATTTGACAAACTGACATCACGGGGTATTTGACAAACTGACA

126T/130aT 2/2 combination:
(SEQ ID NO: 7)
GCATTATTACTCACGGTACGACGATGCATTATTACTCACGGTACGAACGC

GTATGCCCTTTTAACATTGCACTGATGCATATGCCCTTTTAACATTGCAC

TG 126T (2 targets):
(SEQ ID NO: 8)
GCATTATTACTCACGGTACGACGATGCATTATTACTCACGGTACGA Triple combination target (126T/130aT/223T,
2 targets each):
(SEQ ID NO: 9)
GCATTATTACTCACGGTACGACGATGCATTATTACTCACGGTACGAACGC

GTATGCCCTTTTAACATTGCACTGATGCATATGCCCTTTTAACATTGCAC

TGCCCCGGTGGGGTATTTGACAAACTGACATCACGGGGTATTTGACAAAC

TGACA

Example 1

Construction and Validation of Lentiviral microRNA Reporter Vectors

In order to determine the activity of miRNAs in hematopoietic cells including rare and poorly characterized populations like HSC, we took advantage of our prior observation that transgenes expressed from lentiviral vectors can be down-regulated by endogenous miRNA for which artificial binding sites (miRT, miRNA target sites) are added to the transgene cassette (Brown B D., 2006). We thus aimed at constructing lentiviral miRNA reporter vectors reading out miRNA activity in real time and at single cell resolution. Bidirectional lentiviral vectors (Bd.LV) allow the coordinate expression of two reporter genes driven by a constitutive promoter with bidirectional activity, composed of the human phosphoglycerate kinase (PGK) promoter fused to a TATA-box in the form of a minimal cytomegalovirus (CMV) promoter in opposite orientation (Amendola M., 2005) Since this design allows both reporters to be expressed as two independent transcripts, one of them can be made responsive to miRNA activity by adding miRT to the 3'UTR ("miRNA reporter"), while the other one, not equipped with miRT, will not be affected by the miRNA and will serve as an internal control ("normalizer"). We cloned a panel of such Bd.LVs containing the green fluorescent protein (GFP) as the miRNA reporter and a truncated version of the human low-affinity nerve growth factor receptor (NGFR) as a constitutively expressed normalizer.

We chose to investigate two miRNAs thought to be expressed in the hematopoietic tissue, miR-223 and miR-126-3p. miR-223 was reported to be highly and specifically expressed in differentiated myeloid cells, but absent in lymphocytes (Fazi F., 2005), allowing us to test the performance of our reporter Bd.LVs in well characterized lineages. Moreover, we wanted to explore how miR-223 was expressed in hematopoietic stem and progenitor cell (HSPC) populations. From a gene therapy perspective, it would be highly relevant to identify miRNAs that are strongly expressed in HSPC but not in differentiated progeny, in order to prevent off-target transgene expression in sensitive stem cell populations while fully maintaining therapeutic correction of the diseased progeny. Large-scale miRNA cloning has suggested that miR-126 might fulfil these criteria, as it was specifically detected in human CD34+ HSPC but not in other hematopoietic cell population (Landgraf et al., 2007).

Figure 1:
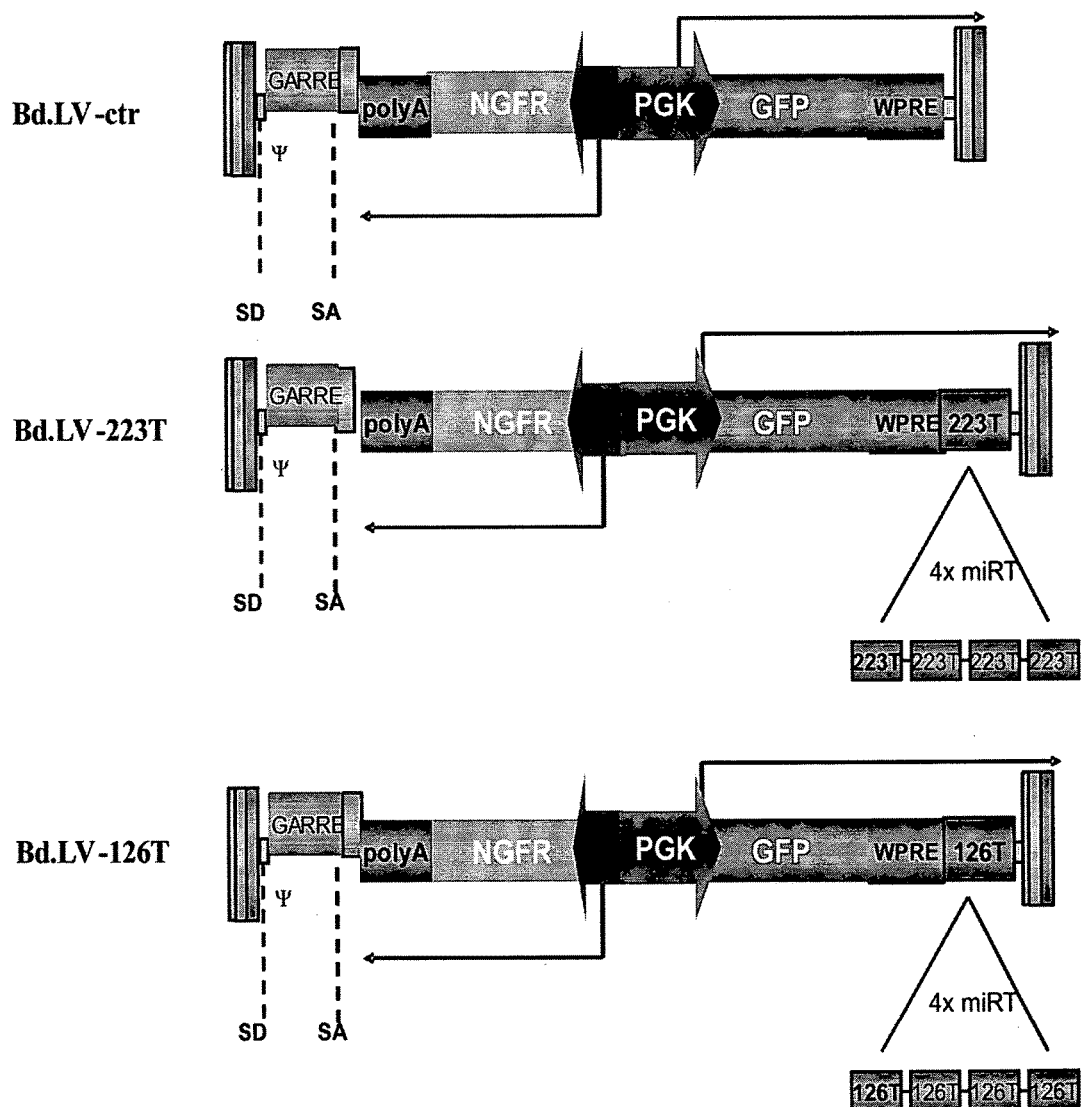
FIG. 1. Schematic representation of bidirectional miRNA-regulated lentiviral reporter vectors. Shown here are representative structures of miRNA regulated bidirectional vectors (Bd.LVs), containing the green fluorescent protein (GFP) as the miRNA reporter and a truncated form of the human low affinity nerve growth factor receptor (NGFR) as a constitutively expressed normalizer. While Bd.LV-ctr does not contain any miRNA target sequence (miRT), Bd.LV-223T and Bd.LV-126T were constructed by the addition of 4 tandem repeats containing 21 bp perfectly complementary to miR-223 or miR-126, respectively.
Figure 2:
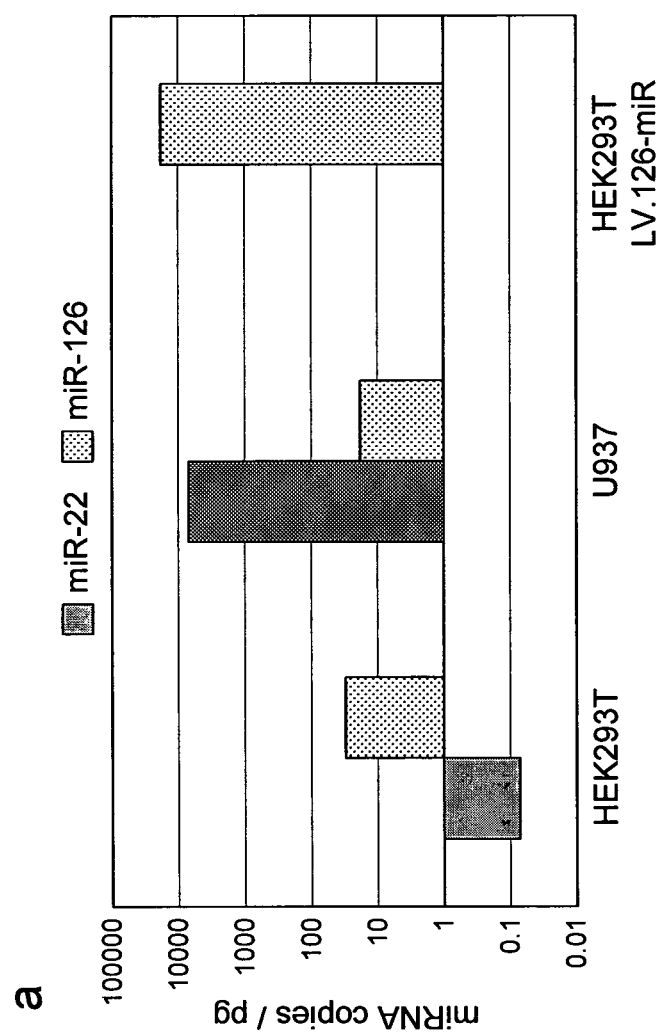
FIG. 2. Evaluation of miRNA reporter Bd.LVs in cell lines. a) Quantitative analysis of miR-223 and miR-126 expression levels (copies/pg) in HEK293T, U937 and HEK293T cells that ectopically express miR-126 by transduction with an LV containing the pri-mir-126 under control of a ubiquitous promoter (HEK293T.LV.miR-126). b) Representative FACS analysis of HEK-293T, U937, HUVEC and HEK293T.LV.miR-126 cells, transduced with the indicated miRNA regulated Bd.LVs. Cells are analyzed for GFP "miRNA reporter" and NGFR "normalizer" expression. c) Formula for calculation of miRNA-mediated fold repression of the reporter gene expression at the protein level and at the RNA level. Histograms show miR-223 and miR-126 activity in cell lines calculated as GFP FR values at the protein level. Diamonds represent GFP FR at the RNA level.
Figure 2:
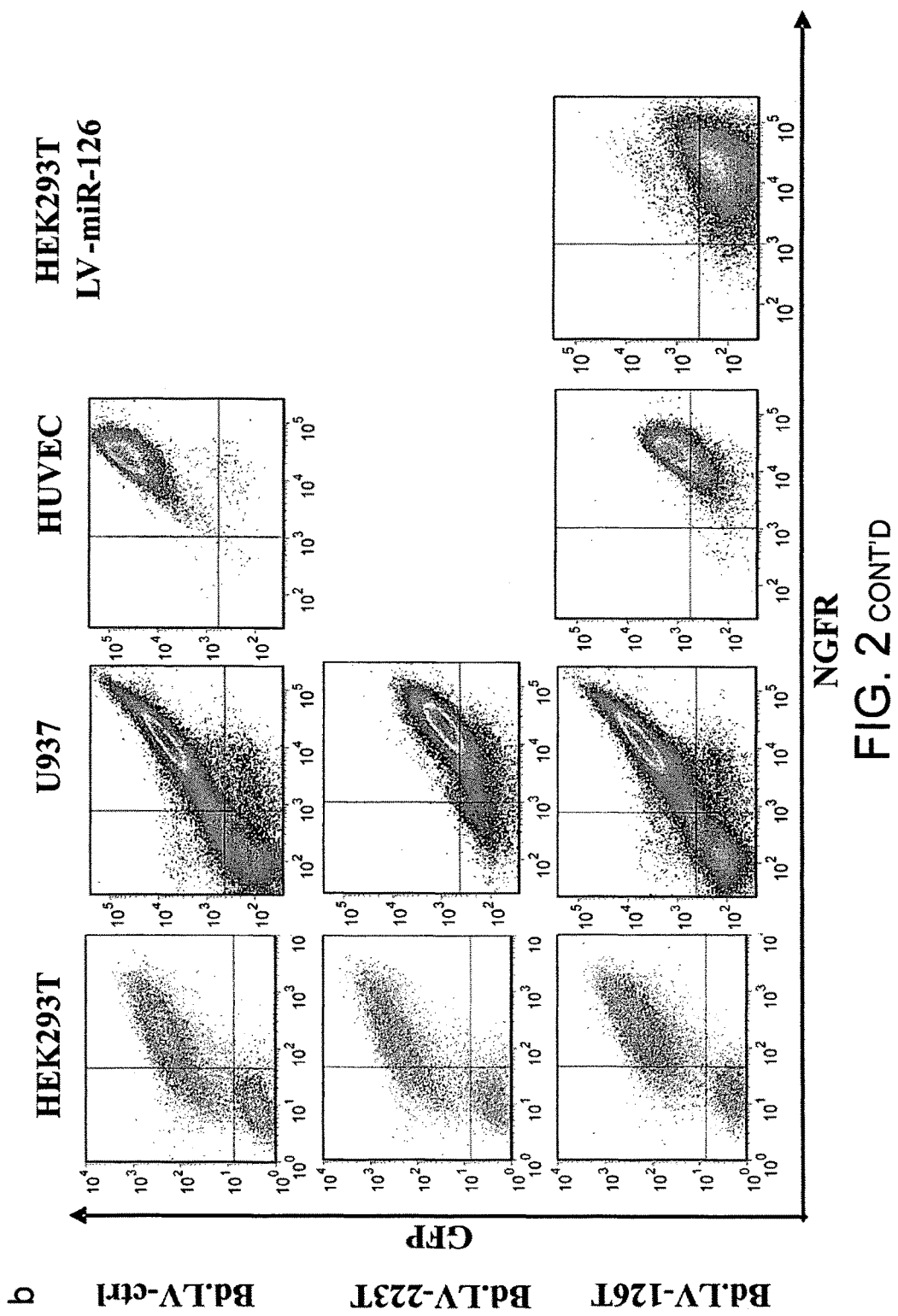
Figure 2:
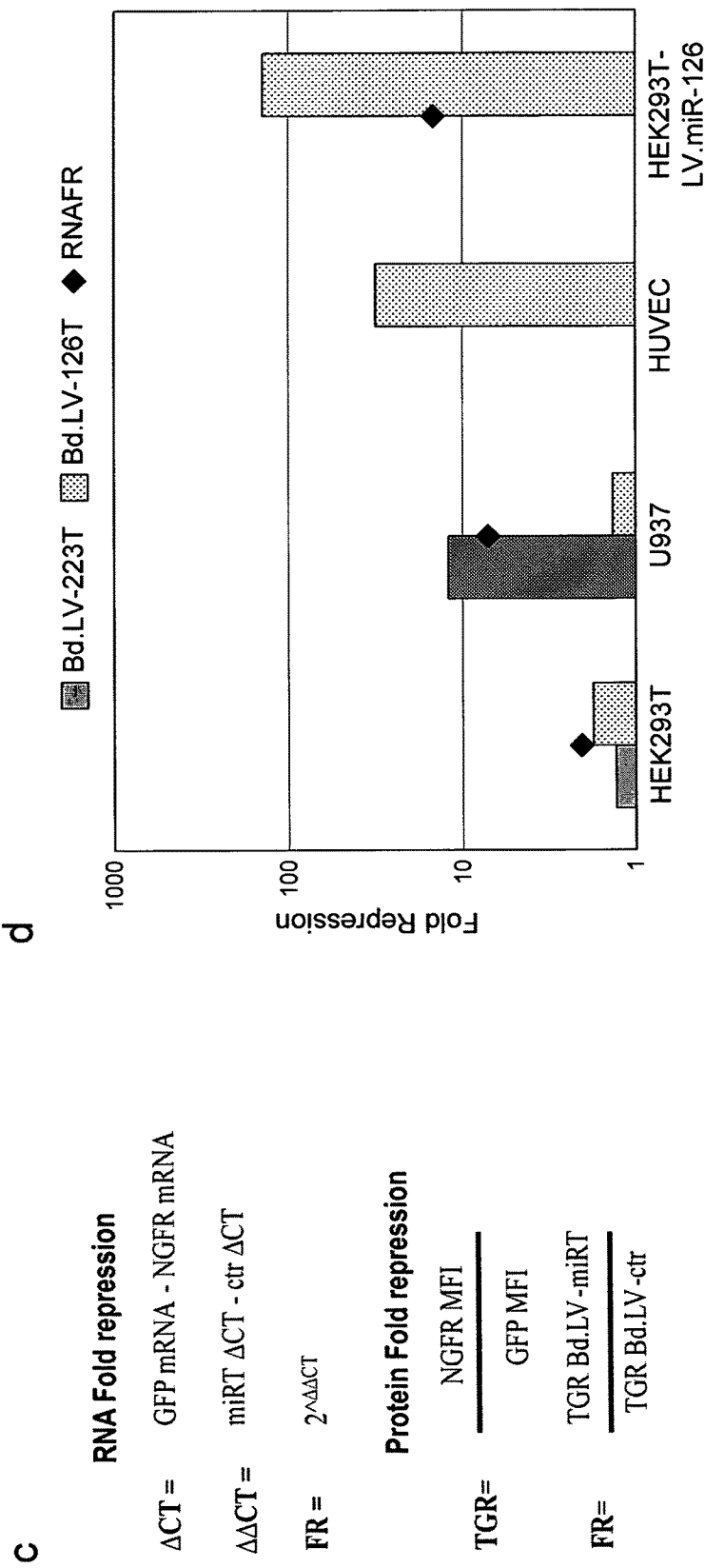

We produced reporter Bd.LVs for miR-223 and miR-126-3p (Bd.LV-223T and Bd.LV-126T, respectively), as well as a control Bd.LV not containing any miRT (FIG. 1). These vectors were then evaluated on a panel of different cell types (FIG. 2). HEK293T embryonic kidney cells, U937 monocytic cells and human umbilical vein endothelial cells (HUVECs) were transduced with matched doses of Bd.LV-ctr, Bd.LV-223T and Bd.LV-126T, and analyzed for reporter expression by flow cytometry (FACS) several days after transduction. HEK293T cells express low to undetectable levels of miR-223 or miR-126, while U937 cells strongly express miR-223 but not miR-126 (FIG. 2a) and HUVECs express miR-126 but not miR-223 (Kuehbacher et al., 2007). As an additional control, we engineered HEK293T cells to ectopically express miR-126 (FIG. 2a) by transduction with an LV containing the pri-mir-126 under control of a ubiquitous promoter (now referred to as HEK293T.LV.miR-126, as opposed to the wild-type HEK293T cells).

In HEK293T cells, the GFP mean fluorescence intensity (MFI) of NGFR-expressing, transduced cells was identical for all three Bd.LVs (FIG. 2b, left column), confirming that neither miR-223 nor miR-126-3p were expressed in these cells. In sharp contrast, U937 cells transduced with Bd.LV.223T showed a substantial reduction in GFP MFI compared to Bd.LV.126T or Bd.LV.ctrl, indicating that miR-223, but not miR-126, was biologically active in U937 cells. On the contrary, HUVECs showed a repression of GFP specifically for Bd.LV-126T when compared to the control vector. Similarly, HEK293T.LV.miR-126 cells transduced with the Bd.LV-126T reporter strongly down-regulated GFP expression compared to wild-type HEK293T cells (compare last to first plot in the third row of FIG. 2b).

To describe miRNA activity in more quantitative terms, we calculated a "Protein Fold Repression" value (FR) based on normalized mean fluorescence intensities (MFI) of the miRNA reporter Bd.LV respect to the control Bd.LV (FIG. 2c). To account for different levels of gene transfer between vector groups, we made use of the internal normalizer, NGFR, which is transcribed in stechiometric amounts with the miRNA reporter, GFP. Thus, we gated the FACS analysis on the NGFR positive cells, and calculated a "transgene ratio" (TGR), dividing the NGFR MFI by the GFP MFI for each Bd.LV. The TGR obtained for the miRNA reporter vectors (Bd.LV.223T or Bd.LV.126T, respectively) were then divided by the TGR of the control Bd.LV. This quotient, which we call "fold repression" from now on, is independent on vector dose and transduction level (at least within the linear portion of the vector dose-response curve) and provides a quantitative readout for miRNA activity in the analyzed cells (FIG. 2c). Our miRT were designed to be perfectly complementary to the cognate miRNA. We thus expected that transcripts recognized by the miRNA were degraded. To prove this, we measured NGFR and GFP mRNA transcripts by RT-QPCR in U937 and HEK293T.LV.miR-126 cells, and calculated an "RNA Fold Repression" as outlined in FIG. 2c. Indeed, GFP transcripts were reduced relative to NGFR transcripts in U937.Bd.LV.223T cells as well as in HEK293T.LV.miR-126.Bd.LV.126T cells, as shown by the calculated RNA Fold Repression values of 7 and 14, respectively (FIG. 2c, diamonds).

Taken together, these results indicate that our miRNA-regulated Bd.LVs faithfully reported miRNA activity in cell lines, consistent with our own and previously published miRNA expression data. In addition to conventional miRNA profiling techniques, our vectors report not just the presence of a miRNA, but also its bioactivity. FACS analysis of cells carrying our Bd.LV reporter allows assessing miRNA activity at the single cell level and is thus suitable for analyzing heterogenous cell mixtures, which can be further subdivided by immunophenotyping.

Characterization of miR-223 and miR-126 Activity in the Mouse Hematopoietic System Once demonstrated the reliability of the reporter Bd.LVs in measuring miRNA activity in cell lines, we moved to investigate the activity of the aforementioned miRNAs in primary hematopoietic cells. To this aim, we took advantage of the murine model because it is widely available, easily manipulated in an experimental setting and well-characterized. In fact, when aiming to define miRNA activity in rare HSPC populations, the murine hematopoietic system, well characterized by surface markers, represents a great advantage. Our experimental approach was to enrich murine HSPC from bone marrow by depleting lineage-marker positive cells, to transduce them with lentiviral miRNA reporter vectors and transplant these cells into lethally irradiated congenic recipient mice. microRNA activity was then monitored in peripheral blood leukocytes over time to determine their activity in differentiated cells. After stable engraftment had been reached, mice were euthanized, and miRNA activity was determined in multiple bone marrow populations defined by surface immunophenotyping. In this way, we wanted to assess whether these miRNAs were expressed in prospectively identified HSPC. In particular, we wanted to determine whether miR-126 is present in the most primitive HSC compartment. The first set of mice was transplanted with HSPC transduced by the previously described reporter Bd.LVs (see FIG. 1; Bd.LV-ctr, n=5 mice transplanted; Bd.LV-223T, n=6 mice; or Bd.LV-126T, n=4 mice).

Figure 3:
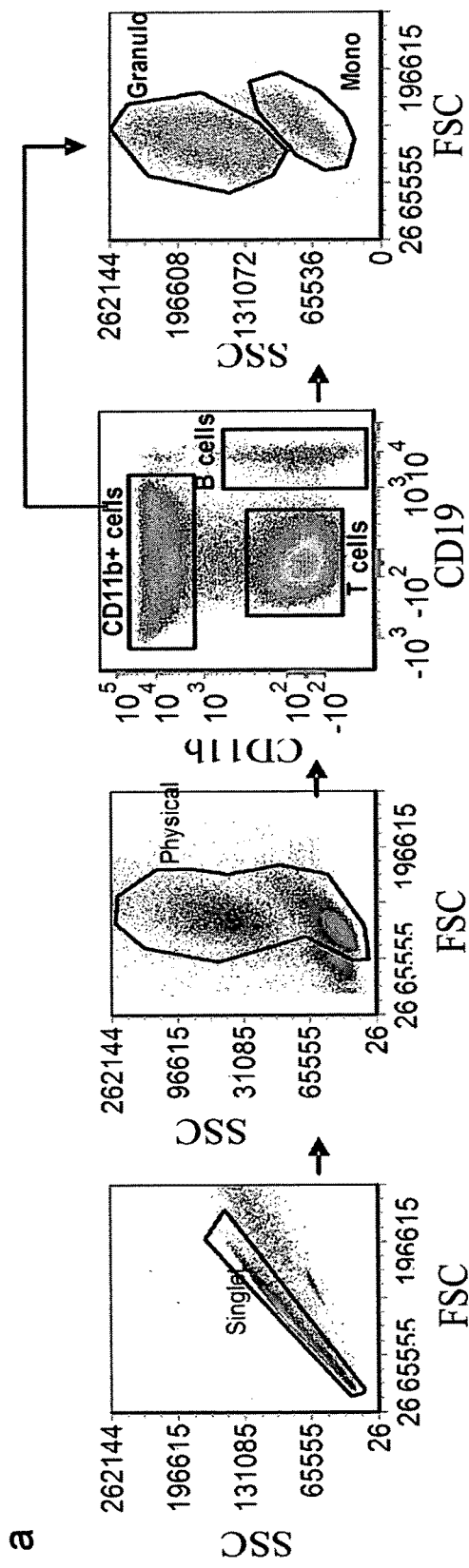
FIG. 3. Evaluation of miRNA reporter BdLVs in vivo. Lineage$^{-/low}$ bone marrow (BM) hematopoietic stem and progenitor cells (HSPC) were transduced with bidirectional miRNA reporter lentiviral vectors (BdLVs) for miR-223 and miR-126, and transplanted into recipient mice. Peripheral blood cells of mice stably engrafted with cells carrying the miRNA reporter was analyzed by FACS. a) Gating strategy used to identify the major leukocyte population from murine peripheral blood: granulocytes (CD11b+, SSChigh), monocytes (CD11b+, SSClow), B cells (CD19+) and T cells (CD11b– CD19b–). b) Representative FACS analysis of GFP and NGFR expression within murine peripheral blood subsets. c) GFP FR values (mean+/–SD) in peripheral blood subpopulations from mice transplanted with HSPC transduced with either Bd.LV-ctr (n=5), Bd.LV-223T (n=6) or Bd.LV-126T(n=4).
Figure 3:
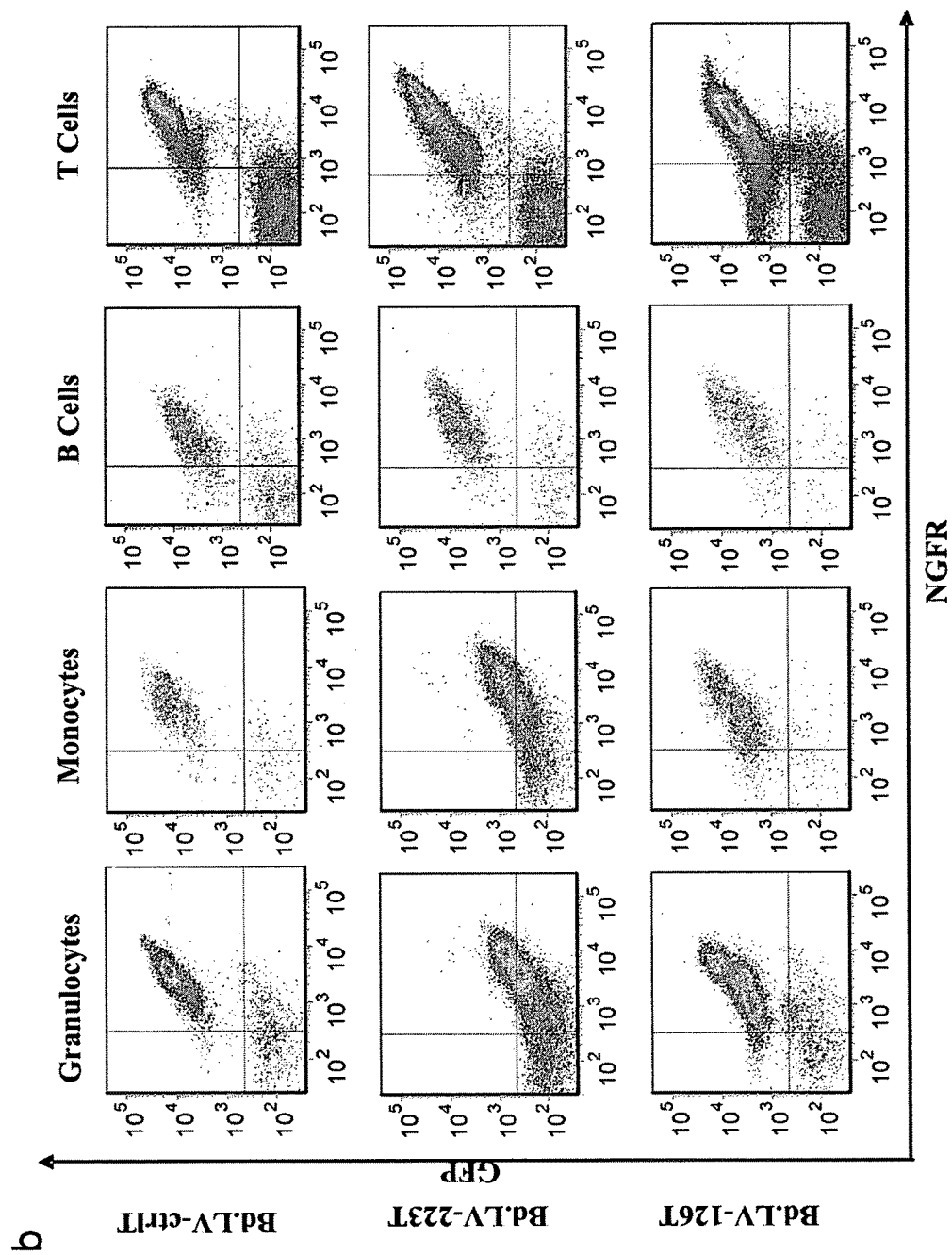
Figure 3:
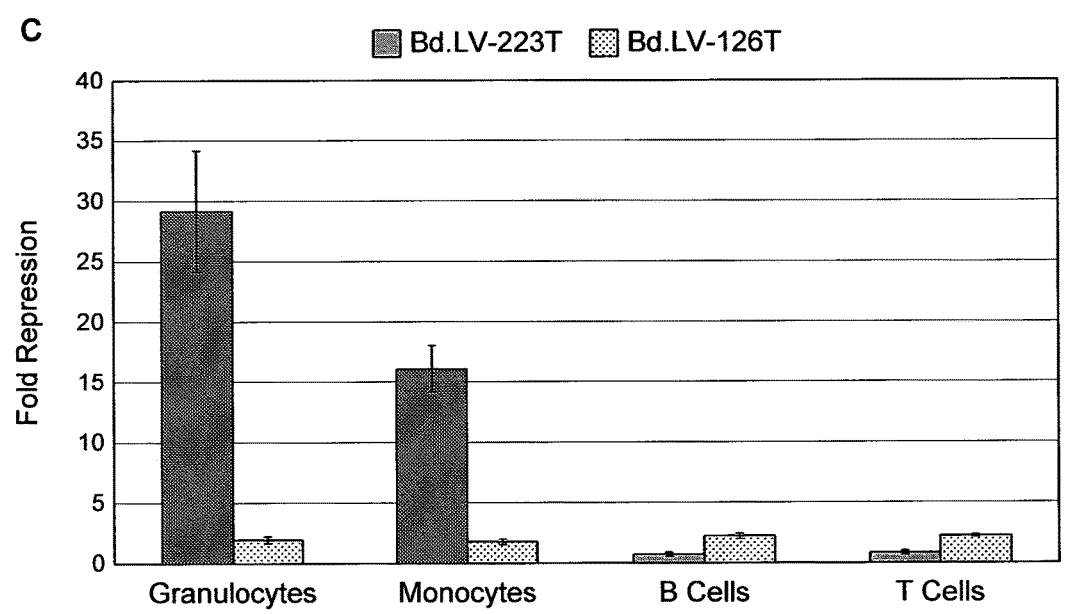

Peripheral blood (PB) was sampled 8 weeks after transplantation, and leukocyte populations were sorted according to physical parameter and surface markers into granulocytes (CD11b+ side scatterhi SSChi), monocytes (CD11b+SSClo), B cells (CD19+) and T cells (CD11b−CD19−) (FIG. 3a). GFP miRNA reporter and NGFR normalizer expression was quantified within these leukocyte subsets by FACS (FIG. 3b). While GFP was similarly expressed in all leukocyte subsets derived from Bd.LV-ctr- and Bd.LV-126T-transduced HSPC, we noted a profound down-regulation of GFP specifically in PB myeloid cells but not in lymphocytes within the Bd.LV-223T group. Quantification of miR-223 activity indicated a 30-fold and 17-fold repression in granulocytes and monocytes, respectively, while miR-126 was not active in PB leukocytes (FIG. 3c). In order to characterize the miR-223 and miR-126 profile in distinct HSPC subsets, we sacrificed Bd.LV reporter mice and subjected their bone marrow to a multi-color immunophenotyping analysis in order to prospectively identify distinct progenitor- and stem cell subpopulations. This was done for the mice described above, but also in a subsequent experiment on mice transplanted with HSPC expressing a more sensitive miRNA reporter based on a destabilized GFP variant. This reporter contains a proline-glutamate-serine-threonine-rich (PEST) sequence fused to the C-terminus of GFP. The PEST motif mediates fast proteasomal degradation and rapid turnover of the protein, shortening the GFP half-life from about 26 h to 4 h (Kitsera et al., 2007). This short dGFP half-life allowed us to more accurately detect changes in miRNA expression, which possibly occur during the transit of HSC towards committed progenitors. In order to reliably determine the dGFP signal, which is lower than the standard GFP, auto-fluorescence in each individual subpopulation was subtracted from the GFP MFI by including a group of mice carrying a Bd.LV-NGFR vector which did not contain the GFP gene. The FACS plots in the following FIG. 4 were obtained from the BM of mice transplanted with the more sensitive Bd.dGFP vectors. However, the determination of miRNA activity in the mice carrying the standard GFP reporter gave very similar results, so that fold repression in FIG. 3c could be calculated on the merged data from the two independent experiments performed (Bd-ctr, n=10; Bd-223T, n=9; Bd-126T, n=13 mice).

Footprinting microRNA Activity in Murine HSPC and their Progeny

Figure 4:
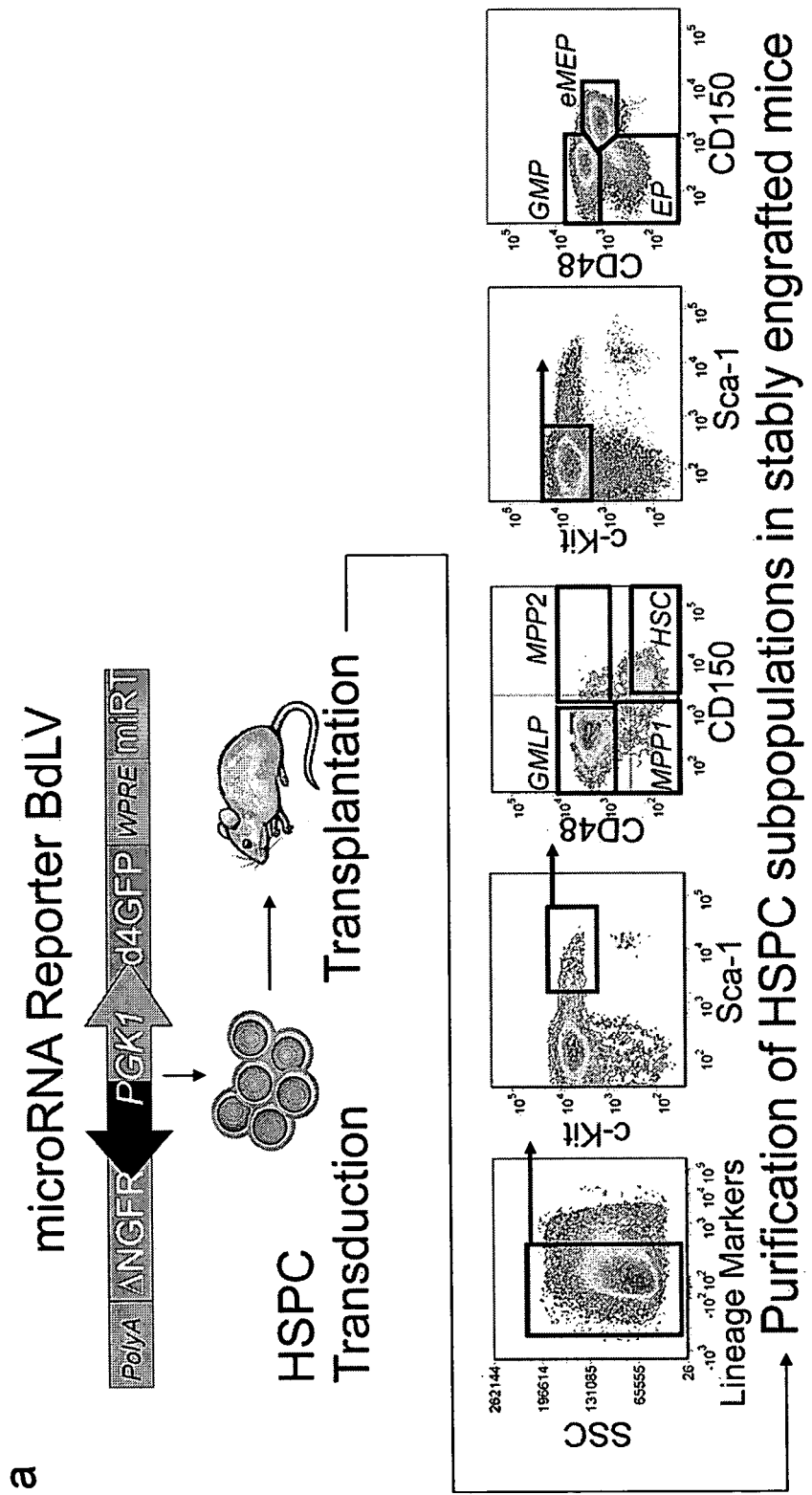
FIG. 4: (a) Lineage$^{-/low}$ bone marrow (BM) hematopoietic stem and progenitor cells (HSPC) were transduced with bidirectional miRNA reporter lentiviral vectors (BdLVs) and transplanted into lethally irradiated mice. BdLVs co-express a destabilized GFP (d4GFP) reporter made responsive to a specific miRNA by 4 tandem repeats of a perfectly complementary miRNA target (miRT) sequence, and a truncated NGFR marker gene (ΔNGFR). Mice were euthanized 8-12 weeks after transplant, and multiple BM HSPC subpopulations were prospectively identified by immunophenotyping as shown (HSC: hematopoietic stem cells; MPP: multipotent progenitors; GMLP: granulocyte-monocyte-lymphocyte progenitors; GMP: granulocyte-monocyte progenitors; eMEP: early megakaryocyte-erythrocyte progenitors; EP: erythrocyte precursors). (b) Representative FACS plots show expression of the Control-BdLV (no miRT or 133aT, a muscle-specific miRT) and reporter BdLVs for miR-126 (126T), miR-130a (130aT), miR-196b (196bT), miR-10a (10aT), miR-223 (223T), miR-19a (19aT), miR-93 (93T), miR-17-5p (17T) and let-7a (Let7aT) in HSPC subpopulations freshly isolated from the BM of transplanted mice as described in (a). Each row shows a representative pattern of reporter expression for the indicated BdLV in HSPC of the aforementioned differentiation stages. Bar graphs on the right of each row show the mean fold repression (FR)±sem calculated from reporter mean fluorescence intensities (Control: n=9; 126T: n=10; 130aT: n=4; 196bT: n=4; 10aT: n=4 except HSC and MPP1 where n=1, therefore statistics n/a; 223T: n=6, of those 5 with an eGFP reporter; 19aT: n=3; 93T: n=2; 17T: n=3; let7aT: n=1 pool of 3 mice). Statistical comparisons of miRNA activity between HSPC subpopulations were made by one way Anova and Bonferroni post test correction, using EPs of each reporter BdLV group as the reference (*: $p<0.001$; : $0.01>p>0.001$; *:$p<0.05$).
Figure 4:
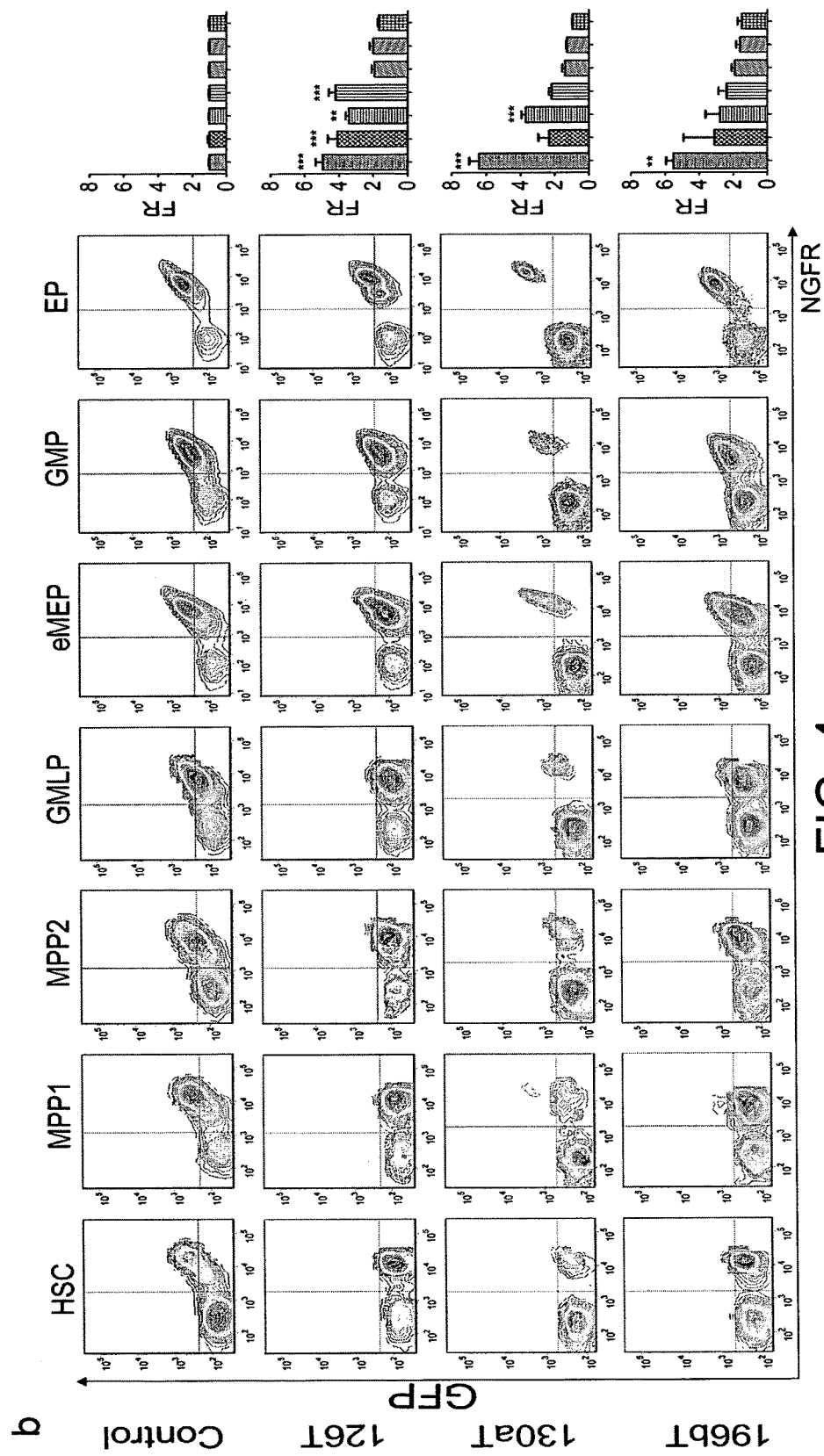
Figure 4:
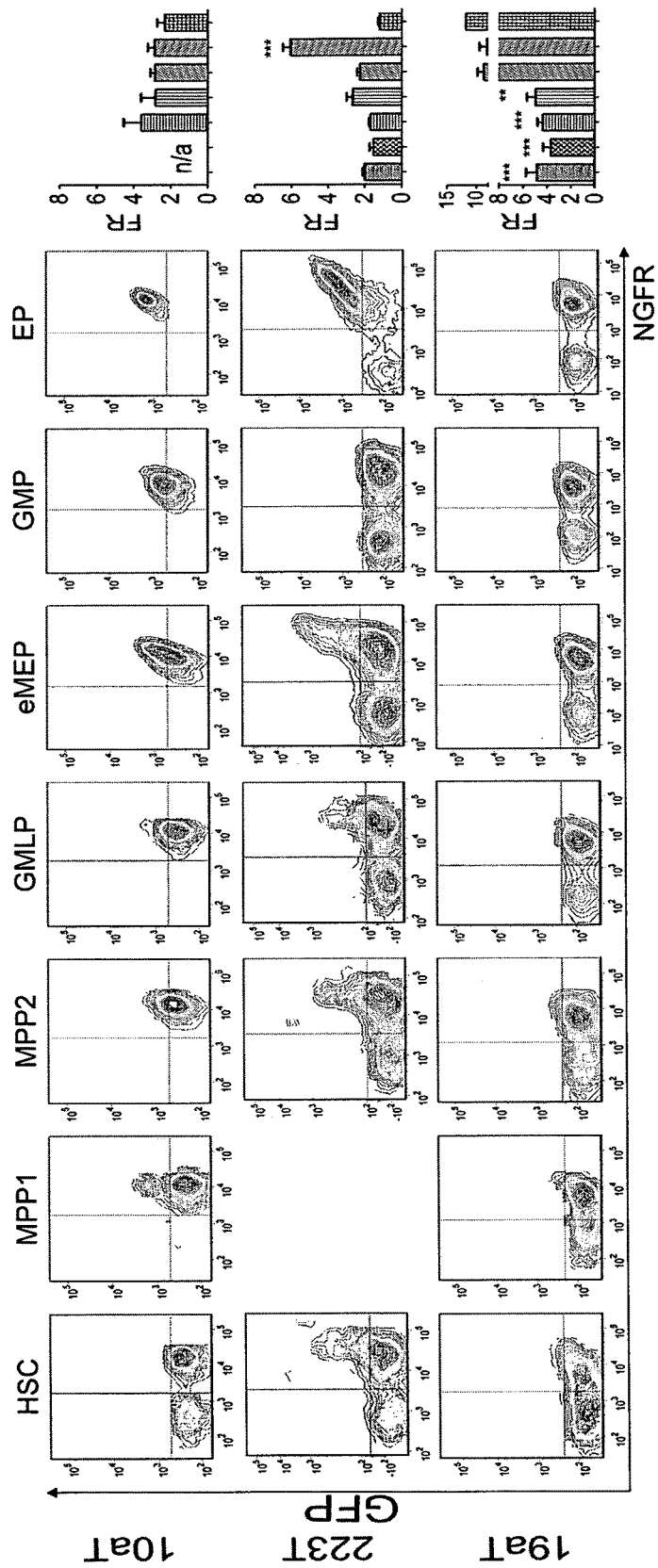
Figure 4:
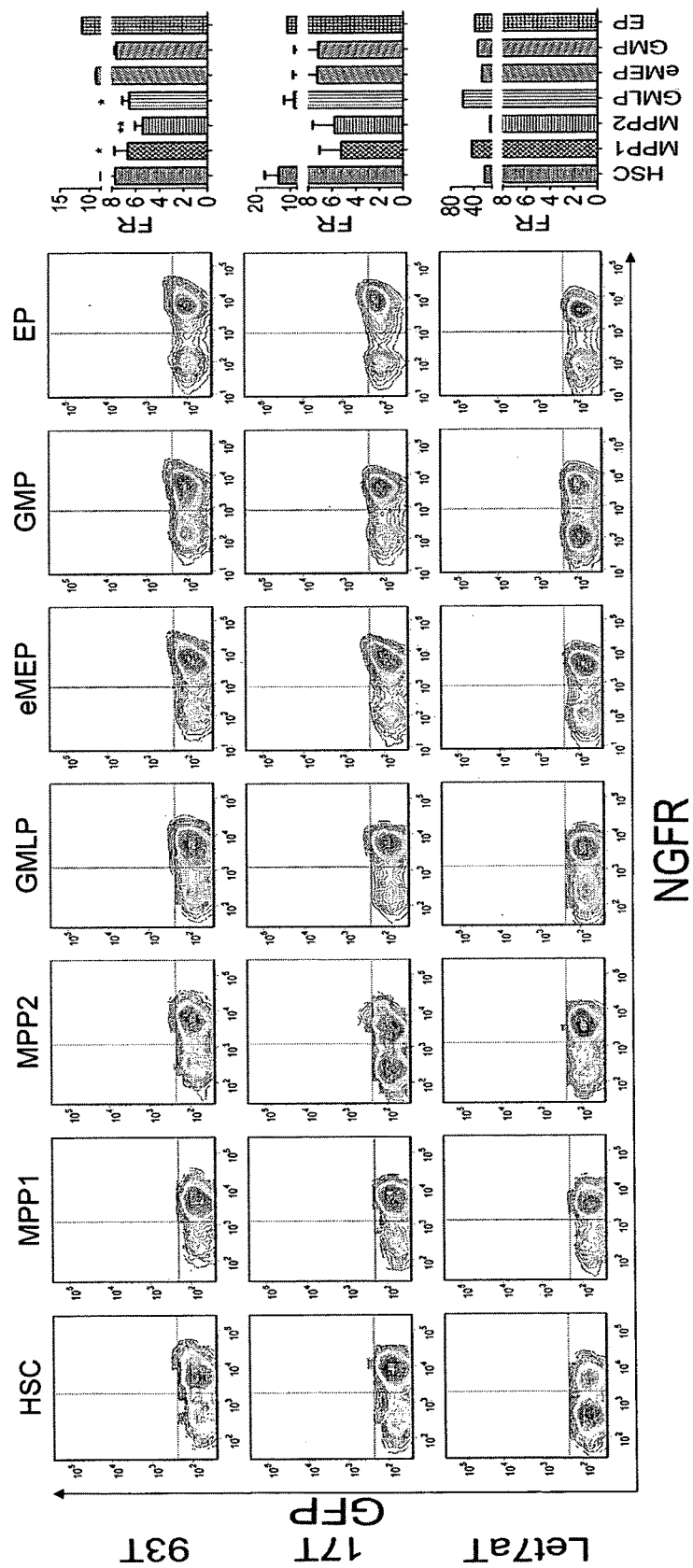

We then quantified BdLV reporter protein levels in multiple, prospectively identified hematopoietic subpopulations isolated from the reconstituted mice. The HSPC compartment was defined as bone marrow (BM) cells having a c-Kit$^{hi}$ Lineage markers$^{-/low}$ immunophenotype, and further subdivided into fractions with different self-renewal and differentiation potential based on expression of Sca-1, CD150, CD48 and CD45. Of note, 3 out of 5 cells with the immunophenotype c-Kit$^+$ Sca-1$^+$ Lin$^-$ (KSL) CD150$^{hi}$ CD48$^-$ were reported to have long-term, multilineage repopulating potential upon single cell transplantation, and thus represent bona fide HSC (Kiel M J., 2005). Moreover, based on the literature (Pronk C J., 2007) and our own findings, we subdivided Kit$^+$Sca$^-$Lineage$^-$ cells into subsets enriched for granulocyte/monocyte progenitors (GMPs) vs. megakaryocyte and erythrocyte progenitors (EP), and assessed miRNA expression. Interestingly, miR-126, miR-130a and miR-196b showed the highest activity in fractions enriched for the most primitive HSC, and this activity was lost during early stages of differentiation (FIG. 4). Importantly, miR-126, miR-130a and miR-196b are largely inactive in differentiated cells of the lymphoid and myeloid lineages, with the exception of terminally differentiated granulocytes, which seem to re-establish some degree of miR-126 activity. miR-223 was expressed in the majority of KSL cells, and in all myeloid progenitors (GMPs), but was sharply down-regulated in EPs. As expected, miR-223 was progressively upregulated during myeloid differentiation, while B- and T-lymphocytes were devoid of it (FIG. 5a). Also, members of the miR-17-92 cluster (miR-19, miR-93a, miR-17-5p) resulted highly expressed in HSPC. However, their suppressive activity was maintained during further differentiation, and decreased to some degree only in terminally differentiated B cells and granulocytes (FIG. 5a). Finally, let-7a retained substantial suppressive activity in all hematopoietic cell types, including bona fide HSC, consistent with its ubiquitous expression pattern.

Protection of HSC from Conditional Suicide by miR-126

Figure 6:
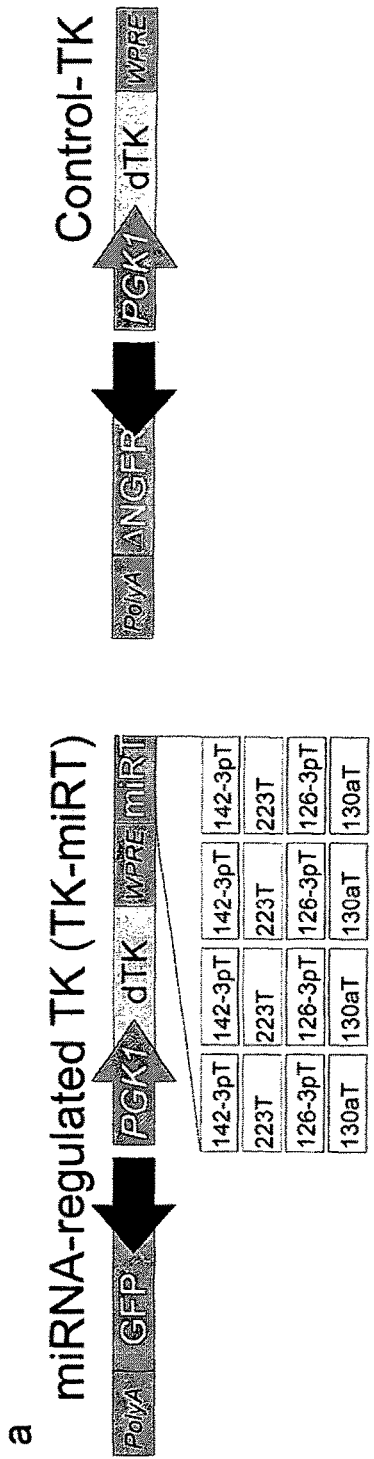
FIG. 6: Regulating the expression of a suicide gene by miRNA target sequences. (a) miRT sequences perfectly complementary to miR-142, miR-223, miR-126, or miR-130a were added to a destabilized thymidine kinase (dTK) transcript. Monodirectional lentiviral suicide vectors (right half of each vector drawing) were used for (b), while bidirectional suicide vectors coupling a GFP marker to the miRNA-regulated TK, or an NGFR marker to the Control-TK were used in (c). (b) Lineage–/low HSPC were transduced with the indicated lentiviral vectors, and plated +/– gancyclovir (GCV) in semisolid medium (LV-GFP: n=2; CTRL-TK: n=8; TK-142T: n=4; TK-223T: n=6; TK-126T: n=4; TK-130aT: n=2). After 10d, the number of myeloid (CFU-GM, CFU-G, CFU-GM) and erythroid (BFU-E, CFU-E) colonies was counted. Box and whiskers plots show the colony number in the cultures containing GCV divided by the colony count in respective control cultures without GCV (10th-90th percentile). The 'no GCV' data point shows plating variability (colony count of each non-GCV treated culture divided by the mean colony count of all non-GCV treated cultures; n=26). Statistical comparisons were made against the GCV-treated, LV-GFP group; ns, not significantly different; , $0.001<p<0.01$: *, $p<0.001$. (c) Lineage–/low HSPC from CD45.1+ mice were transduced either with a TK control vector (NGFR-marked) or a miRNA-regulated TK vector (GFP-marked; Exp#1: TK.126T; Exp#2: TK.142T), LV.NGFR/Control TK- and LV.GFP/TK-miRT-transduced cells were mixed in a 1:1 ratio and transplanted into CD45.2+ congenic mice which were treated with GCV (Exp#1: n=6 mice; Exp#2: n=5 mice) for 7-14d starting at day 3 post-transplant, or left untreated (Exp#1: n=4; Exp#2: n=3). Representative FACS plots show GFP/NGFR chimerism within CD45.1+ donor cells. Graphs show the fraction of GFP-expressing cells within the transduced, donor-derived cells in the blood for the GCV treated (red) and untreated (black) mice, for each blood cell type over a 7-8 month time period. Note that significantly more cells are GFP-F in the GCV group (***: $p<0.001$, 2-way Anova), indicating protection from suicide and selective advantage of HSC transduced by GFP/TK.126T or GFP/TK.142T. Thus, the miR-126T sequence added to a transgene overcomes HSPC toxicity arising from highly toxic transgenes even when expressed from ubiquitous promoters, carrying significant potential to improve the safety and efficacy of HSPC-based gene therapy. Furthermore, these results formally prove that miR-126 is active in long-term engrafting hematopoietic stem cells as demonstrated by a functional repopulation assay.
Figure 6:
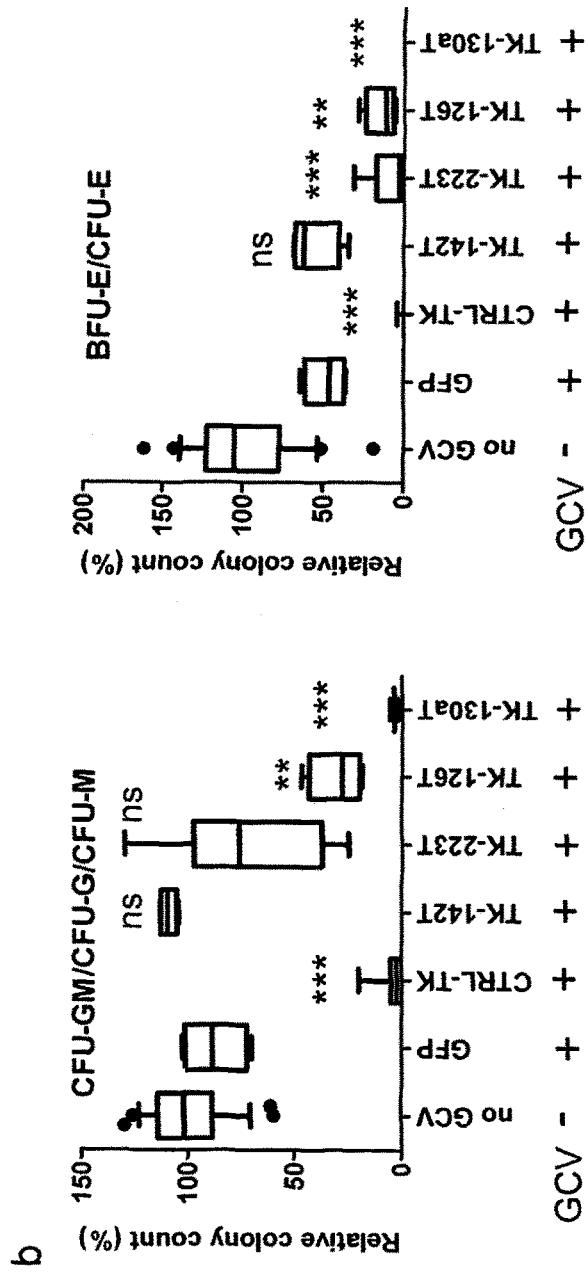
Figure 6:
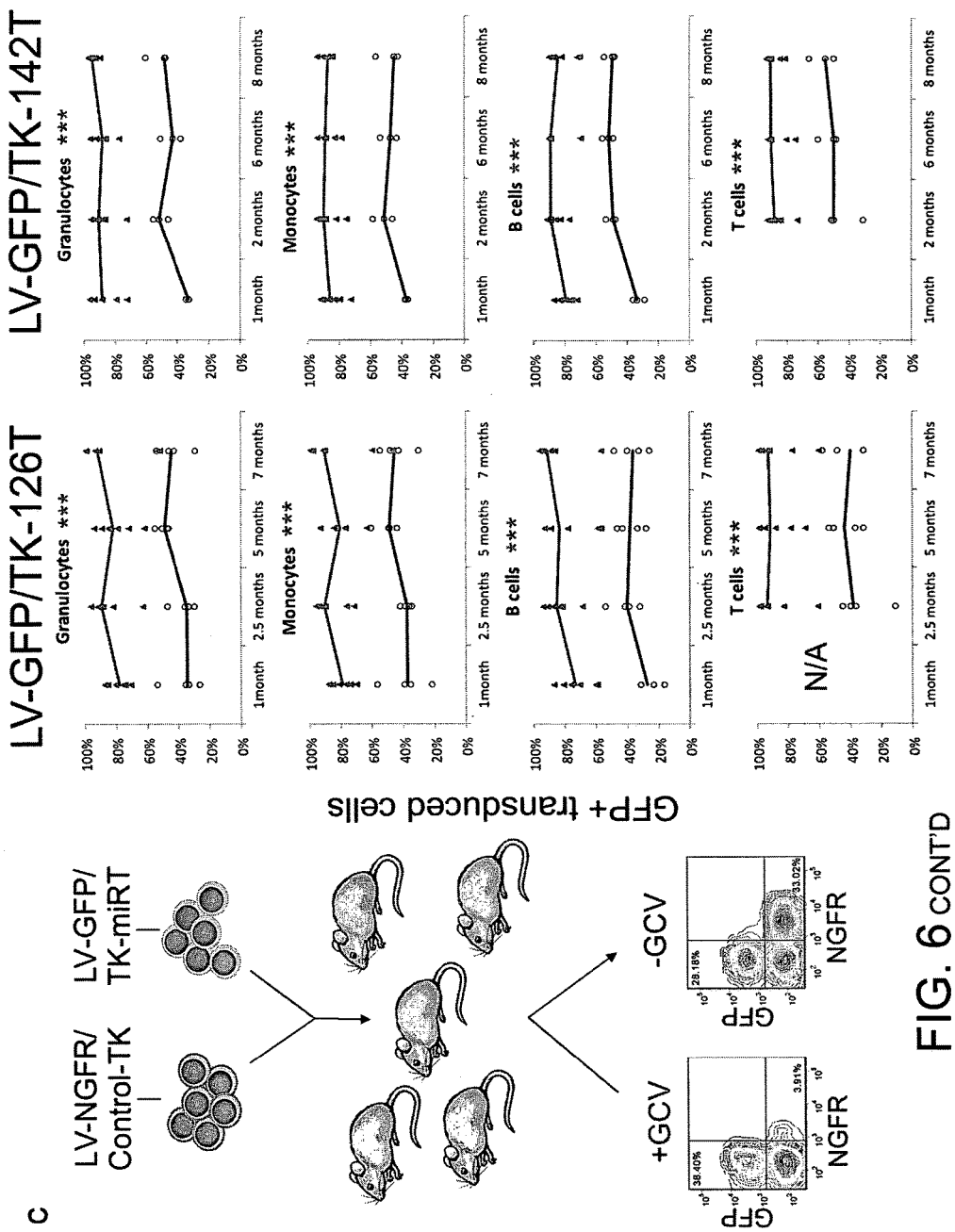

The aforementioned miRNA activity footprints were based on prospective isolation of hematopoietic cell populations according to immunophenotype. In order to conclusively establish the activity of selected miRNAs in functionally defined cell subsets, we devised a conditional suicide system based on lentiviral vectors expressing the herpes simplex virus thymidine kinase (TK) gene regulated by different miRT sequences (FIG. 6a). As TK is very stable with a half-life of ~35 hours, we destabilized the TK protein (now called dTK) by fusing the PEST domain of d4GFP to the C-terminus of TK. HSPC were transduced with one of the indicated suicide vectors or a GFP control vector, and were plated in semisolid medium, either in the presence or absence of GCV (FIG. 6b). HSPC transduced with the control TK vector did not give rise to colonies in the presence of GCV. Adding miR-142T sequences to the dTK transcript completely rescued colony formation, in line with the pan-hematopoietic expression of this miRNA (Brown B D., 2006). Instead, miR-223T at least partially restored the growth of myeloid colonies, while erythroid colony number was significantly reduced (p<0.001) and did not differ statistically from control TK-transduced cells. A partial rescue of myeloid colonies was also obtained with the miR-126T, although to a lower level than that obtained with miR-223T. GCV fully prevented the growth of both myeloid and erythroid colonies in the miR-130aT groups, in line with the sharp down-regulation of mir-130a during early steps of differentiation.

We then developed an in vivo suicide assay to demonstrate miRNA activity in functionally defined HSC. The TK/GCV suicide system requires cell division in order to become toxic. Pilot experiments co-transplanting TK-transduced cells with untransduced BM supporting cells indicated that a 1-week time course of GCV given within the first 2 weeks of engraftment efficiently eliminates TK-transduced long-term repopulating HSC (data not shown). We then transduced HSPC with either a miRNA-regulated bidirectional suicide vector expressing dTK-126T or dTK-142T and GFP, or a control bidirectional suicide vector expressing dTK and ΔNGFR. Cells transduced with the control or one of the miRNA-regulated suicide vectors were then co-transplanted into congenic mice, which did or did not receive GCV during the engraftment phase (FIG. 6c). Long-term analysis of peripheral blood chimerism indicated that most of the NGFR$^+$ cells were efficiently eliminated in GCV-treated mice, while GFP$^+$ cells persisted in increased relative numbers. This was observed in multiple lineages (granulocytes, monocytes, B- and T lymphocytes) and over a >7 month time period, for both dTK-126T- and dTK-142T-transduced cells. These data establish that both miR-126 and miR-142 are expressed in long-term repopulating HSC to sufficient levels to prevent TK protein expression and cell death induced by GCV.

Safety of Exploiting miR-126 Regulation for Gene Therapy

Figure 7:
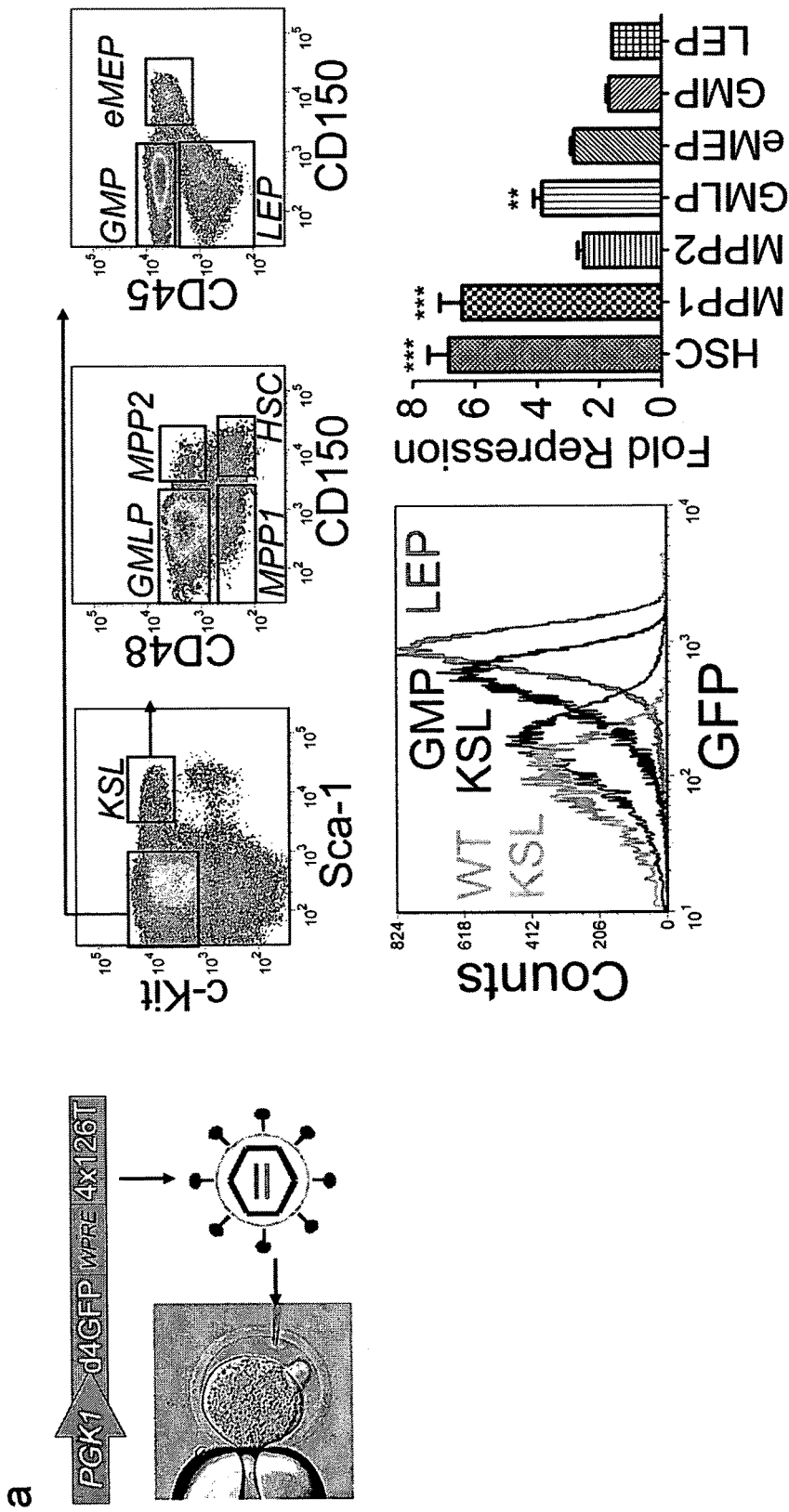
FIG. 7: (a) To address the safety of exploiting miR-126 regulation for gene therapy, a transgenic mouse line containing a miR-126 reporter (Tg.126T) was created by microinjection of the illustrated LV into the perivitelline space of zygotes. FACS analysis of the bone marrow of young, adult transgenic mice demonstrated that GFP expression was lowest in Kit$^+$Sca$^+$Lineage marker$^-$ (KSL) cells (blue graph in histogram plot), while GFP expression switched on in Kit$^+$Sca$^-$Lin$^-$ progenitors (black and red graph in histogram plot). GFP MFI of Tg.126T mice and control GFP transgenic mice was measured to calculate the FR of the miR-126 reporter in the indicated HSPC subpopulations (mean±sem, n=10 Tg.126T mice; *: $p<0.001$; : $0.01>p>0.001$ as compared to EP). (b) Whereas mice carrying two knockout alleles for miR-126 manifest significant embryonic lethality due to angiogenic defects, breeding our Tg.126T colony resulted in normal litter size and an expected vector copy number (VCN) distribution in the offspring reflecting the one of the parental generation, suggesting that moderate expression of miR-126T sequences from a PGK promoter did not interfere with the regulation of natural miR-126 targets during development. (c) BM cells from CD45.2$^+$ Tg126T mice and CD45.1$^+$ wild-type (WT) mice were enriched for HSPC by positive selection for CD117 and competitively transplanted (1:1 ratio) into lethally irradiated CD45.2$^+$ recipients (n=4). Transplanted mice were bled in regular intervals, and CD45.1/CD45.2 chimerism was determined in the various peripheral blood cell lineages (Granu: CD11b$^+$side scatter$^{hi}$; Mono: CD11b$^+$side scatter$^{low}$; B cells: CD19$^+$; T cells: CD3$^+$). These data indicate that there is a comfortable therapeutic window for safely exploiting miR-126 regulation.
Figure 7:
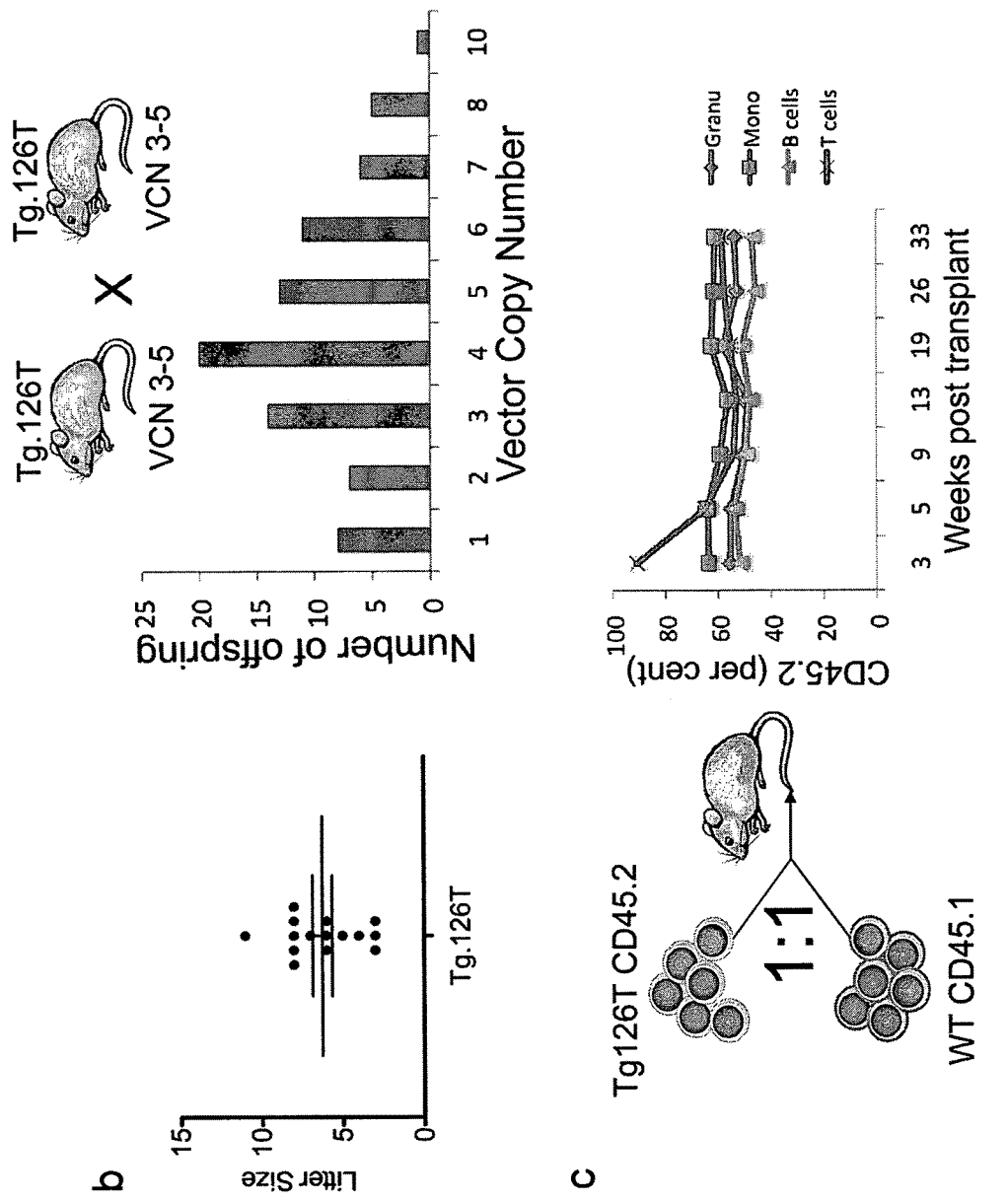

We then derived a transgenic mouse line (Tg.126T mice) which harbors germline integrations of a lentiviral vector expressing a d4GFP.126T transcript from the same promoter used in the BdLV studies described above. FACS analysis of Lin$^-$BM cells of young adult Tg.126T mice showed a similar pattern of miR-126 activity as observed in the transplanted mice (FIG. 7a). This confirms that miR-126 is physiologically expressed in HSC. miR-126 is known to be expressed in endothelial cells, and loss-of-function during development resulted in fetal mortality due to defective angiogenesis (Fish J E., 2008). No gross phenotypic abnormalities were present in Tg.126T mice. When Tg.126 mice were intercrossed, litters of normal size that maintained the average number of vector integrants of their parents were obtained (FIG. 7b). This data indicates that expression of the miR-126T sequences from the phosphoglycerate kinase 1 (PGK) promoter did not interfere with mouse development, and argues against the hypothesis that miR-126T expression could interfere with the regulation of natural miR-126 targets in endothelial cells under these circumstances. To further rule out this latter issue in hematopoietic cells, we set up a competitive repopulation experiment. CD45.1$^+$ HSPC were co-injected with equal numbers of CD45.2$^+$ HSPC from Tg.126T mice into lethally irradiated CD45.1$^+$ recipients. Peripheral blood chimerism was stable and maintained for at least 1 year (latest time of analysis) at around 40-50% CD45.2$^+$ cells (n=4) for all major blood lineages (FIG. 7c). Together, these data indicate that miR-126 is expressed in primitive HSC and the biosensor approach provides a powerful, non-toxic means to identify hematopoietic cells at the single cell level on the basis of miRNA expression.

Characterization of Candidate miRNA Activity in Human Hematopoietic Cells

Figure 8:
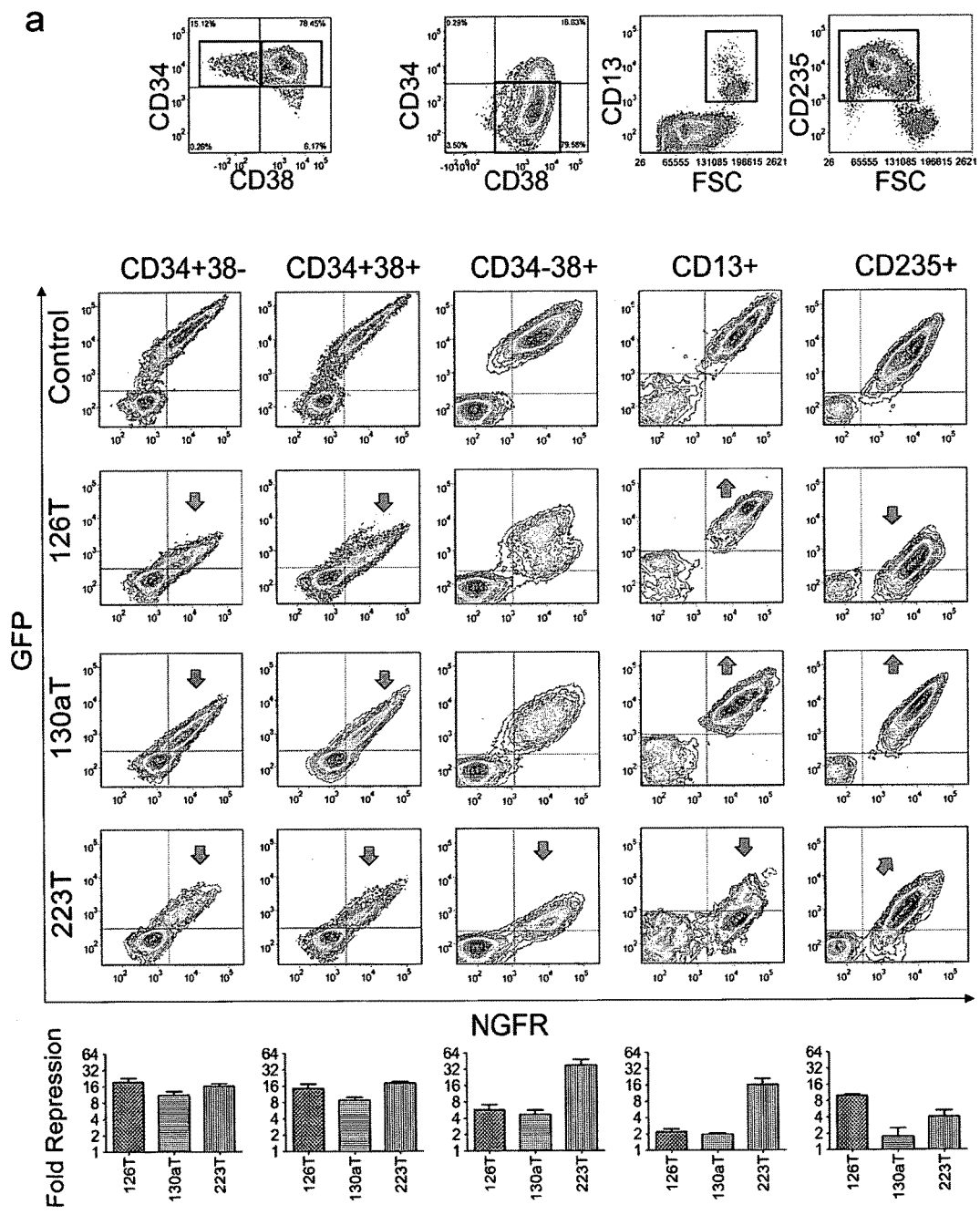
FIG. 8: (A) CD34$^+$ HSPC were purified from human cord blood (CB) and transduced with the Control-BdLV (Control) or miRNA reporter BdLVs for miR-126 (126T), miR-130a (130aT) or miR-223 (223T) (n=3 biological replicates per group). Cells were kept in liquid culture under conditions supporting the short-term maintenance of HSPC, and BdLV marker expression was measured 2 days post transduction in CD34$^+$CD38$^-$ HSPC and CD34$^+$CD38$^+$ progenitors (first 2 columns on the left). Cells were then differentiated, either in liquid culture for 6 days (CD34$^-$ CD38$^+$ cells; middle column), or in semisolid medium for 16 days (CD13$^+$ myeloid cells, CD235$^+$ erythroid cells). Representative FACS plots are shown. Bar graphs on the bottom show quantification of miR-126, miR-130a and miR-223 activity in the respective subpopulations (n=3; mean fold repression +/- sem; , 0.001<p<0.01: *, p<0.001). (B) Cord blood CD34$^+$ cells were transduced with control- or miRNA regulated bidirectional suicide vectors containing miRNA target sequences for miR-223 (TK-223T) or miR-126 (TK-126T, see also FIG. 2), and plated in CFC assays in quadruplicate, either in the presence or the absence of the pro-drug GCV. The number of GFP$^+$ erythroid (CFU-E, BFU-E) or myeloid (CFU-G, CFU-M, CFU-GM) colonies was counted 14 days after plating, and normalized to the number counted in the 'no GCV' culture. Box and whiskers plots show 10$^{th}$-90$^{th}$ percentile. GCV completely prevented growth of CTR-TK transduced colonies. (C) Combinations of miR-126T and miR-130aT sequences (4+4 and 2+2 tandem repeats, respectively), as well as 2 tandem repeats of miR-126T alone were compared to the standard miRT design utilizing 4 tandem repeats of miR-126T or miR-130aT, respectively. Human cord blood cells were transduced with the respective reporter BdLVs, and fold repression of the reporter was determined in the primitive stem/progenitor compartment (CD34+CD38−) and the progenitor compartment (CD34+CD38+) 2 days post transduction, as well as in the myeloid progeny (CD13+) and erythroid progeny (CD235+) 10-14 days post transduction. 126T (4 targets), 126T/130aT (4+4 targets) and 126T/130aT (2+2 targets) suppress equally well in the stem/progenitor compartment. However, 126T/130aT (4+4 targets) has a higher background suppressive activity in the myeloid progeny. (D) Suppressive activity of 126T (4 targets), 126T/130aT (2+2 targets) and 126T (2 targets) in the primitive compartment (as in C), and in late myeloid differentiation stages (myelocytes: CD11b+/CD16−; metamyelocytes: CD11b+/CD16+/SSClow; granulocytes: CD11b+/CD16+/SSChigh) upon G-CSF induced in vitro differentiation. Differentiation stages were verified on May-Grünwald/Giemsa stained cytospin samples from the culture. The regulation index (right graph) is calculated by dividing the fold repression of the respective miRT in the CD34+/CD38− stem/multipotent compartment by the fold repression in metamyelocytes. The best "release" of transgene expression in the myeloid progeny is obtained by 126T (2 targets), while suppression in the stem/progenitor compartment is—similar to 130aT (4 targets)—slightly less compared to 126T (4 targets) and 126T/130aT (2+2 targets). Regarding the latter 2 target sequences, 126T/130aT (2+2 targets) is preferable over 126T (4 targets), as it offers the biggest regulation index. Furthermore, transgene downregulation is assured by 2 independent miR-NAs, and the risk of interfering with endogenous miRNA regulation is further reduced, thus increasing safety and efficacy of the miRT.
Figure 8:
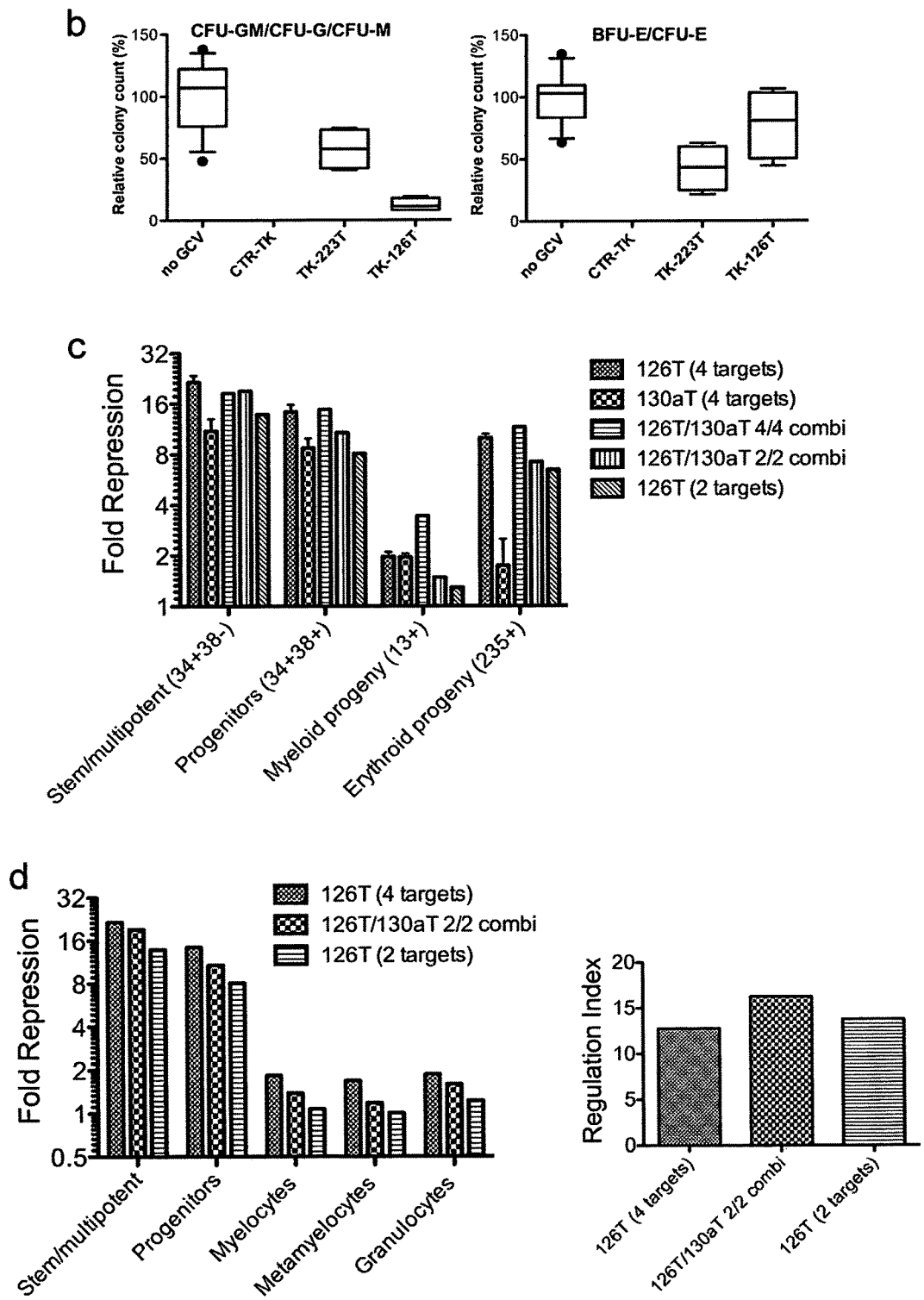

Our characterization of miR-223, miR-130a and miR-126 activity in the murine hematopoietic system proposed these miRNAs as promising endogenous regulators for limiting transgene toxicity in HSPC while allowing therapeutic expression in differentiated myeloid and lymphoid cells. We next sought to investigate the activity of these miRNAs in human hematopoietic cells, which are the actual targets for gene therapy. We transduced human CB CD34$^+$ cells with reporter Bd.LVs for miR-126, miR-130a, miR-223 (FIG. 8A). Cells were cultured in vitro under conditions which provide support for short-term maintenance of HSPC, and subpopulations based on CD34/CD38 expression were identified by flow cytometry. Myeloid (CD13$^+$) and erythroid (CD235$^+$) differentiation was assessed using the methylcellulose assay. miR-126, miR-130a and miR-223 all suppressed their respective reporter transcripts in the CD34$^+$ HSPC population. Upon differentiation, miR-223 maintained activity in the myeloid lineage, while it decreased during erythroid differentiation. On the contrary, miR-126 lost its activity during myeloid differentiation but maintained it in the erythroid progeny. These patterns of expression were functionally verified by conditional suicide assay (FIG. 8b). miR-130a lost its activity in both the myeloid and erythroid lineages. Quantification of miRNA activity in the respective populations (FIG. 8A) indicated that, among the miRNAs tested, miR-126 was the most potent miRNA in the CD34$^+$CD38$^-$ CB fractions enriched for primitive HSPC. FIG. 8c/d shows a further optimization of the miRT sequence by combining miR-126T and miR-130aT sequences.

Example 2

Forced GALC Expression in HSPC

Figure 9:
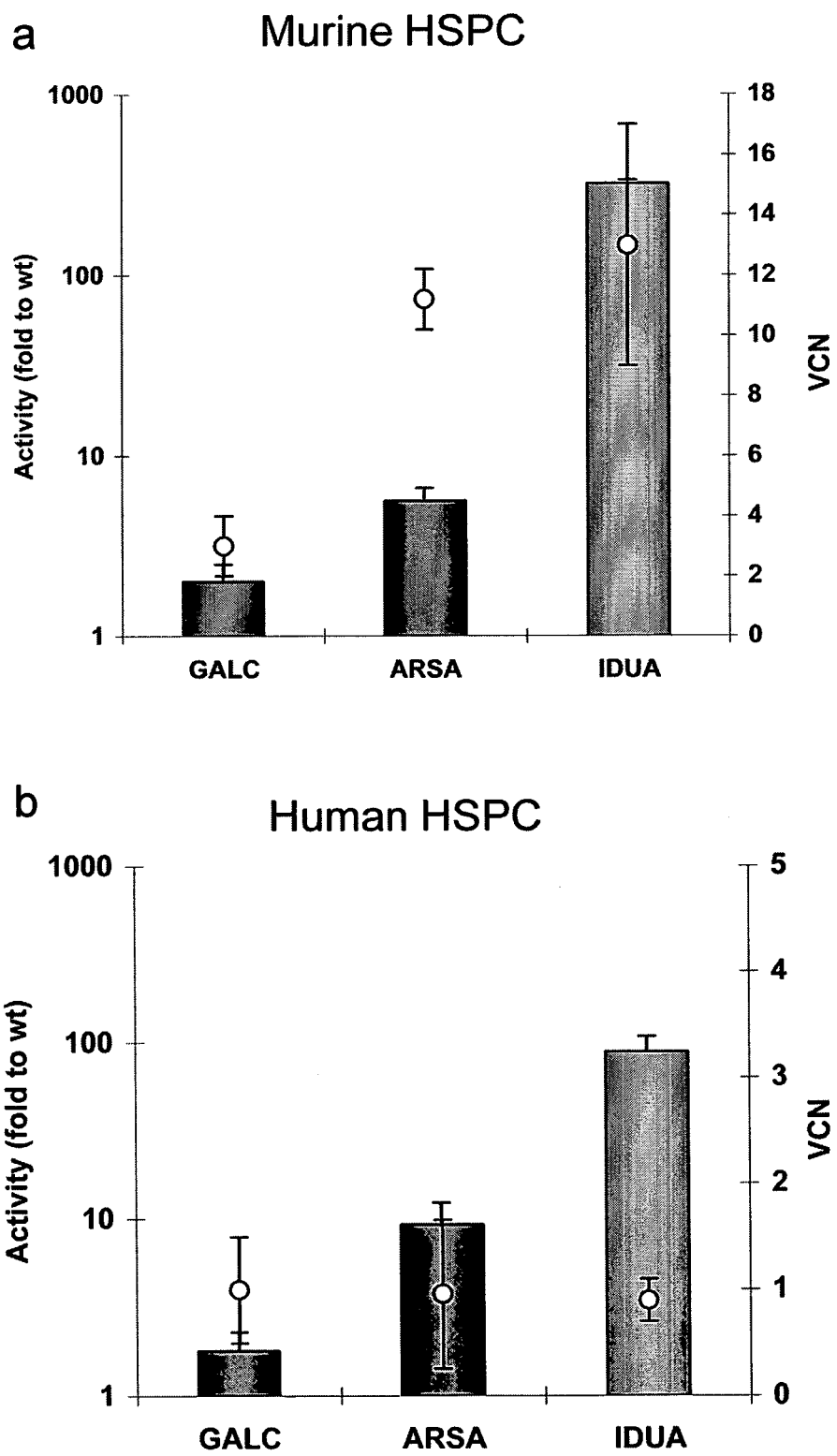
FIG. 9. Lysosomal enzyme over-expression in HSPC. Enzyme expression level, normalized to wild type, in mHSPC (A) and hHSPC (B) upon LV transduction. GALC expression was significantly lower as compared to ARSA and IDUA.

In order to assess the feasibility of GALC over-expression in murine HSPC (mHSPC), we isolated Lin-cells from FVB/twi (GALC −/−) mice. mHSPC were transduced at MOI 100 with GALC.LV in the presence of an optimized cytokine combination (Biffi et al., 2004). After transduction, cells were cultured 10-14 days in vitro to assess enzymatic activity and the vector copy number (VCN) by Q-PCR. We compared the expression level of GALC with the over-expression of other lysosomal enzymes, Arylsulfatase A (ARSA) and -Iduronidase (IDUA), obtained by transducing mHSPC with the control vectors ARSA.LV and IDUA.LV. All vectors expressed the transgene from the same expression cassette containing the human PGK promoter. Since our aim was to compare the enzyme over-expression in transduced −/−HSPC with respect to physiological enzyme levels in wild type HSPC, mHSPC obtained from ARSA KO mice and from IDUA KO mice were used for ARSA.LV and IDUA.LV transduction, respectively. Transduction of mHSPC reconstituted lysosomal enzyme activity in −/− cells and led to enzyme over-expression with respect to wild type levels in the cultured progeny of transduced −/− mHSPC (FIG. 9A). However, the increase in GALC expression (2 fold above wild type) was significantly lower as compared to the increase in IDUA and ARSA obtained by IDUA.LV and ARSA.LV controls (320 and 5.6 fold over wild type, respectively), despite similar VCN.

A similar experiment was performed on human HSPC (hHSPC), isolated through CD34+ selection from CB obtained from normal donors (n.d.). hHSPC were transduced at MOI 100 with GALC.LV, ARSA.LV and IDUA.LV, using previously optimized transduction protocols 105. Similarly to mHSPC, we evaluated enzyme activity reconstitution and VCN upon in vitro culture of the transduced cells. GALC.LV transduction of HSPC from n.d. CB (n=4) led to limited over-expression of the enzyme in the cultured cell progeny as compared to IDUA.LV (n=3) and ARSA.LV (n=6) controls (FIG. 9B).

Figure 10:
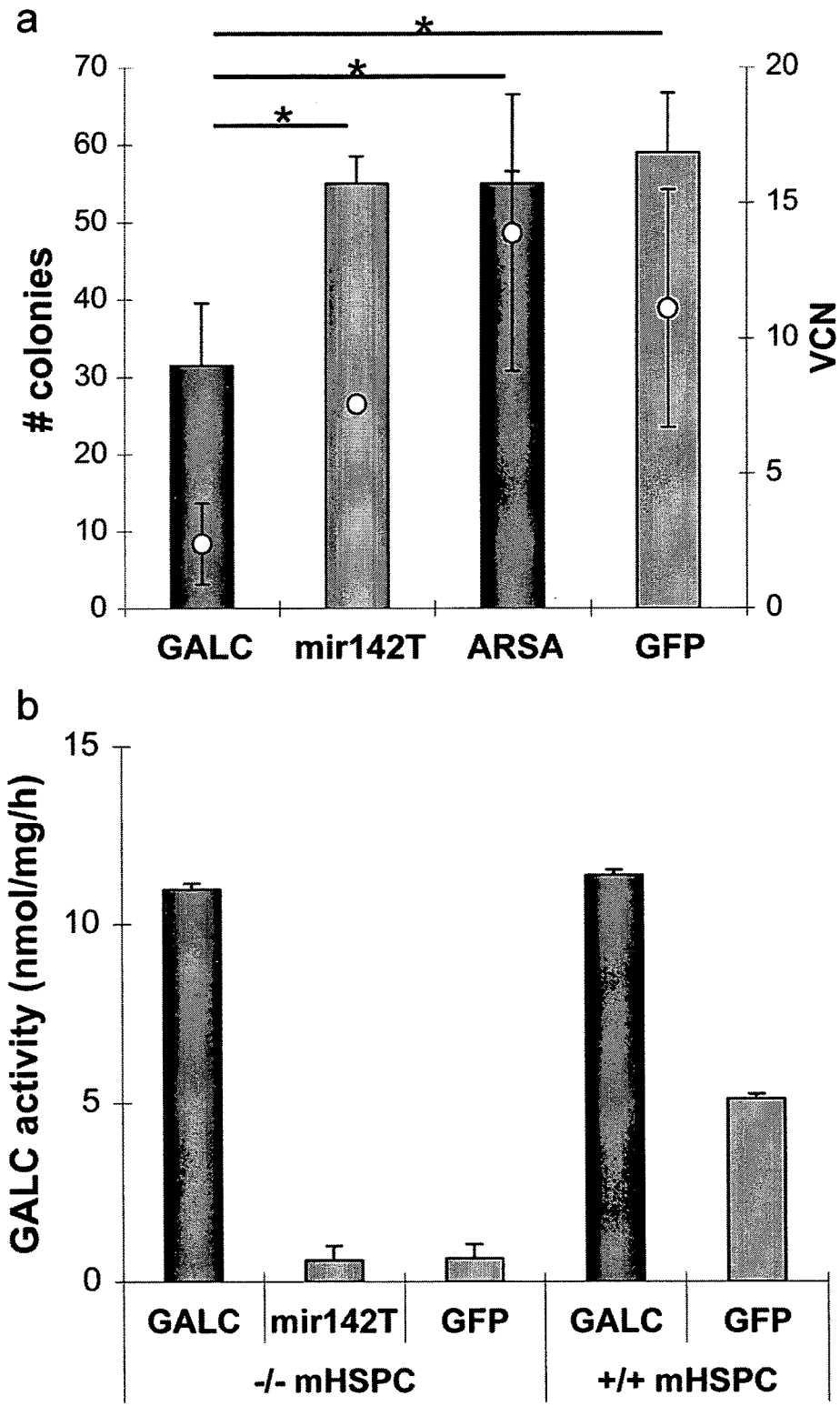
FIG. 10. Impaired function of murine HSPC upon LV-mediated GALC expression. (A) CFC assay on mHSPC transduced with GALC and control LV. The number (#) of colonies/plate (Y left axis, columns) was counted and the number of integrated LV copies/cell (VCN)(Y right axis, dots) was measured. GALC.LV transduced −/− mHSPC (n=12 independent experiments) produced a significantly lower number of colonies as compared to GFP.LV (n=10) and ARSA.LV (n=8) transduced cells. This impairment was not observed when mHSPC were transduced with the mir142T GALC.LV (n=6). *p<0.OO1 at one-Way Anova for both number of colonies/plate and VCN. Mean values±SD are shown. Similar results were obtained with −/− and +/+ mHSPC. (B) GALC activity measured on transduced mHSPC. After GALC.LV transduction GALC −/− (hereon −/−) (n=5) and GALC+/+(hereon+/+) (n=5) mHSPC showed a 2 fold increase in GALC activity above wild type levels (+/+ mHSPC transduced with GFP.LV, n=5). No increase in activity was detected in mHSPC transduced with a mir142 regulated GALC.LV (mir142T) (n=3).

Impaired In Vitro Function of GALC Expressing HSPC Upon LV-Mediated GALC Expression The effects of transduction and enzyme expression on mHSPC clonogenic potential were assessed by CFC assay. Equal number of GALC/GFP/ARSA.LV transduced mHSPC were seeded for colony assay. ARSA was chosen as control lysosomal enzyme since it was previously shown to not affect HSPC function (Capontondo et al., 2007). In 12 independent experiments GALC.LV transduced –/– and +/+ mHSPC gave rise to a significantly reduced number of colonies as compared to GFP.LV and ARSA.LV transduced cells (FIG. 10A for GALC –/– cells). Colonies from GALC.LV transduced mHSPC were of markedly reduced size as compared to controls (FIG. 24B). These results suggested that GALC over-expression upon LV transduction impaired mHSPC clonogenic potential. The relative proportion of erythroid and myeloid colonies upon GALC.LV transduction was similar to controls (not shown), suggesting that enzyme expression impaired the different hematopoietic lineages to the same extent.

The reduced clonogenic potential of GALC.LV transduced mHSPC could result from the death of highly transduced GALC over-expressing hematopoietic progenitors. In order to investigate the possible occurrence of an negative selection of highly transduced mHSPC, we quantified the VCN of colonies by Q-PCR. Q-PCR was performed on DNA extracted from each pool of 4 colonies (pools were made in order to have a sufficient amount of material for the analysis). Colonies obtained from GALC.LV transduced mHSPC showed a significantly lower vector content when compared to controls (FIG. 10A), suggesting the occurrence of negative selection of highly transduced progenitors.

According to these data, we could not discriminate whether functional impairment and in vitro selection were due to a toxic effect of transduction or to the presence of contaminants released by vector-producer cells and co-purified with the vector. It must be mentioned that, during GALC.LV production, 293T cells detach from plates, suggesting that GALC expression is toxic also to these cells. For this reason, the incorporation of toxic molecules deriving from dead 293T cells into the vector preparation could not be excluded. To address this issue, we generated a control vector regulated by an hematopoietic-specific microRNA, GALCmir142T.LV 56. Four target sequences for the microRNA 142 incorporated downstream the transgene allow to suppress expression in mHSPC and in their progeny without impairing GALC expression in non-hematopoietic cells, such as 293T LV-producing cells. This technology is based on microRNA post-transcriptional regulation: microRNA 142, expressed only by hematopoietic cells, recognizes its target sequence downstream the transgene and inhibits the translation of the transcript and expression of the transgene. As expected, transduction of mHSPC with GALCmir142T.LV was not associated to an increase of GALC activity (FIG. 10B). Moreover, mHSPC transduced with GALCmir142T.LV (n=6) showed unaffected clonogenic potential and similar vector content as compared to controls, thus confirming the previously observed impairment being dependent on GALC expression (FIG. 10A).

Figure 11:
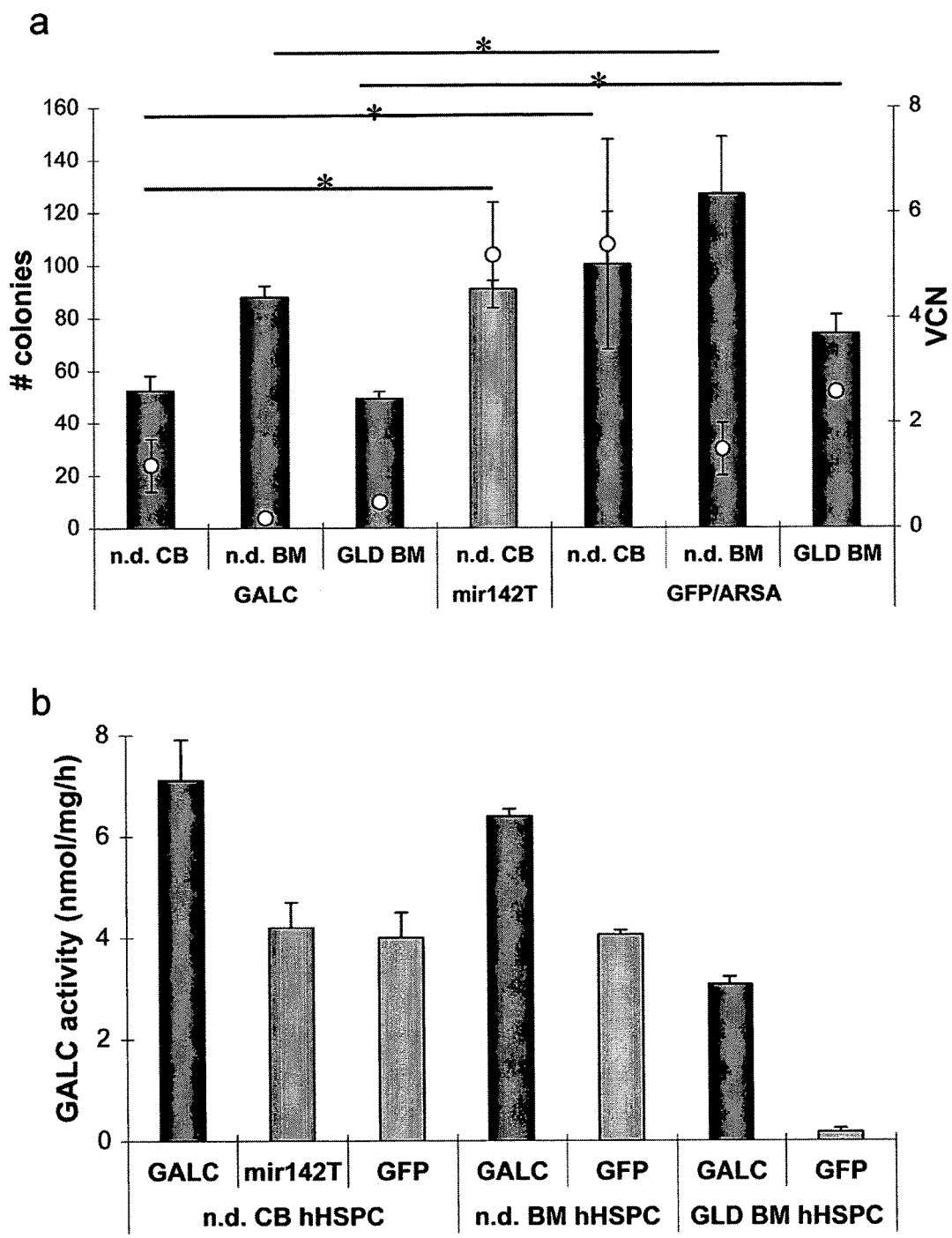
FIG. 11. Impaired function of human HSPC upon LV-mediated GALC expression. (A) CFC assay on hHSPC transduced with GALC and control LV. The number (#) of colonies/plate (Y left axis, columns) was counted and the number of integrated LV copies/cell (VCN)(Y right axis, dots) was measured. GALC.LV transduced n.d. (n=4) and GLD hHSPC (n=4) showed a significant impairment in colony formation as compared to control cells (n=5), which was not observed following mir142T GALC.LV transduction (n=4). Colonies obtained from GALC.LV transduced hHSPC showed a significantly lower vector content, when compared to GFP/ARSA/GALCmir142T.LV controls. *p<0.001 at One-Way Anova for both number of colonies/plate and VCN. Mean values±SD are shown. (B) GALC activity measured on transduced hHSPC. GALC.LV transduction permitted the reconstitution of GALC activity at n.d. levels in GLD hHSPC (n=3), while transduction of n.d. hHSPC (n=4 for CB and n=3 for BM) led to over-expression of the enzyme above GFP.LV transduced levels (n=3). No increase in activity was detected in hHSPC transduced with a mir142 regulated GALC.LV (mir142T) (n=3).

We investigated the effect of GALC over-expression also on human HSPC. hHSPC were isolated from n.d. CB and BM and from the collected BM of a GLD patient that was scheduled to be discarded. An equal number of hHSPC were transduced with GALC.LV or ARSA.LV or GFP.LV control vectors were seeded for CFC assay, in order to assess the clonogenic potential of transduced hHSPC. As in the case of murine cells, GALC.LV transduced n.d. and GLD hHSPC showed an impaired clonogenic potential (FIG. 11A). Colonies from GALC.LV transduced hHSPC showed a significantly lower vector content, when compared to controls, a reduced size and conserved erythroid-myeloid proportion, again suggesting negative selection of the highly transduced progenitors (FIG. 11A). Also in this case, the control vector GALCmir142T.LV was used to rule out an aspecific toxic effect of transduction. As in the case of murine cells, GALCmir142T.LV transduced hHSPC (n =4) showed GALC activity and clonogenic potential similar to those observed in control cells (FIGS. 11A and B).

Overall these data indicate that forced GALC de novo expression upon LV transduction exerts a detrimental effect both on murine and human HSPC, leading to negative selection of GALC over-expressing cells and to functional impairment.

Impaired in vivo function of HSPC upon LV-mediated GALC expression We performed in vivo experiments with the aim of assessing the repopulation potential of m- and hHSPC upon GALC.LV transduction and GALC de novo expression. In vivo studies were performed on twi and FVB/twi mice for mHSPC, and on Rag2c mice for hHSPC.

Figure 12:
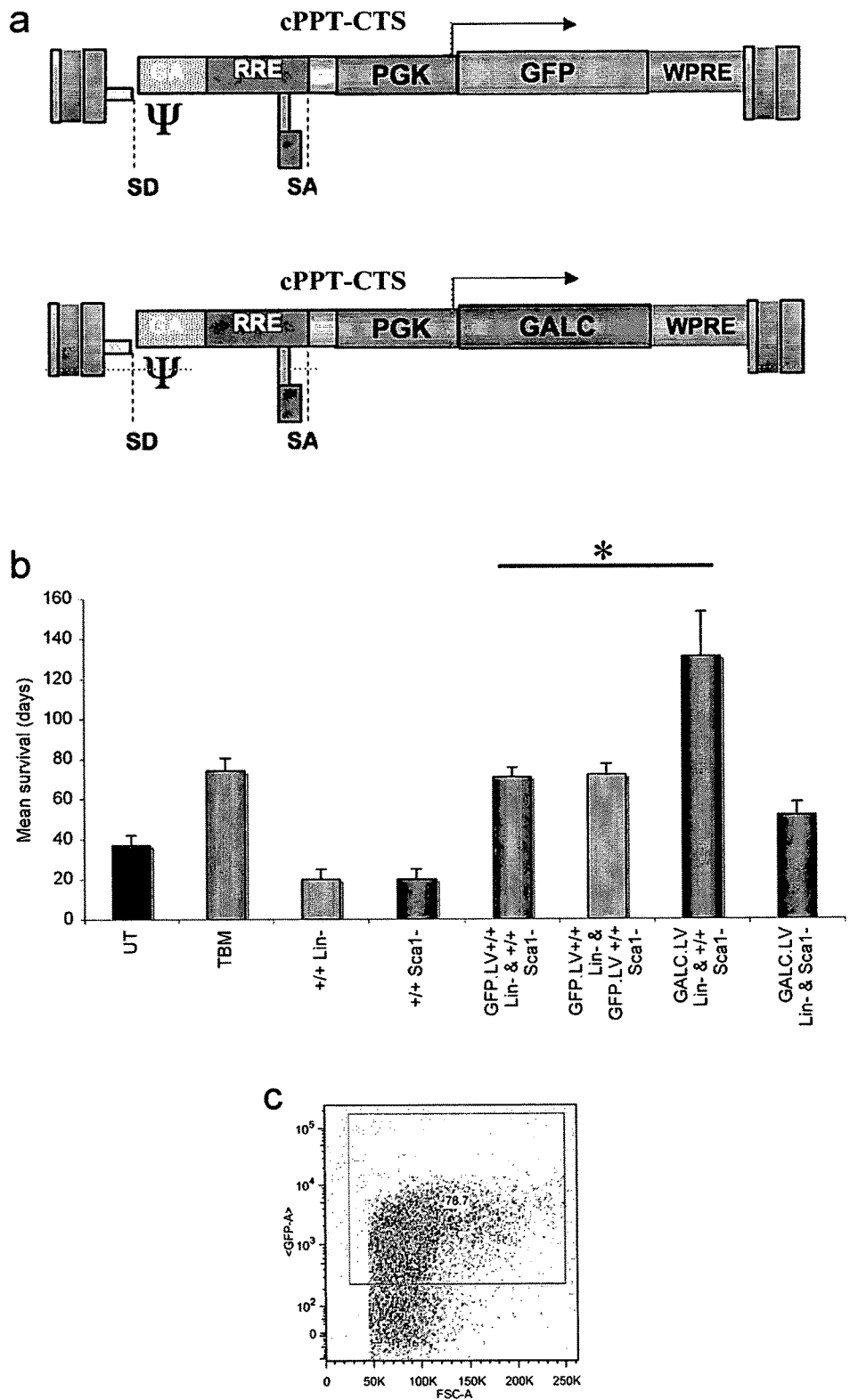
FIG. 12. Survival of twi mice upon HSCT. (A) Schematic representation of GFP.LV and GALC.LV. (B) Mean survival of twi mice receiving HSCT. Twi mice transplanted with total BM (TBM) (n=12) or with GFP.LV transduced +1+ mHSPC and untransduced Sca1-progenitors (GFP.LV+1+ Lin− & +1+ Sca1−, n=7) or with GFP.LV transduced +1+ mHSPC and GFP.LV transduced Sca1− progenitors (GF- P.LV +1+ Lin− & GFP.LV +1+ Sca1−, n=5) achieved longer survival as compared to untreated controls (UT) (n=10). Mice receiving GALC.LV transduced −I−mHSPC and +1+ Sca1− progenitors (n=7) showed a significantly higher lifespan with respect to TBM or +1+ Lin− & Sca1− transplanted mice. On the contrary, transplantation with GALC.LV transduced −I− Lin− & −I− Sca1− (n=13) did not result in a prolonged lifespan. Control groups: mice transplanted with GFP.LV transduced +1+ HSPC (+1+ Lin−) (n=10); mice transplanted with GFP.LV transduced +1+ Sca1− progenitors (n 8). *p<O.O1 at one-Way Anova test. (C) Representative plot showing the percentage of GFP$^+$ engrafted cells in the peripheral blood of a twi mouse transplanted with GFP.LV transduced +1+ mHSPC and Sca1-progenitors.

Our initial experiments were performed on twi mice, a severe model of GLD, as described in the Methods section. A first set of experiments was devoted to set the condition for HCT in twi mice. Total BM transplantation from wild type donors was performed in these mice, resulting in a significant increase of their lifespan up to 100 days, as previously reported by 115. These preliminary experiments allowed defining the optimal irradiation dose. The use of donor HSC carrying the CD45.1 allele allowed evaluating donor cell engraftment, since twi mice carry the CD45.2 allele. Because our goal was to transduce twi HSC, we tried to set up transplantation of Lin-HSPC, in order to reduce the number of cells to be transduced and transplanted as compared to the use of total BM cells. HSPC from wild type (+/+) mice were transduced at MOI 100 with PGK GFP.LV (GFP.LV), in the presence of an optimized cytokine combination (Biffi et al., 2004) (FIG. 12A). After transduction, cells were transplanted into lethally irradiated 8 day-old twi mice or +/– controls. Control groups included also twi mice transplanted with wild type BM or Lin– cells. Surprisingly, and differently from control animals, HSPC-transplanted –/– twi mice did not survive after lethal conditioning, thus suggesting that Lin– cells alone could not repopulate twi mice (FIG. 12B).

We thus decided to support GFP.LV transduced HSPC engraftment by co-transplantation of untransduced BM-derived hematopoietic committed progenitors, depleted of HSC. These cells were obtained by magnetic depletion of Sca1+ cells from total BM of +/+ mice. Interestingly, twi mice transplanted with GFP.LV transduced +/+ Lin– cells and untransduced +/+ Sca1– cells reached a survival similar to the one obtained with +/+ total BM transplantation (FIG. 12B). The engraftment of GFP.LV transduced HSPC was evaluated by flow cytometry on peripheral blood. Five-six weeks after transplantation, cytofluorimetric analysis revealed a high engraftment of GFP+ HSPC-derived cells (FIG. 12C). Thus, co-transplantation of +/+ Sca1− progenitors rescued the defective engraftment of purified HSPC and allowed prolongation of lifespan and amelioration of phenotype of twi mice similar to those obtained with total +/+ BM transplantation (Yeager et al., 1993; Wu et al., 2000).

Once the transplantation procedures had been optimized with +/+ HSPC and GFP.LV, twi mice were transplanted with GALC.LV transduced −/− HSPC and with either +/+ or GALC.LV transduced −/− Sca1− cells. Twi mice that received GALC.LV transduced −/− HSPC and +/+ untransduced cells survived significantly longer than mice transplanted with +/+ total BM or with +/+ HSPC and Sca1− progenitors, and showed amelioration of their phenotype and slower disease progression (FIG. 12B). This data suggested that GALC over-expressing HSPC transplantation provides a unique therapeutic benefit as compared to conventional HSCT. However, when we evaluated the presence of GALC.LV transduced cells in the BM of these mice by Q-PCR, we found a low Vector Copy Number (VCN), between 0.8 and 1, thus suggesting that only GALC.LV transduced cells with low VCN had been able to engraft.

Nevertheless, twi mice that received −/− Lin− and Sca1− cells, both transduced with GALC.LV, died after lethal conditioning or had a lifespan similar to untreated mice. These results suggested that GALC.LV transduced progenitors failed to support HSPC engraftment, resulting in engraftment failure and autologous reconstitution of hematopoiesis.

We decided to use FVB/twi mice instead of the usual twi model of GLD to take advantage from the slightly less severe model: previous experiments showed us that the successful transplantation of Lin− cells without the need of Sca1-supporting cells was possible in this model. Moreover, FVB/twi mice have larger litters, thus allowing us to have a larger number of −/− mice to isolate mHSPC.

Figure 13:
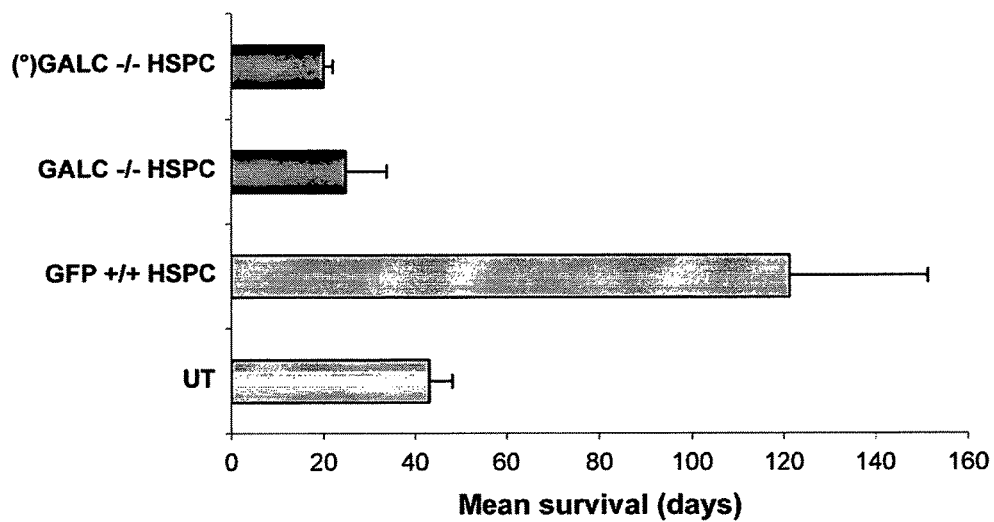
FIG. 13. Impaired in vivo function of mHSPC in FVB/twi mice. Mean survival of mice receiving mHSPC transplantation, as indicated. −/− mice transplanted with GFP.LV transduced +/+ mHSPC (n=11) achieved longer survival as compared to untreated controls (UT); on the contrary, −/− (n=9) and +/−)(° (n=5) mice transplanted with GALC.LV transduced −/− mHSPC did not survive after lethal irradiation. Table 2. Mean VCN SD detected in the BM of −/− or +/− mice transplanted with the listed mHSPC (transduced with GALC.LV or GFP.LV) at 20 and 120 days post transplant (n=3 time point).)(°+/− host. (§) Similar results were obtained using +/+ mHSPC.
Figure 13:
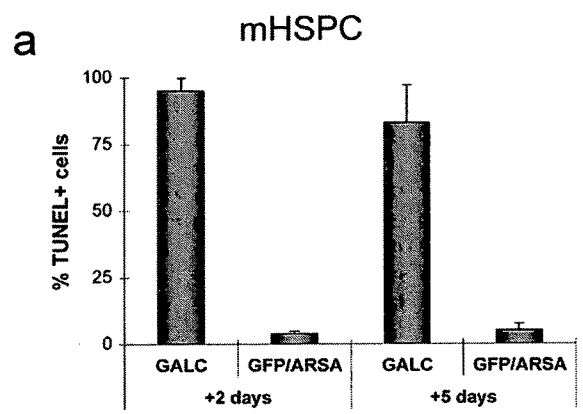
Figure 13:
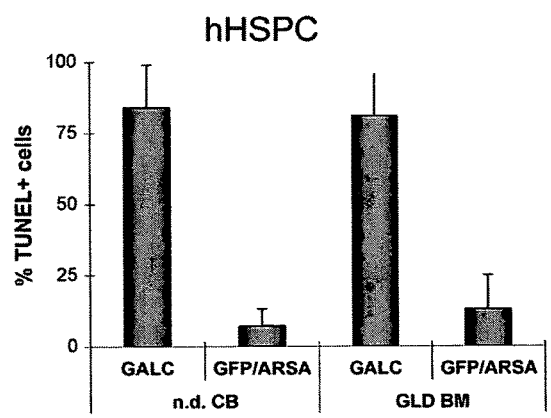
Figure 13:
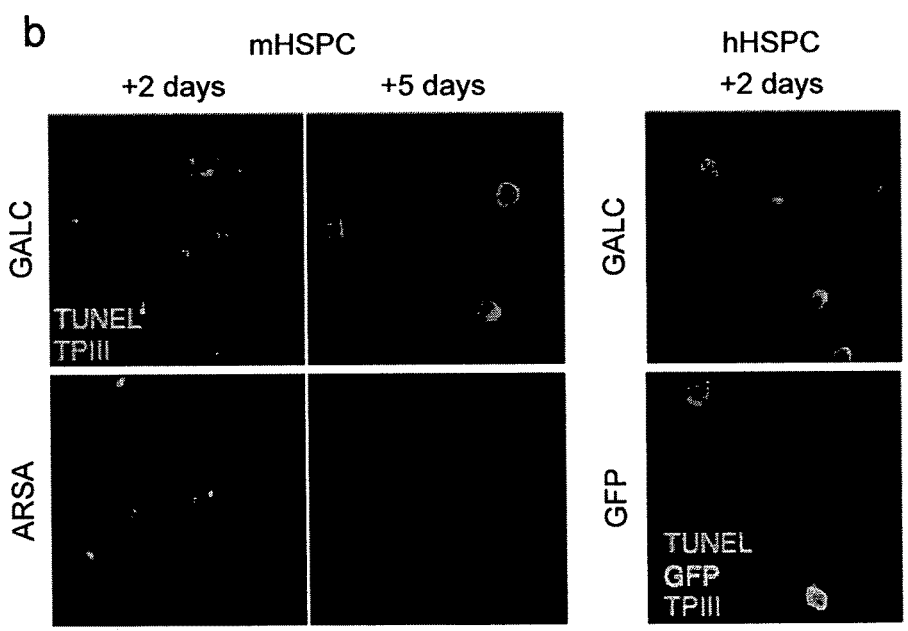

Transduced mHSPC were transplanted into lethally irradiated 8 day-old FVB/twi −/− and heterozygous (+/−) recipients (FIG. 13). In order to reduce biological variability, we transplanted −/− and +/− littermates. Mice of the control group were transplanted with GFP.LV transduced+/+ cells. For this control group, the transduction efficiency was evaluated by cytofluorimetry 7 days after transduction on the in vitro culture, while the engraftment of transduced cells was evaluated by cytofluorimetry on peripheral blood 6 weeks after HSCT. The transduction efficiency was very high, ranging between 75% and 93% of GFP+ cells. All the GFP-transplanted animals showed a high engraftment of transplanted cells (between 63% and 85%), and all the irradiation controls (lethally irradiated mice that did not received HSCT) died within 3 weeks after conditioning, thus confirming the correct setup of HSCT conditions. −/− mice receiving GFP.LV transduced +/+ mHSPC achieved prolonged survival after lethal conditioning (up to 150 days), as compared to un-transplanted control mice. The survival of the untreated and GFP-transplanted FVB/twi mice was longer with respect to that observed in the respective groups of twi mice, thus confirming the influence of the genetic background on the severity of the phenotype. The engraftment of transduced mHSPC was also evaluated by Q-PCR on DNA extracted from BM transplanted mice at sacrifice. A significant engraftment of GFP.LV transduced mHSPC, measured as VCN per genome, was observed (Table 2). Strikingly, both −/− and +/− mice transplanted with GALC.LV transduced −/− or +/+ mHSPC did not survive to lethal irradiation (death within 21 days, similar to that of irradiation controls) (FIG. 13 and data not shown). Q-PCR revealed very low to undetectable VCN in their BM (Table 2). These results indicated a functional impairment of GALC-transduced mHSPC, which became unable to repopulate a lethally conditioned host.

Apoptosis of GALC Expressing Murine and Human HSPC.

Figure 14:
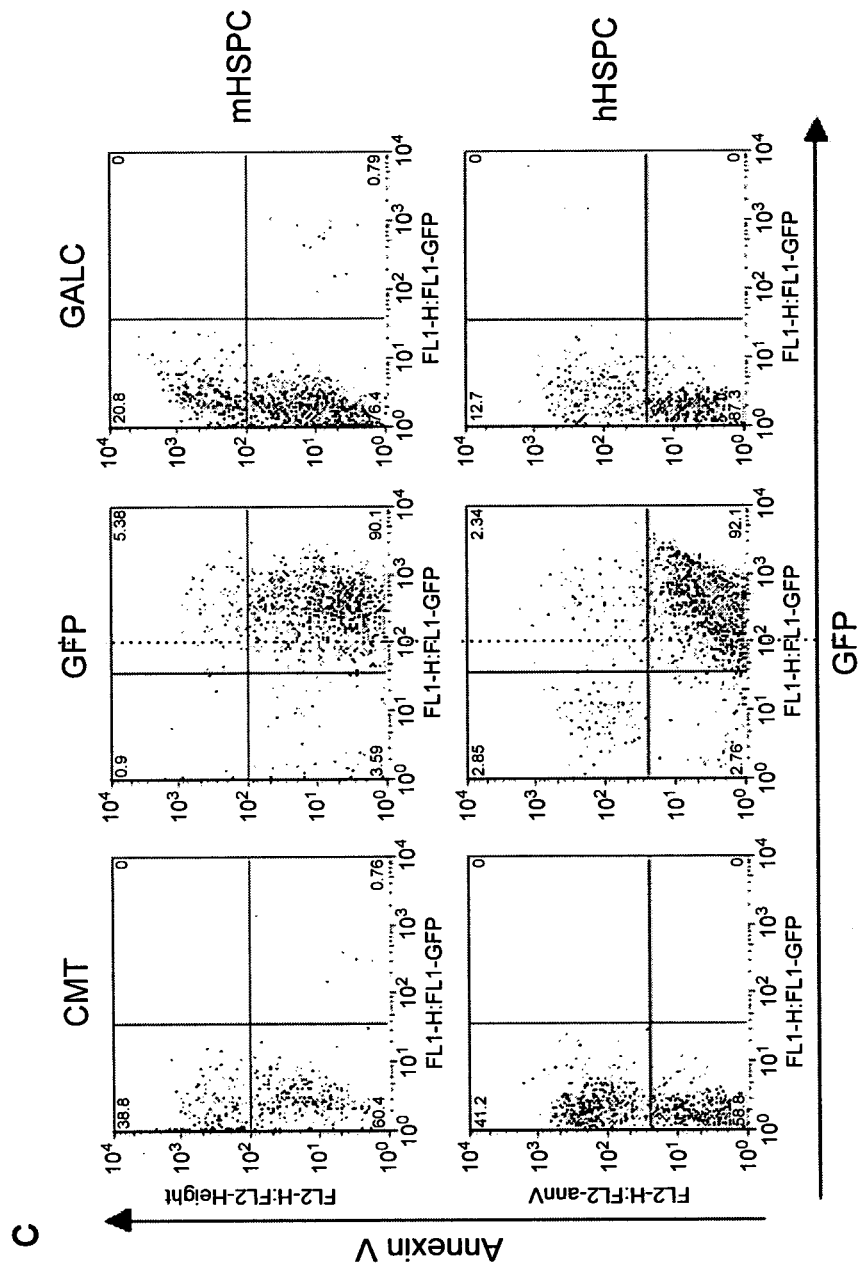
FIG. 14. Apoptosis of GALC expressing murine and human HSPC. (A-B) TUNEL assay on −/− mHSPC (left) and hHSPC (right)(from n.d. CB and GLD BM) at 2 and 5 days after gene transfer. % of TUNEL+ nuclei over the total number of nucleated cells is reported. 8 fields and 100 cells were counted condition. Similar results were obtained using +/+ mHSPC. (A) The large majority of GALC.LV transduced m− and hHSPC were TUNEL positive both at 2 and at 5 days after transduction. (B) TUNEL assay (red) and ToPro(TPIII, blue) staining for nuclei on m− and hHSPC at 2 and (mHSPC) days after transduction with the indicated LV: representative images (images were acquired by three-laser confocal microscope—Radiance 2100, BioRad; fluorescent signals from single optical sections were sequentially acquired and analyzed by Adobe Photoshop CS software; magnification 100×). (C) Cytofluorimetric analysis of Annexin V staining on m-(top panels)(from −/− donor mice) and hHSPC (bottom panels)(from n.d. CB). The fraction of apoptotic cells is higher among GALC.LV transduced mHSPC and hHSPC as compared to GFP-transduced controls. CMT=Camptotecin treated positive control. Acquisition was performed with FACS Calibur 2, Beckton Dickinson. At least 10,000 events were scored and data were processed by FlowJo 8.5.3 software. Data from −/− mHSPC and n.d. CB (and GLD BM for TUNEL) are shown, but similar findings were obtained following GALC transduction of +/+ mHSPC as compared to −/− cells and in n.d. BM (TUNEL and Annexin V) and GLD BM (Annexin V) hHSPC as compared to CB cells.
Figure 14:
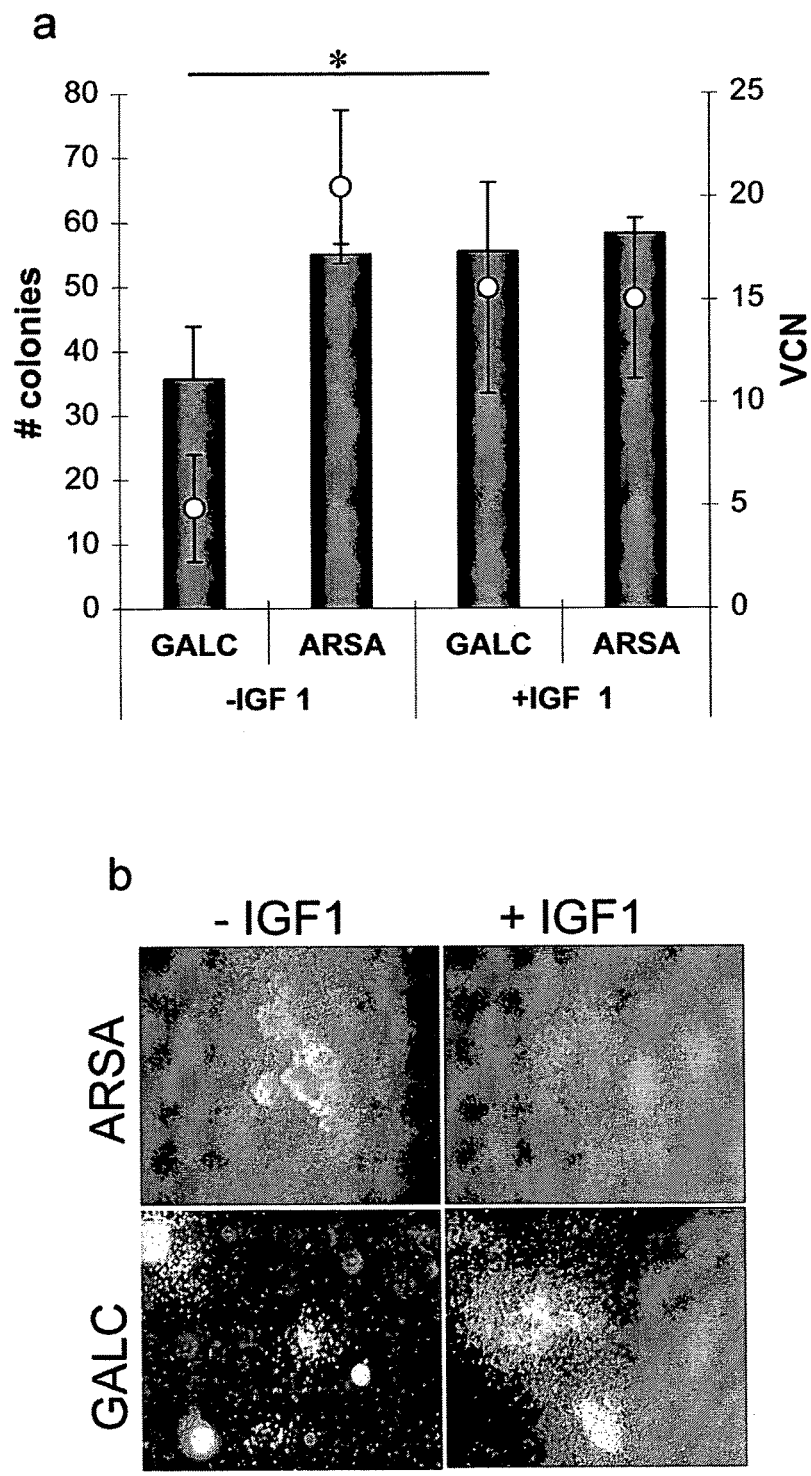
Figure 15:
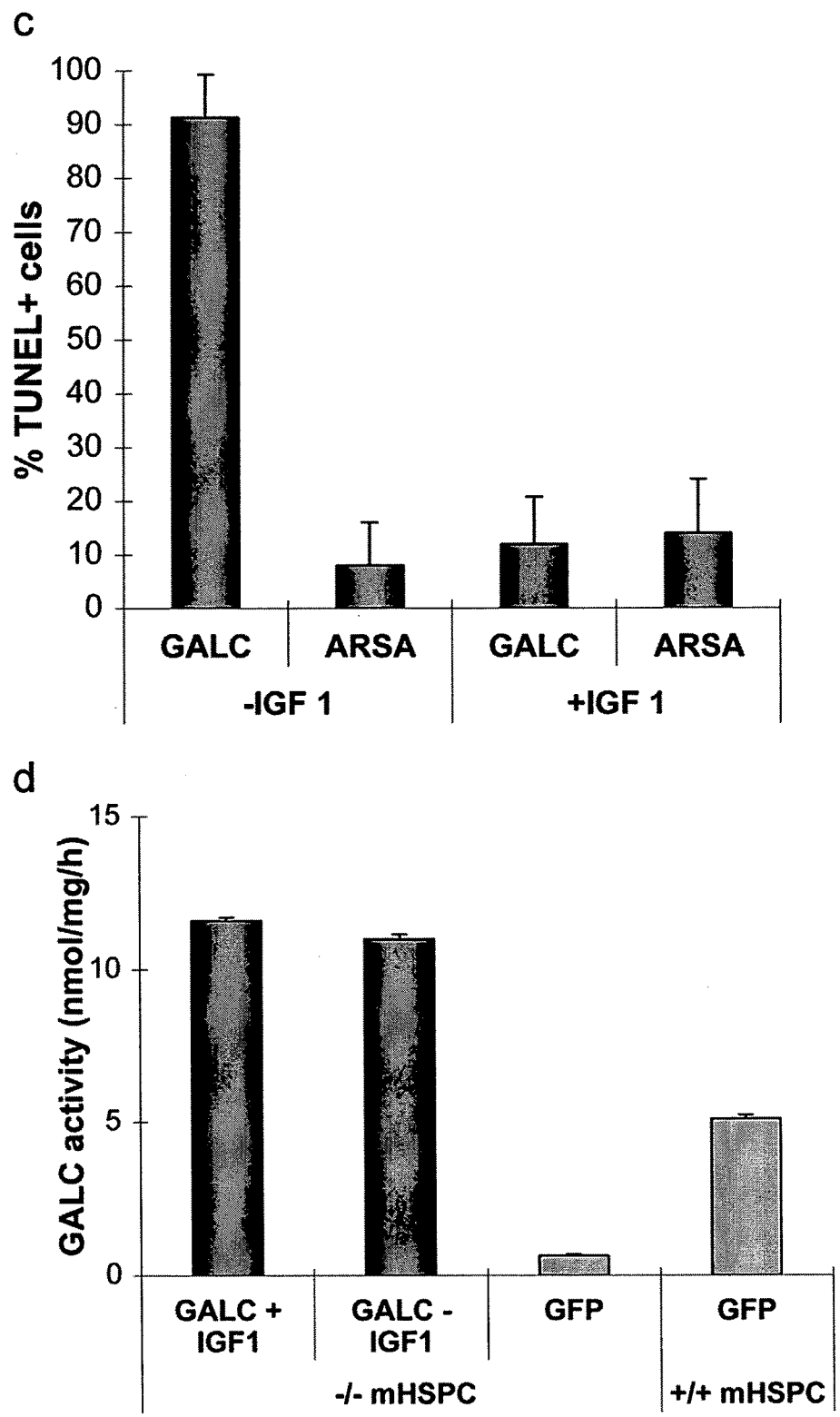
FIG. 15. IGF1 treatment prevents apoptosis of GALC expressing HSPC. (A) CFC assay on GALC.LV and ARSA.LV transduced mHSPC treated or not with IGF 1. The number (#) of colonies/plate (Y left axis, bars) was counted and the number of integrated lentiviral vector copies/cell (VCN) (Y right axis, dots) was measured. IGF 1 treatment induced growth of a higher colony number, as compared to GALC.LV transduced untreated cells (n=4 independent experiments). Upon anti-apoptotic treatment, the VCN of GALC.LV transduced cells approached that of ARSA.LV transduced control cells (for both CFC number and VCN one-Way Anova: *=p<0.001 for the comparison of treated GALC transduced mHSPC with untreated GALC.LV transduced cells; p>0.05 for the comparison of treated GALC.LV transduced mHSPC with ARSA.LV transduced cells). (B) The colonies grown from treated mHSPC also showed an increase in size (pictures on the right, magnification 5×). (C) TUNEL assay on GALC.LV and ARSA.LV-transduced mHSPC treated or not with IGF1. 8 fields and 100 cells were counted condition. The large majority of treated cells were negative for TUNEL (one-Way Anova: p<0.001 for the comparison with untreated GALC.LV transduced cells; p>0.05 for the comparison with ARSA.LV transduced cells). (D) GALC activity measured on transduced mHSPC from −/− or +/+ mice. IGF1 treatment did not significantly affect GALC expression levels (n=3) when compared to transduced untreated controls (n=6). Mean values SD are shown.
Figure 16:
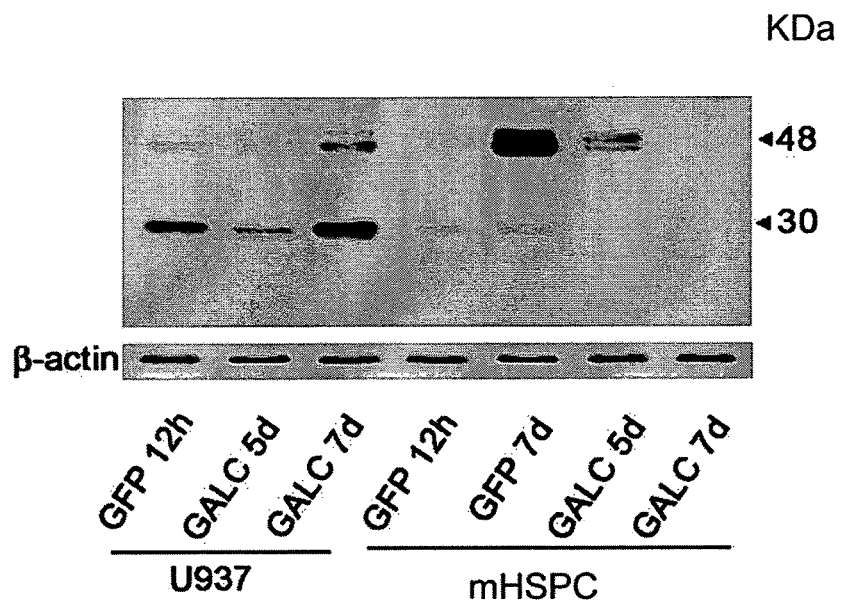
FIG. 16. Analysis of Cathepsin D activation in transduced cells. Western blot analysis for Cathepsin D on GFP.LV or GALC.LV transduced mHSPC and U937 cells at different intervals after gene transfer, as indicated. Activated form corresponds to 30 kDa membrane bound isoform, as indicated by arrow. No significant accumulation of the active form of Cathepsin D was observed in GALC.LV transduced cells after gene transfer, compared to GFP.LV transduced cells. The precursor (48 kDa, arrow) accumulated in GFP-transduced cells after 7 days of culture (GFP 7d), while its accumulation was less pronounced in the presence of GALC (GALC 5d), culminating with disappearance of both the precursor and mature forms after 7 days. An anti-actin was used as control for protein loading.

Having detected a functional impairment of GALC.LV transduced HSPC, we evaluated whether this could be due to apoptosis of the transduced cells mediated by de novo GALC expression. The occurrence of apoptosis was evaluated at two different time points, 2 and 5 days after transduction, when transgene expression presumably reaches steady state (see GFP expression in FIG. 14B) by Annexin V staining and TUNEL assay. The first technique labels early apoptotic cells, and the second one late apoptotic cells. m- and hHSPC were transduced with GALC.LV and control GFP/ARSA.LV. After transduction and washing, cells were plated on matrigel-coated coverslips for TUNEL assay or cultured in usual plates and stained for Annexin V and TUNEL. At confocal microscopy, the large majority of GALC.LV transduced mHSPC were TUNEL positive and exhibited enlarged nuclei with condensed chromatin, demonstrating the widespread occurrence of apoptosis at both time points (FIG. 14A-B). On the contrary, ARSA/GFP.LV transduced cells were mostly TUNEL negative. Annexin V staining confirmed the occurrence of apoptosis, showing a higher fraction of apoptotic cells among GALC-transduced m- and hHSPC, as compared to controls (FIG. 14C).

Figure 17:
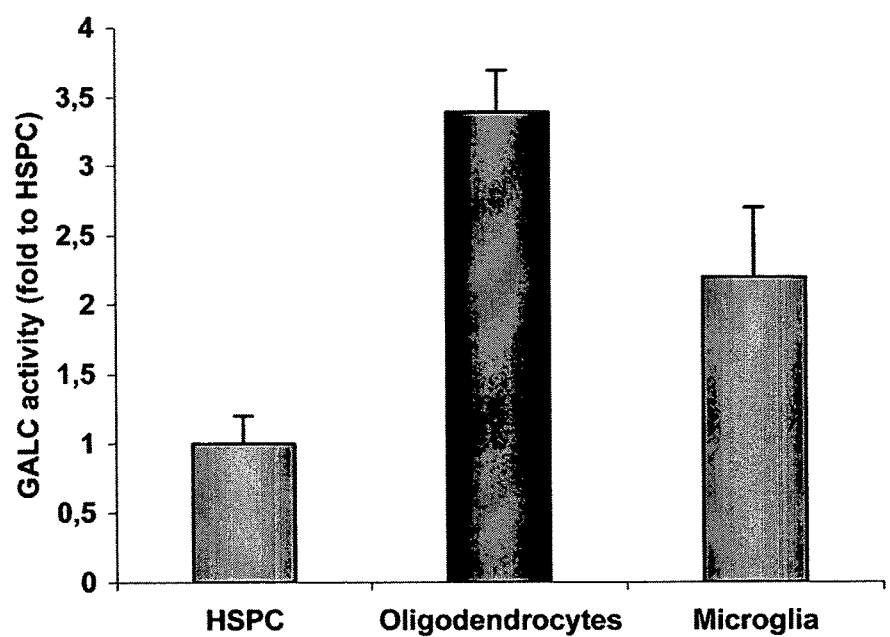
FIG. 17. Basal GALC activity in different cell types. Basal GALC activity normalized to wild type mHSPC level. Both primary wild type oligodendrocytes (n=4) and microglia (n=4) showed a higher GALC activity as compared to mHSPC.

Sensitivity to GALC Expression Toxicity is Dependent on Differentiation and Cel Lineage Macrophages and microglia represent the HSPC effector progeny reconstituting enzyme activity in affected tissues, including the nervous system, in HSPC gene therapy approaches for LSD. We evaluated whether a prototypical monocytic cell line (U937), primary human monocytes, primary murine macrophages and microglia could experience GALC expression toxicity upon LV mediated gene transfer. Moreover, for further dissecting the specificity of GALC-induced apoptosis along hematopoietic differentiation, we tested T and B lymphocytes. To permit immunodetection of GALC and estimate transduction efficiency, in some experiments we used a C-terminally tagged transgene, in which the gene is fused in frame with the sequence encoding the HA peptide from the hemagglutinin protein of the human influenza virus. The HA-tagged enzyme had a specific activity comparable with that of the un-modified enzyme, and was properly sorted to the lysosomal compartment (data not shown). After transduction, we evaluated at different time points the occurrence of apoptosis by TUNEL assay and GALC activity. As expected, all the cell types analyzed showed a different level of basal GALC activity (FIG. 17).

Figure 18:
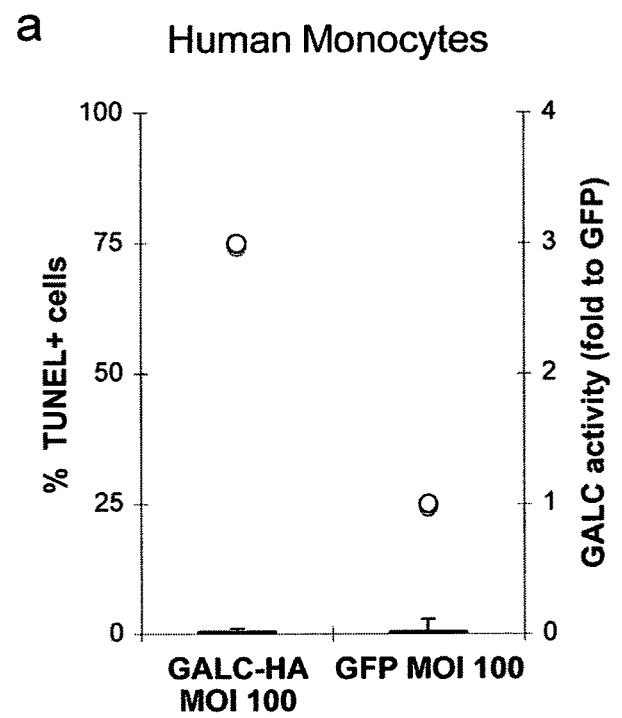
FIG. 18. Sensitivity to GALC de novo expression in myeloid cells. Results from TUNEL assay (% TUNEL+ cells over the total nucleated cells, on Y left axis, bars), GALC activity determination (on Y right axis, dots) and, when possible, dedicated stainings, performed on (A) human monocytes, (B) the monocytic human cell line U(C) murine macrophages and D) murine microglia, 5 days after transduction. In all tested conditions, TUNEL staining demonstrated the occurrence of minor/no apoptosis (≥6 fields and ≥250 cells were counted per condition), despite efficient transduction (evaluated by anti-HA staining on macrophages in (C)) and sustained GALC expression above basal levels in all the other samples (ARSA.LV- or GFP.LV-transduced cells), were obtained. Mean values±SD are shown. (C and D) Representative images of TUNEL assay on GALC/GALC-HA.LV or GFP.LV transduced macrophages (C) and microglia (D). Images were acquired by three-laser confocal microscope (Radiance 2100, BioRad). Fluorescent signals from single optical sections were sequentially acquired and analyzed by Adobe Photoshop CS software. Magnification: 80× in C, 100× in D.
Figure 18:
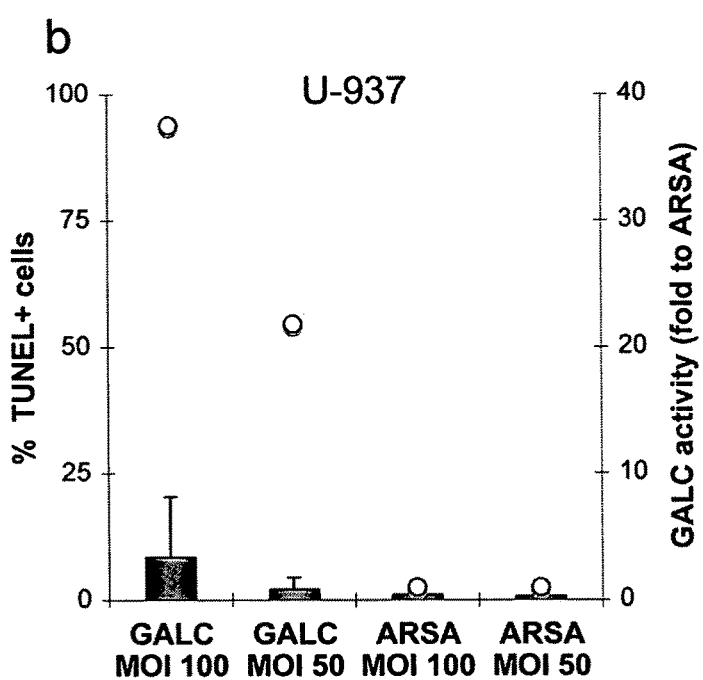
Figure 18:
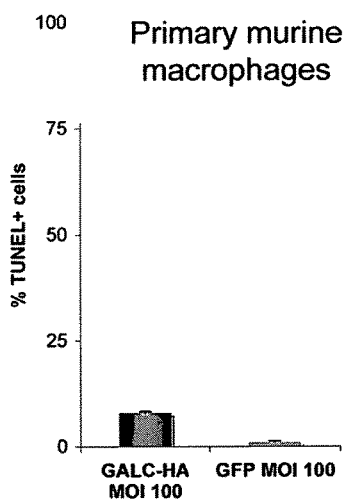
Figure 18:
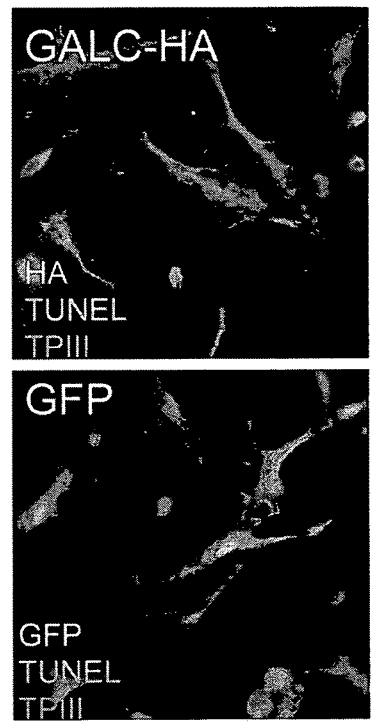
Figure 18:
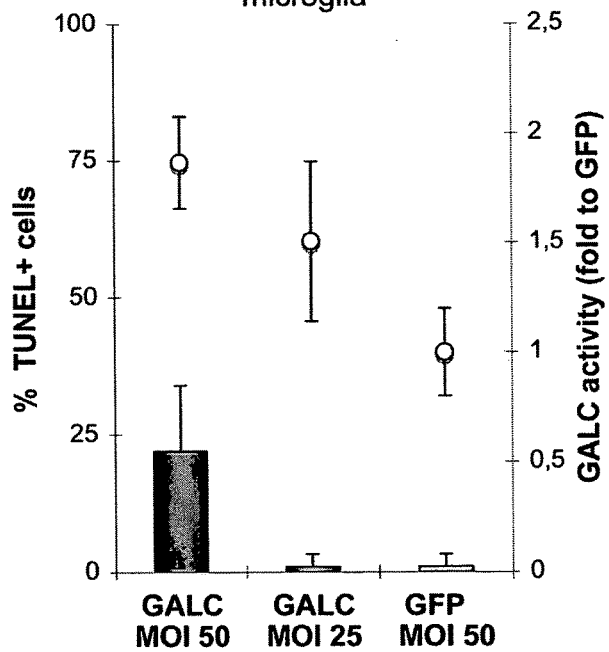
Figure 18:
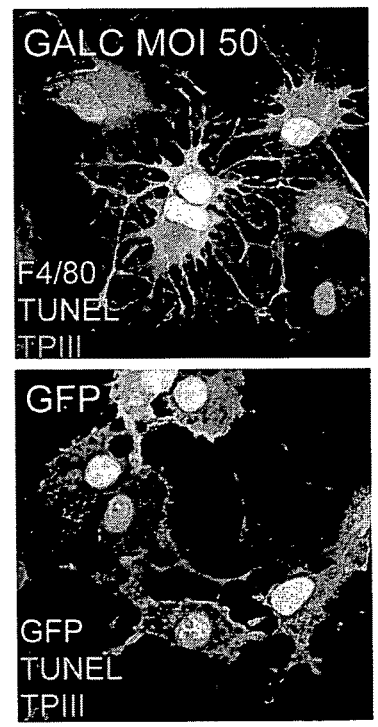

Murine macrophages were obtained as the adherent fraction of peritoneal cell collection. Primary cultures of microglia were isolated from the brain of +/+ and −/− FVB/twi mice by established protocols (Armstrong R C., 1998; Gritti et al., 1996). Further, we tested both primary monocytes and U937 monocytic cell line. Human monocytes were isolated from PBMC by positive selection for the CD14 monocytic marker. Transduction conditions were set up using GFP.LV and analyzing the transduction efficiency by cytofluorimetry (when possible) or by confocal microscopy. Once the transduction protocol had been optimized, microglia and macrophages were efficiently transduced with GALC.LV/GALC-HA.LV and control vectors at MOI 50 and 200, respectively, and expressed GALC above basal levels (FIG. 18). Even when high expression levels (up to 40 fold to wt level) were achieved, TUNEL assay demonstrated low frequency or no apoptosis following GALC.LV transduction and GALC overexpression in all tested cells (FIG. 18). No difference was observed between +/+ and −/− microglia (FIG. 18 and other data not shown). These results demonstrate that HSC gene therapy effector cells are not sensitive to GALC toxicity, thus suggesting that, in order to develop a HSC gene therapy strategy for GLD, GALC expression should be avoided in HSPC, whereas it should be promoted in differentiated hematopoieic myeloid cells, capable of targeting the enzyme to affected tissues.

Figure 19:
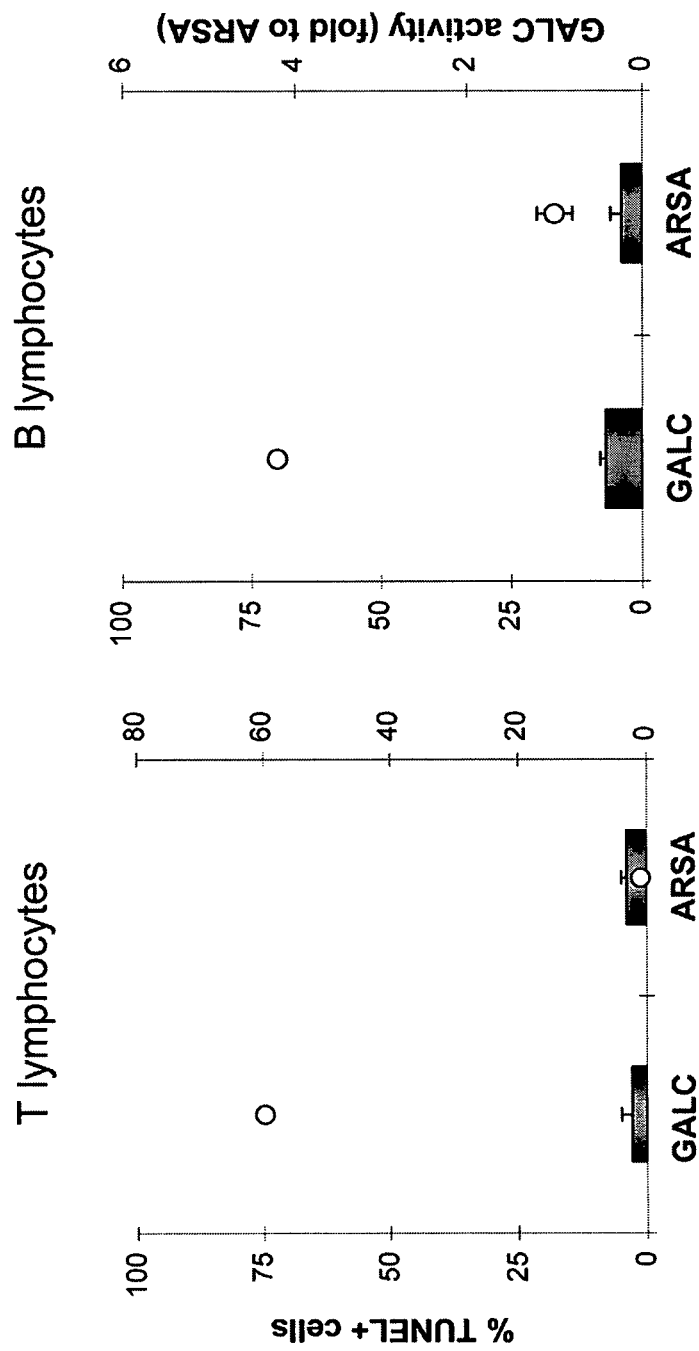
FIG. 19. Sensitivity to GALC de novo expression in lymphocytes. Results from TUNEL assay (% TUNEL+ cells over the total nucleated cells, on Y left axis, bars), GALC activity determination (on Y right axis, dots), performed on T and B lymphocytes, 5 days after transduction. TUNEL staining demonstrated the occurrence of minor/no apoptosis (≥6 fields and ≥250 cells were counted per condition), despite efficient transduction (see the sustained GALC expression above basal levels). Mean values ±SD are shown.
Figure 20:
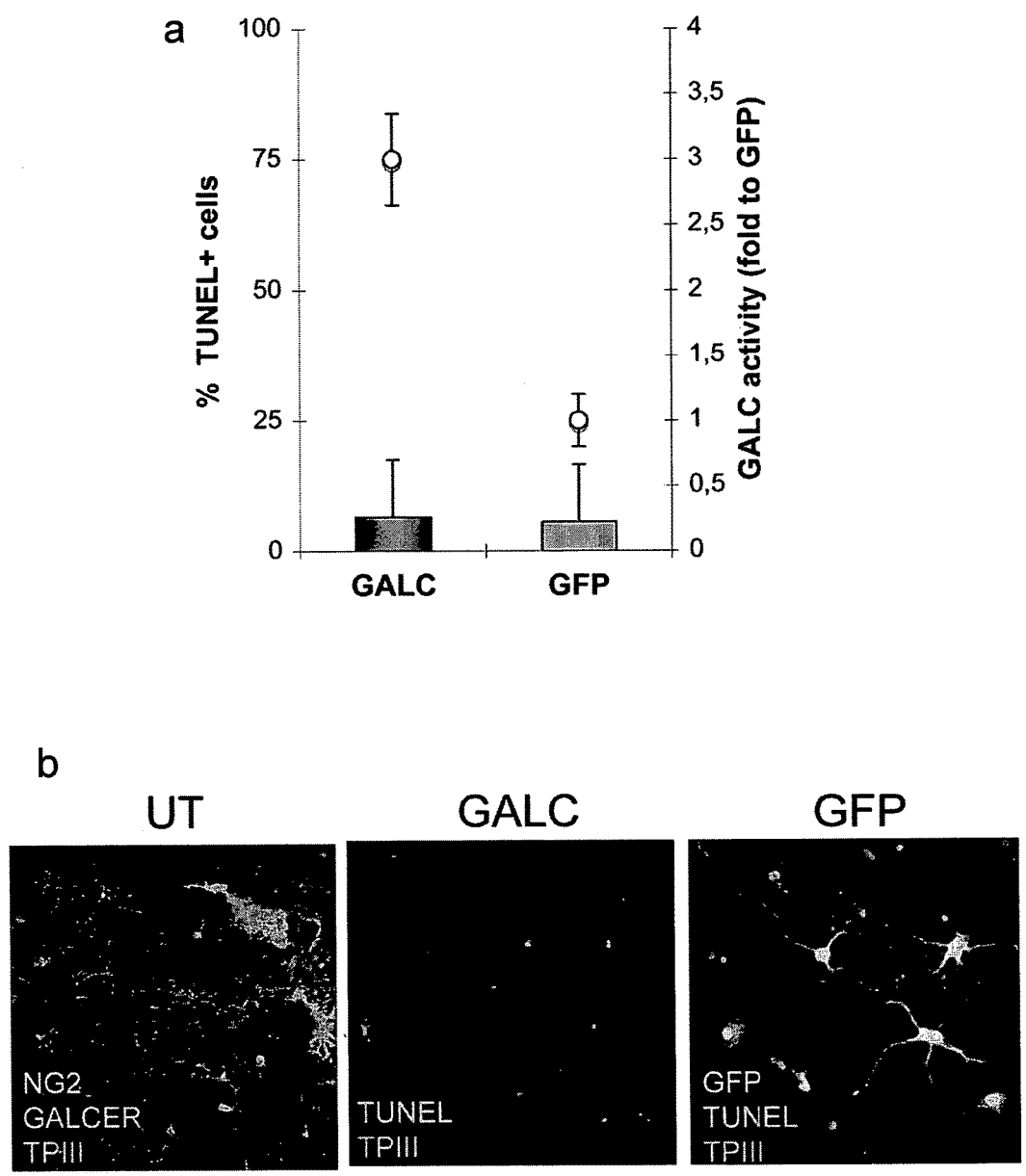
FIG. 20. Sensitivity to GALC de novo expression in oligodendrocytes. (A) TUNEL assay (% TUNEL+ cells over the total nucleated cells, on Y left axis, bars), GALC activity determination (on Y right axis, dots), performed 5 days after transduction. TUNEL staining demonstrated the occurrence of minor/no apoptosis (≥6 fields and ≥250 cells were counted per condition), despite efficient transduction (see the sustained GALC expression above basal levels). Mean values ±SD are shown. (B) Representative images of TUNEL assay on GALC.LV or GFP.LV transduced oligodendrocytes. The purity of the oligodendrocyte preparation was verified by NG2 and Gal-Cer staining on non-transduced cells (UT), while microglia was stained with F4/80 on GALC.LV-transduced cells; ToPro(TPIII) was used to stain nuclei. Images were acquired by three-laser confocal microscope (Radiance 2100, BioRad). Fluorescent signals from single optical sections were sequentially acquired and analyzed by Adobe Photoshop CS software. Magnification: 40×.

Human T and B lymphocytes were obtained upon PHA-stimulation and EBV transformation of total PBMC, respectively. Similarly to the experiments with monocytes and macrophages, transduction was optimized by using GFP.LV and flow cytometry. B lymphocytes were efficiently transduced with GALC.LV/GALC-HA.LV and control vectors at MOI 100 while two hits at MOI 100 were used for T lymphocytes. Despite sustained increase on GALC activity upon transduction, no apoptosis was detected at all the examined time points (FIG. 19), thus further supporting the notion that differentiated hematopoietic cells are not detectably sensitive to GALC over-expression.

In Vitro Regulation on GALC Expression by miRNA126.

Figure 21:
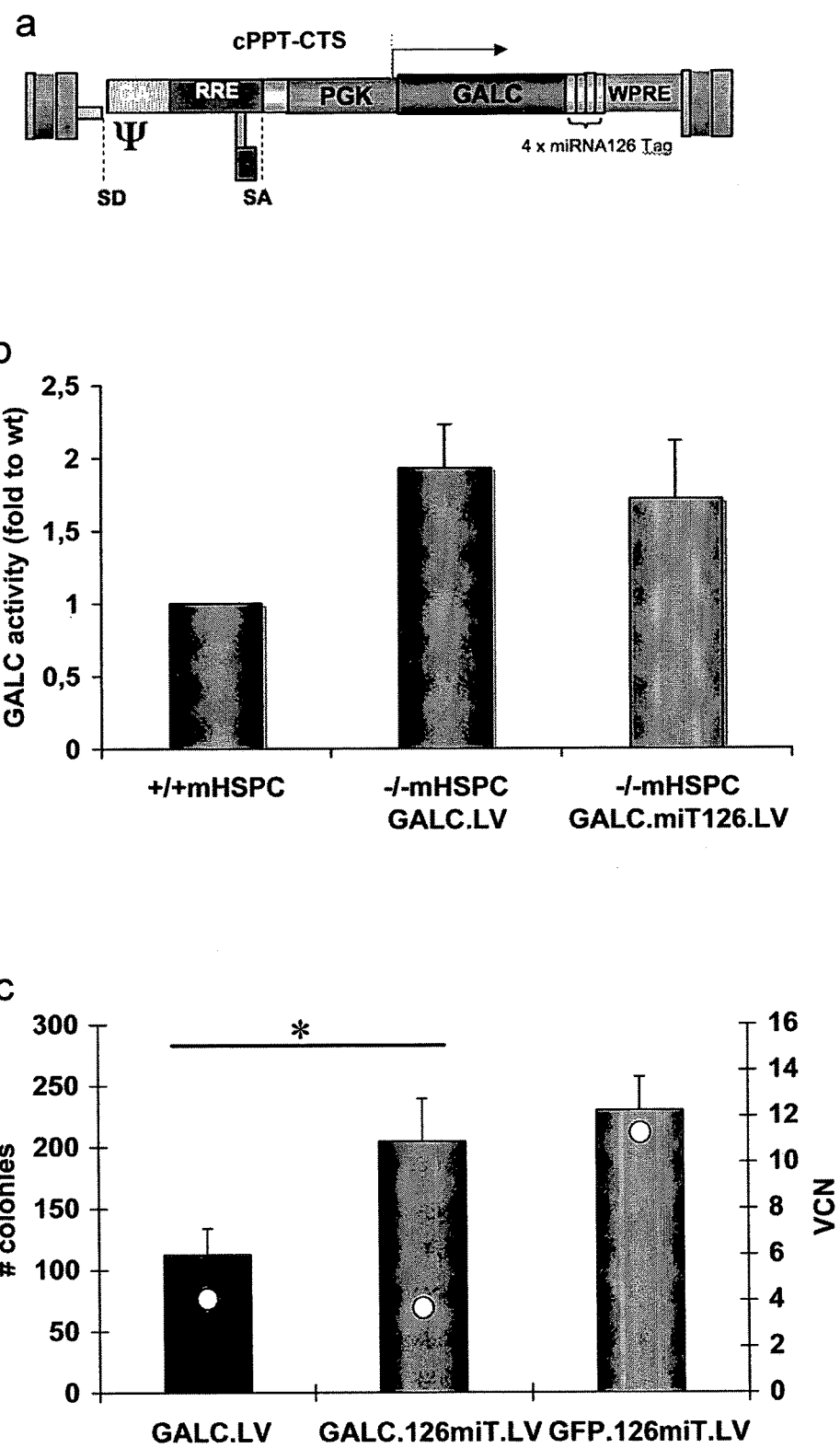
FIG. 21. Regulation of GALC expression by miRNA 126. (A) Schematic representation of GALC.miRNA126Tag.LV. (B-C) GALC activity assay and CFC assay performed on −/− mHSPC transduced with GALC.miRNA126Tag.LV (GALC.126miT) or with GALC.LV or GFP.miRNA126Tag.LV. (B) Activity was normalized respect to +/+ levels (first column). Cells transduced with GALC.miRNA126Tag.LV over-express GALC at supraphysiological levels. (C) The number (#) of colonies/plate (Y left axis, bars) was counted and the number of integrated lentiviral vector copies/cell (VCN)(Y right axis, dots) was measured. Repression of GALC expression by miRNA126 allowed growth of a higher colony number, as compared to GALC.LV transduced cells (n=4 independent experiments). *p<0.01 at one-Way Anova test.
Figure 22:
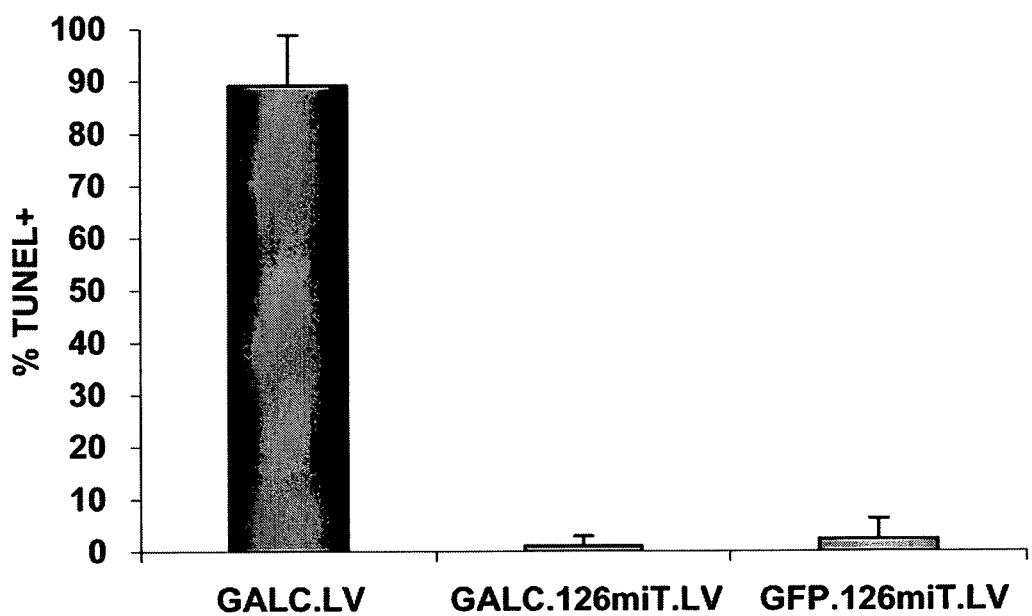
FIG. 22. miRNA126 regulation of GALC expression prevents apoptosis of mHSPC. (A) TUNEL assay on GALC.miRNA126Tag.LV or GALC.LV and GFP.miRNA126Tag.LV-transduced mHSPC. ≥8 fields and ≥100 cells were counted per condition. The large majority of GALC.miRNA126Tag.LV transduced cells was negative for TUNIEL. (B) TUNEL assay (red) and ToPro(TPIII, blue) staining for nuclei on GALC.miRNA126Tag.LV or GALC.LV transduced mHSPC−/− 5 days after transduction: representative images (images were acquired by three-laser confocal microscope—Radiance 2100, BioRad; fluorescent signals from single optical sections were sequentially acquired and analyzed by Adobe Photoshop CS software; magnification 40×).
Figure 22:
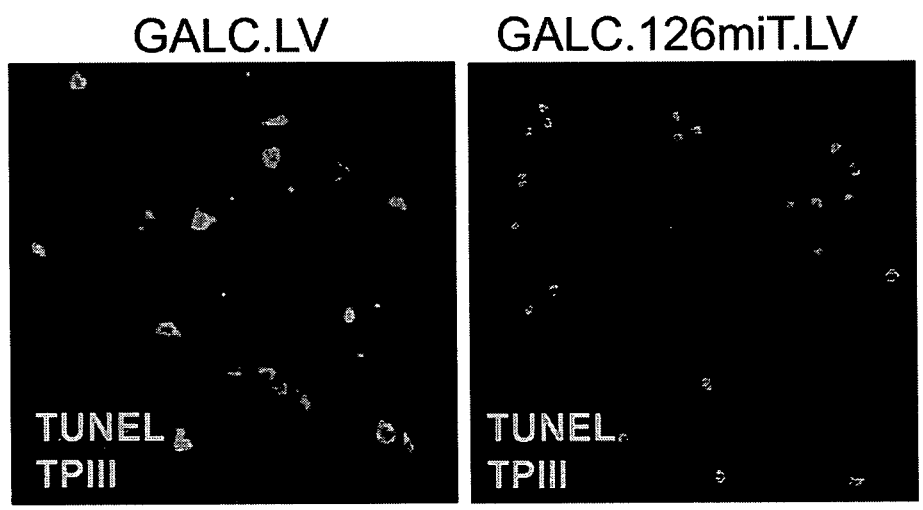

In order to evaluate the effect of miRNA126-regulated GALC expression in HSPC, we transduced mHSPC with GALC.miR126T.LV or with GFP.miR126T.LV or GALC.LV at MOI 100. After washing, cells were seeded for CFC assay or cultured in vitro for two weeks for GALC activity assay and Q-PCR analysis. Transduction with GALC.miR126T.LV allowed a reconstitution of GALC activity at supraphysiological levels in the differentiated mHSPC progeny, up to 2 fold over wild type levels (FIG. 35B). Importantly, the number of colonies obtained from mHSPC transduced with GALC.miR126T.LV was similar to controls and was almost 2-fold with respect to GALC.LV colonies (FIG. 21C), thus suggesting that regulation of GALC expression by miRNA126 allowed preserving the clonogenic potential of transduced mHSPC. These encouraging results prompted us to evaluate if the unaffected clonogenic potential was due to the rescue from apoptosis of GALC.miR126T.LV transduced mHSPC. After transduction, mHSPC were seeded on matrigel-coated coverslip and TUNEL assay was performed after 2 and 5 days of culture. The level of apoptosis was evaluated by confocal microscopy. TUNEL assay on GALC.miR126T.LV transduced cells showed minor or no apoptosis at both the time points (1%1 and 3%2 at 2 and 5 days respectively), similarly to what was observed in cells transduced with the control LV (FIG. 22A-B). This data demonstrated that suppression of GALC expression by miRNA126 could rescue mHSPC from GALC-induced apoptosis.

In vivo regulation on GALC expression by miRNA126.

The effect of miRNA126-regulated GALC expression on mHSPC repopulation potential was evaluated in +/− FVB/twi mice. Lethally irradiated 8 day-old mice were transplanted with GALC.miR126T.LV transduced −/− mHSPC or with PGK GALC.LV transduced cells and survival was evaluated at both short- and long-term. Similarly to what observed with CD11b_GALC.LV, +/− FVB/twi mice transplanted with GALC.miR126T.LV transduced mHSPC were rescued from lethality and survived long term (more than 3 months after HSCT), differently from PGK GALC.LV-transplanted mice that did not survive after lethal conditioning. When mice transplanted with GALC. miR126T. LV transduced mHSPC were euthanized at the age of 80 days and Q-PCR analysis was performed on BM, we found an average VCN of 5, thus confirming the presence of transduced cells in the BM long-term after HCT.

Overall, these results together to those observed with CD11 b_GALC.LV transduced cells, show successful rescue of the GALC deficiency and protection from de novo GALC expression in HSPC by our improved regulated gene therapy strategies.

Figure 23:
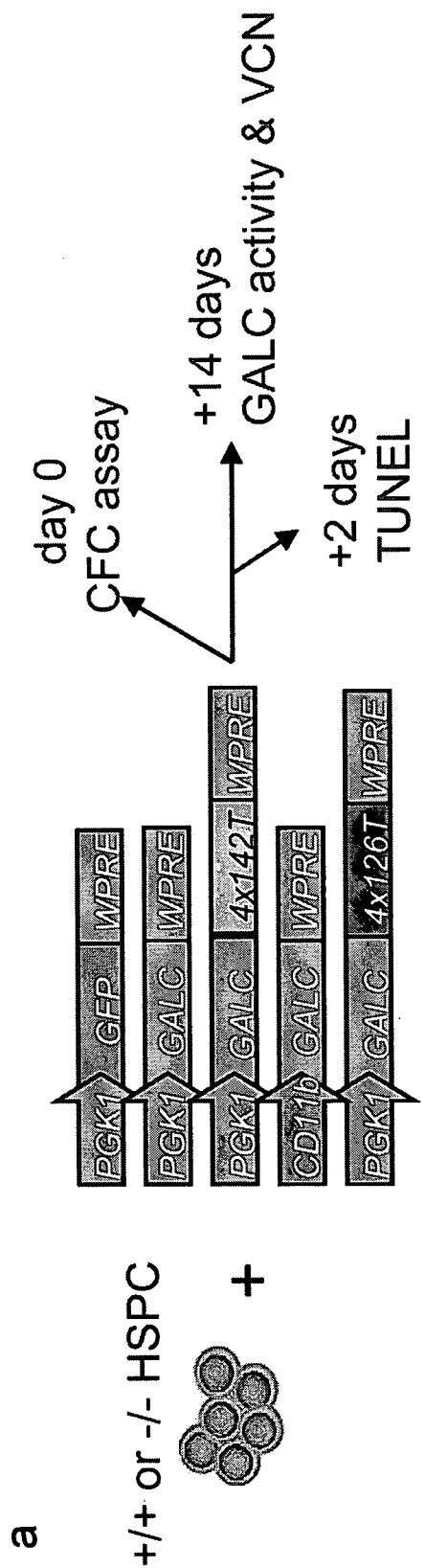
FIG. 23. Toxicity of de novo GALC expression in HSPC and rescue by miR-126 regulation.
Figure 23:
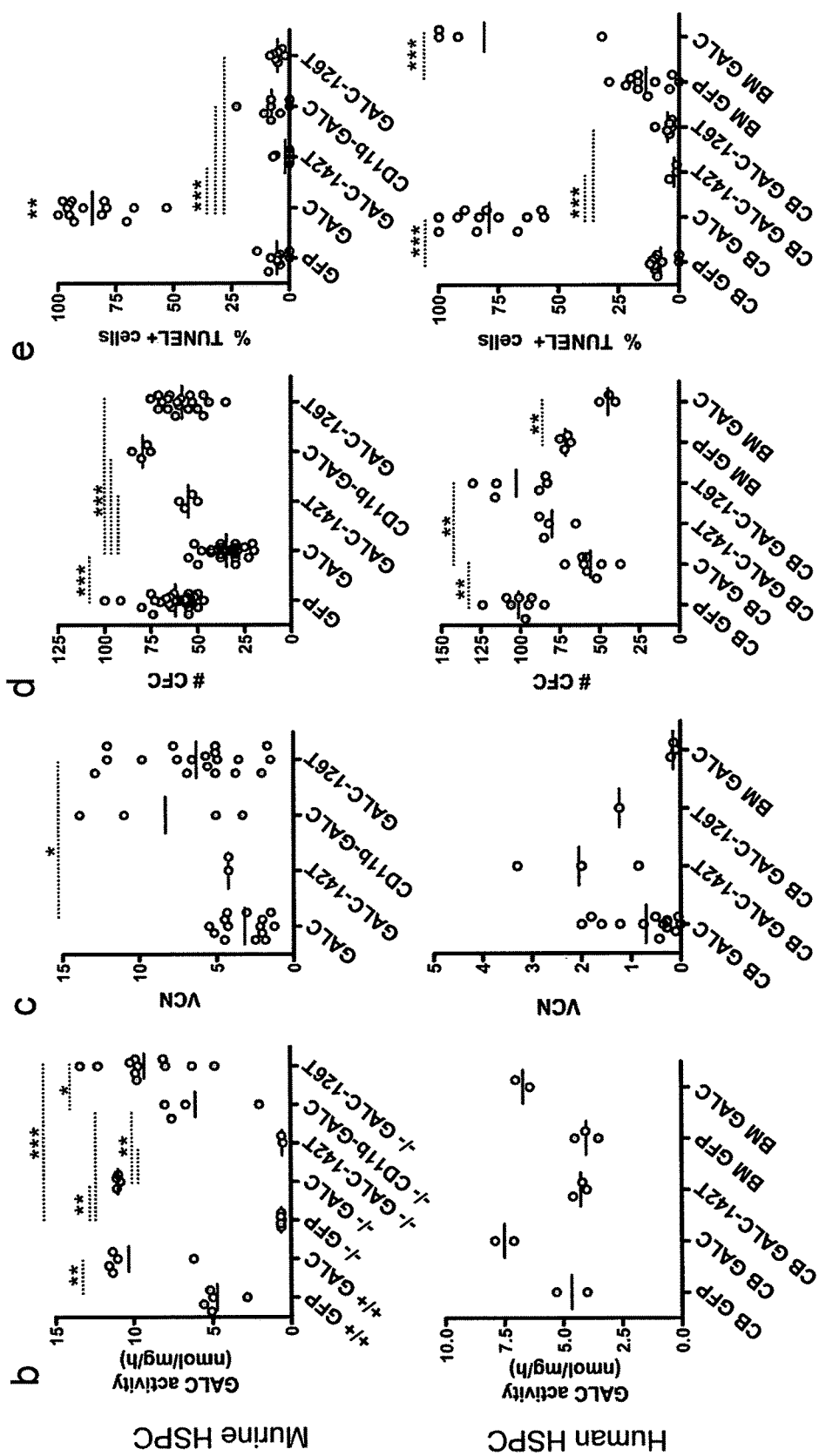
Figure 23:
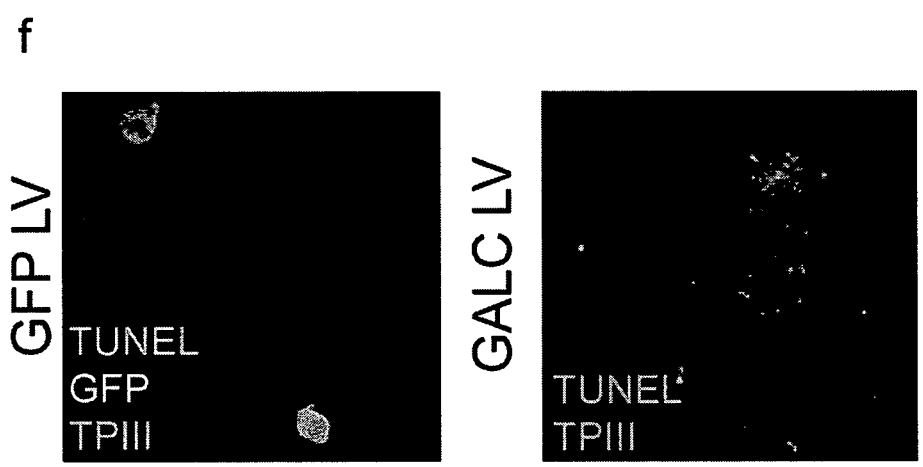

Forced GALC Expression is Toxic to HSPC but not to Differentiated Hematopoietic Cells To develop a model of gene therapy, we transduced HSPC from wild type and GLD mice, carrying a point mutation resulting in <5% residual enzyme activity (Tr s)[45], with a GALC- or GFP-expressing lentiviral vector (FIG. 23A). Transduction with the GALC vector reconstituted GALC activity in the cultured progeny of GLD cells, leading to a ~2 fold over-expression compared to GFP-transduced wild type cells (FIG. 23B). Similar expression levels were observed upon transduction of wild type murine HSPC as well as human CD34$^+$ HSPC from normal CB or BM (FIG. 23B). Unexpectedly, forced GALC expression impaired clonogenic activity of both murine and human HSPC as compared to GFP-transduced cells (FIG. 23D and data not shown). TUNEL assay performed two days after transduction showed that the majority of GALC−, but not GFP-transduced HSPC were TUNEL positive and exhibited enlarged nuclei with condensed chromatin (FIGS. 23E and F). These findings suggest that the clonogenic impairment of GALC-transduced HSPC was due to the induction of apoptosis, as also confirmed by annexin V staining (not shown). Functional impairment of HSPC was directly caused by forced/de novo GALC expression and not by toxicity related to the vector preparation, as HSPC transduced with a miR-142-regulated, GALC-encoding lentiviral vector showed normal clonogenic activity and absence of apoptosis. Indeed, the 142T sequence suppressed GALC enzyme expression in hematopoietic cells but not in LV producer cells[33] (FIG. 23B). Forced/de novo GALC expression was also toxic to long-term engrafting cells, as GALC-transduced murine HSPC failed to rescue Trs mice from lethal irradiation (FIG. 24A).

Upon HSC transplantation, macrophages and microglia are the effector progeny responsible for reconstituting GALC activity in the affected tissues. To test whether toxicity by forced/de novo GALC expression also affected differentiated cells, we transduced human primary monocytes, T and B lymphocytes, as well as mouse microglia cells with GALC- or control vectors (FIG. 24B). While efficient transduction and GALC over expression were achieved in all cell types, TUNEL assay showed low or no apoptosis in the cultures (FIGS. 24B and C). Thus, sensitivity to GALC expression is a unique feature of HSPC, which was not observed in mature hematopoietic cells.

miR-126 Regulation Rescues HSPC from GALC Expression Toxicity and Enables Gene Therapy of GLD The selective toxicity of de novo GALC expression in HSPC highlights the need to tightly regulate transgene expression in HSPC for successful gene therapy of GLD. We thus tested the efficacy of our novel miR-126 based regulatory system and compared it to a transcriptional strategy based on the myeloid-specific CD11b promoter to target GALC expression to the differentiated HSPC progeny. Both strategies rescued the transduced HSPC from GALC-induced toxicity (see FIG. 23B-E). However, the reconstituted GALC activity was substantially higher (up to 2 fold the wild type level) in the progeny of the cells transduced with GALC-126T lentivector (in which GALC expression is driven by the PGK promoter) than in CD11b-GALC transduced cells, even when cultures transduced to similar vector copy number were compared (FIGS. 23B and C). We also verified that the GALC.126T lentiviral vector effectively protected human HSPC from GALC toxicity (FIGS. 23C and D). Given the likely benefit from supra-physiological enzyme activity in mature hematopoietic cells, we selected the mIRNA-regulated vector for in vivo studies of GLD therapy.

HSPC from Trs mice were transduced with the GALC-126T lentiviral vector and transplanted into newborn Trs mice. The transplanted mice were successfully engrafted (FIG. 24A) and showed a significantly longer survival not only with respect to the untreated Trs mice (p<0.0001), but also to the mice transplanted with wild type GFP-transduced HSPC (p=0.002; FIGS. 24A and D). Moreover, when we stratified gene therapy treated mice according to vector copy number measured in the BM, animals with the highest vector content showed a significantly longer survival (FIG. 6E), strongly suggesting that supra-physiological enzyme expression in hematopoietic cells augments the therapeutic efficacy of HSC transplantation. Indeed, effective delivery of the functional GALC enzyme to the affected brain and reconstitution of the defective activity were observed in the brain of gene therapy treated Trs mice (FIG. 24F-I). In the central nervous system of treated mice, GALC activity was detected both within Ibal$^+$, CD45$^+$ infiltrating hematopoietic cells, and within Ibal$^-$, CD45$^-$ non-hematopoietic cells (FIG. 24F-I), demonstrating cross-correction of resident cells likely due to enzyme secretion by the progeny of the transplanted and transduced HSPC. Importantly, reconstitution of enzymatic activity and increased survival were associated to a significantly ameliorated phenotype of the treated mice as compared to untreated affected controls, with preserved walking abilities and reduced twitching (GLD-associated intentional tremors).

DISCUSSION

Deep Profiling of miRNA Expression in the Hematopoietic System

The miRNA reporter vectors used in this work offer the opportunity to measure miRNA bioactivity rather than relying only on miRNA expression levels, thus providing a biologically meaningful, quantitative readout of miRNA function. Brown et al. have proposed that a threshold level of miRNA expression must be reached for significant suppressive activity against miRNA targets to occur, which might be the result of a limiting RNAi machinery available within a cell (Brown et al., 2007). If small RNAs compete for limited RNAi effector complexes, a sufficiently high level of expression may be necessary to ensure incorporation of the miRNA into an active RISC. Thus, those miRNA species, which are expressed to very low levels, may have little to no activity because they are not part of a functioning RISC. miRNA profiling studies often consider only relative differences in miRNA expression and can thus indicate statistically significant differences which may be, however, irrelevant to gene regulation. Combining the breadth of genome-wide miRNA expression analysis (e.g. by microarrays or deep sequencing) with the miRNA reporter Bd.LV approach adds another dimension to the study of microRNAs. It allows to stringently validate the biological significance of differential miRNA expression and can be used to longitudinally study the expression of a selected miRNA across multiple cell populations, with single cell resolution and in living cells. We used this approach to study the expression of selected miRNAs in rare and poorly accessible cell populations like HSC. Our miRNA reporter vector studies not only confirmed data on miR-223 and miR-126 expression profiles described in the literature, but added further information on the activity of these miRNA in highly pure HSPC subpopulations and their progeny. miR-223 has previously been described to be abundantly expressed in the myeloid lineage of mice and humans (Chen et al., 2004; Fazi et al., 2005; Rosa et al., 2007). Indeed, our reporter vector data found the highest miR-223 activity in granulocytes. Moreover, miR-223 activity was also revealed in monocytes and in a hierarchy of HSPC, in particular progenitors committed to the granulocyte-monocyte lineage. Our data suggest that at least some pluripotent hematopoietic cells express miR-223, in both mice and humans. One possibility is that these cells are primed for a granulocyte-monocyte fate. Our bidirectional reporter vectors allow fractionating these HSPC populations according to miR-223 expression and probe their differentiation potential. These studies may provide a novel way to prospectively identify myeloid progenitors relying not only on surface markers, and possibly investigate the earliest steps of lineage commitment.

The expression of miR-126 in the hematopoietic system was poorly characterized until now. A broad, deep-sequencing based, miRNA profiling study broadly assigned it to CD34$^+$ HSPC. We now show that miR-126 is active in murine and human HSPC, and in particular within subsets enriched for the most primitive HSC. During early steps of differentiation, miR-126 activity progressively decreases. The association of miR-126 to human HSC is further corroborated by an analysis of BdLV.126T-transduced CB HSPC freshly isolated from NOD/SCID mice performed by our collaborator at UHN, Toronto (Lechman et al., 2008, ASH Abstract). Our data support a stem/early progenitor-specific expression pattern for miR-126, with silencing in most downstream lineages.

Interestingly, a subgroup of acute myelogenous leukemia (AML) characterized by mutations in the "core-binding factor" (CBF) expresses high levels of miR-126 121. The authors identified polo-like kinase (PLK-2 as a validated target of miR-126. PLK-2 has been recognized as a regulator of the cell cycle and might act as a tumor suppressor gene in hematologic malignancies. Given the tight association of miR-126 with HSC, we are studying, in collaboration with the group of John Dick at UHN, Toronto, the activity of miR-126 in leukemic stem cells (LSC), a rare subpopulation standing at the apex of the developmental hierarchy of AML, which is thought to be responsible for chemotherapy resistance and relapse (Barabe et al., 2007; Kennedy et al., 2007). Preliminary results suggest that AML samples, in particular those belonging to other subgroups than CBF-AML, manifest a gradient of miR-126 expression, being highest in the LSC-enriched CD34$^+$38$^-$ fraction and low in non-engrafting fractions. This pattern of miR-126 activity is maintained upon transplantation of LSC into immunodeficient NOD/SCID mice. Thus, miR-126 activity, visualized by a lentiviral reporter Bd.LV, could serve as a new biomarker and potentially therapeutic target for leukemic AML stem cells (Lechman et al., 2008, ASH Abstract).

Outside the hematopoietic system, miR-126 has been extensively described as a positive regulator of angiogenic signaling in endothelial cells. Angiogenesis describes the formation of new blood vessels through the growth of pre-existing vessels. Signals promoting angiogenesis include vascular endothelial growth factor (VEGF) and basic fibroblast growth factor (bFGF), which activate mitogen-activated protein kinase (MAPK) and phosphoinositide 3-kinase (PI3K) cascades, regulating motility and proliferation of endothelial cells and consequent vessel sprouting. miR-126 has two validated targets involved in the angiogenic process, Sprouty-related EVH1 domain containing protein (Spred1) and a regulatory subunit of PI3K, both negative regulators of VEFG/FGF signalling. Endothelial cells lacking miR-126 fail to respond to angiogenetic signals. Knockdown of miR-126 in zebrafish resulted in loss of vascular integrity and haemorrhage during embryonic development (Fish et al., 2008), while deletion of miR-126 in mice causes leaky vessels, haemorrhaging, and partial embryonic lethality, due to a loss of vascular integrity and defects in endothelial cell proliferation, migration, and angiogenesis (Wang et al., 2008).

In summary, miR-126 is expressed to biologically relevant levels in angiogenic endothelial cells as well as hematopoietic stem cells and their immediate progeny. Interestingly, expression of miR-126 is another factor that endothelial cells and HSC have in common. In fact, during embryonic development, the simultaneous appearance of endothelial and hematopoietic cells (red blood cells) in the yolk sac, and the successive emergence of HSC and endothelial cells in the aorta-gonado-mesonephros region (AGM) underline the common origin of these 2 lineages, arising from a so-called "hemangioblast" cell population. No surprisingly, there is a growing list of genes, originally thought to be exclusively expressed in vascular endothelium, that have turned up in HSC and transcription factors and membrane receptors such as the Tie2 receptor, Sca-1, VEGFR-(Flt-1), VEGFR-(Flk-1) and CD31.

Given the functional and anatomical association between microvasculature and HSC through development and in the adult bone marrow, miR-126 may contribute to the homeostasis of the hematopoietic niche and regulate proliferation of both its endothelial and HSC components.

Interference of miRNA-Regulated LV with miRNA Function

One concern about exploiting miRNA regulation is the possibility to interfere with the regulation of natural miRNA targets by over-expressing transcripts containing miRNA target sequences. In order to understand the biology and safety of microRNA-regulated LV, we quantified the dose requirement for saturating an miRNA's activity (Gentner et al., 2009). Measuring the loss of regulation of sensitive reporters and a natural miRNA target upon challenging the cells with increasing doses of transcripts containing miRNA target sequences, we found that the threshold for interfering with physiological miRNA regulation is generally high and can only be reached when driving expression from strong, viral promoters. miRNA target sequences expressed from a moderate promoter like the phosphoglycerate kinase (PGK) promoter did not saturate miRNA activity, even at high vector copy number (up to 50 integrations). This suggested that miRNA regulation could safely be exploited for HSC gene therapy when expressing the miRNA regulated transcript from a moderate promoter and from a limited number of integrations per cell. However, we found that lentiviral vectors can be engineered for deliberately interfering with miRNA activity and thus be used as a tool to characterize miRNA function.

When over-expressing miRNA target sequences from strong promoters, we demonstrated that miRNA activity could be saturated, resulting in the loss of regulation of natural targets for that miRNA 126. Furthermore, we found that saturation could be favored by changing the design of our target sequences. For our gene-regulated vectors, such as the one described in this thesis, we exploited perfectly complementary miRNA binding sites which primarily result in degradation of the mRNA transcript (see FIG. 2c), similar to the mode of action of siRNA (Brown et al., 2007). As this process is occurring with fast kinetics (Haley et al., 2004), the miRNA-RISC complex actually works like an enzyme with high turnover rate, making it inherently difficult to be saturated. On the other hand, when introducing a mismatch between nucleotide 9 and 11 of the miRNA into the miRNA target sequence, transcript degradation is impaired 57, redirecting the miRISC/mRNA complex to the "translational repression" pathway which is also primarily used by natural miRNAs in animal cells. Since translational repression likely occurs at a slower rate than degradation, we showed that imperfect targets resulted more efficient in competitively blocking miRNA activity respect to perfectly complementary targets (Gentner et al., 2009). Importantly, lentiviral vector-based technology allows stable integration of such expression cassettes designed for miRNA knockdown into the genome, thus representing a platform, which allows stable interference with miRNA activity. We successfully exploited this technology to obtain a stable knockdown of miR-223. Transplanting mice with BM cells transduced with a miR-223 knockdown vector to high vector copy number resulted in an expansion of myeloid cells, suggesting that miR-223 acts on granulocyte monocyte precursors as a negative regulator of myelopoiesis. Furthermore, we found inflammatory lung pathology in mice which were reconstituted with BM containing the miR-223 knockdown vector, suggesting additional functions of miR-223 in the regulation of inflammatory myeloid cells (Gentner et al., 2009). Strikingly, these mice phenocopied a recently described miR-223 knockout mouse line (Johnnidis et al., 2008). Apart from genetic knockouts, miRNA loss-of-function studies were limited up to now to transient transfection of chemically modified miRNA antisense molecules called "antagomirs" (Krutzfeldt et al., 2005). While effective, their use is limited to cells, which can easily be transfected, which is not the case for most primary cells. Furthermore, the knockdown is transient and thus not easily applicable to genetic model systems. We envision broad applications for LV mediating stable miRNA knockdown. They will constitute important tools to investigate the physiological role of miRNA.

Applications of microRNA-Regulated Vectors for Hematopoietic Stem Cell Gene Therapy The pattern of reporter gene expression that we describe in this work has also relevant implications for gene therapy. Most clinical gene therapy constructs contain ubiquitously expressing promoters which guarantee robust expression of the transgene in the target cell types, but also result in off-target expression. This ectopic expression can result in toxicity, counterselection of gene-modified cells, triggering of an immune response directed against the transgene product, or even oncogenic transformation (Weil et al., 1997; Ott et al., 2006; Brown et al., 2006; Brown et al., 2007; Woods et al., 2006).

Adding miR-223 target sequences to a therapeutic transgene delivered to HSC would prevent expression in the myeloid progeny, including granulocyte monocyte progenitors and at least a subfraction of HSC. Importantly, this strategy would result in full therapeutic expression in the lymphoid and red cell lineage.

The identification of miR-126, which is strongly expressed in HSPC but not in differentiated progeny of the myeloid and lymphoid lineage, allows preventing expression of a potentially toxic transgene in sensitive stem cell populations, while maintaining expression and therapeutic efficacy in the diseased progeny.

Toxicity of GALC De Novo Expression

Enzyme replacement and gene therapy applications in LSD patients (Rohrbach et al., 2007; Brady et al., 2004) and animal models (Biffi et al., 2006; Sano et al., 2005; Hofling et al., 2004; Sands et al., 1997) have generally demonstrated the lack of toxicity of lysosomal enzyme administration and expression above normal levels. In the case of Metachromatic Leukodystrophy (MLD), the safety of LV-mediated over-expression of ARSA, catalyzing the step upstream of GALC in sulfatide metabolism, was demonstrated in mHSPC, hHSPC, and transgenic mice (Biffi et al., 2004; Capontondo et al., 2007), prompting clinical testing of HSPC gene therapy for this disease. Here, we report the unexpected finding of overt toxicity and in vitro and in vivo functional impairment of murine and human HSPC after LV-mediated GALC gene transfer and expression. GALC.LV transduced murine HSPC showed impaired clonogenic potential and failed to engraft and long-term repopulate myeloablated transplant recipients. This was associated to negative selection and and apoptosis of highly transduced HSPC. The lack of apoptosis and functional impairment observed in murine and human HSPC, transduced with a control vector in which GALC expression is regulated by the microRNA (Mechtcheriakova et al; 2007) (exclusively expressed in hematopoietic lineage cells) ((Brown et al., 2006), confirmed the unique role of expressed GALC in determining the death of transduced cells.

Differentiated Cells are Less Sensitive to GALC-Related Toxicity

We noticed that differentiated cells of the hematopoietic lineage (lymphocytes, monocytes, macrophages and microglia) and cells from other lineages (oligodendrocytes, as well as neural progenitors) (Gritti et al., personal communication), are not affected by LV-mediated GALC over-expression. Therefore, HSPC appear to have a unique sensitivity to GALC- and sphingolipid-mediated control of cell survival, which is apparently lost during differentiation into mature myeloid, T and B cells, and which is restricted to the hematopoietic lineage. A possible explanation for this, might be the very low basal GALC activity detected in HSPC, compared to other cell types, such as microglia or oligodendrocytes. Moreover, the role of sphingolipid metabolism and the consequences of an alteration in the content of Cer and derived molecules such as So and S1P, might vary according to cell types and differentiation stages. For example, the effect of intracellular Cer accumulation in oligodendrocytes was studied in depth, with conflicting findings. A recent study reported that induction of acid sphingomyelinase, which is responsible for Cer production from sphingomyelin degradation, resulted in Cer accumulation and induction of apoptosis (Chudakova et al., 2008). The same pathway seems to be involved in oligodendrocytic cell death induced by oxidative stress or by amyloid-beta peptide accumulation in Alzheimer's disease (Jana et al., 2007; Lee et al., 2004). However, mature oligodendrocytes were also described as being resistant to some pro-apoptotic stimuli, inducing Cer accumulation. Similarly, a differential response to pro-apoptotic TNF-stimulation was observed in oligodendrocytic precursors, where a high level of apoptosis was observed and in mature oligodendrocytes, which appeared to be resistant to apoptotic stimulation (Scurlock et al., 1999). Mature oligodendrocytes are also resistant to apoptosis induced by IL-1 administration (Brogi et al., 1997). This suggests that the increase of intracellular Cer could be managed in different ways, according to the pathways activated in that particular cell type and at that particular differentiation stage. Supporting this hypothesis, it has been reported that the increase of intracellular Cer in neural tissue, is managed by the high activity of acid ceramidase (Huang et al., 2004). This enzyme catalyzes the degradation of Cer to So, which, in turn, is phosphorylated to S1P. S1 P rescues cells from Cer-induced apoptosis (Betito et al., 2006) and induces proliferation in neural progenitor cells (Harada et al., 2004). It could be hypothesized that a similar mechanism was responsible for the reduced sensitivity of oligodendrocytes to GALC over-expression-related apoptosis. The sphingolipid metabolic pathway is also very active in oligodendrocytes, which are involved in myelination in order to produce the myelin glycosphingolipids (GalCer and Sulfatide). Moreover, these molecules participate in carbohydrate-carbohydrate interactions, forming glycosynapses (for a review see (Boggs et al., 2008).

The reduced sensitivity to GALC de novo expression-induced apoptosis observed in monocytes and macrophages might be explained both by the activity of ceramidase and their secretory action. Reports show that in endothelial cells and cells of the immune system, Cer is rapidly converted to So and S1P, which are secreted. In the plasma, these molecules bind albumin and act as signals for specific receptors on lymphocytes (for a review see 78 142 143Hannun et al., 2008; Mechtcheriakova et al., 2007; Rivera et al., 2008).

Post-Transcriptional Regulation of GALC Expression for Safe and Efficacious GLD Gene Therapy The regulation of transgene expression is of great interest in the field of gene therapy. In particular, the possibility of post-transcriptional regulation by micro RNA (miRNA), has recently open new perspectives for tuning the expression level of the transgene, according to cell type and to differentiation (Gentner et al., 2008). In this study, we applied this innovative technology in order to suppress GALC expression in HSPC, which have been shown to be the most sensitive cells to GALC over-expression toxicity, while allowing enzyme over-expression in differentiated cells, which are responsible for GALC secretion and cross correction of oligodendrocytes. In particular, we selected the microRNA126, which was reported to be more highly expressed in HSPC, as compared to peripheral blood mononuclear cells 145. Our data demonstrated that the regulation of GALC expression by the HSC-specific miRNA126, protects HSPC from GALC de novo-induced apoptosis in vitro and Transduction of GALC −/− HSPC with GALC.miR126T.LV permitted the reconstitution of enzymatic activity in their differentiated progeny at supra-physiological levels, without impairing the clonogenic potential of the multipotent progenitors, as assessed by the CFC assay. This data confirmed that miRNA126 suppresses GALC expression only in HSPC and not in their differentiated progeny. The unaffected clonogenic potential may indicate that GALC expression is repressed not only in HSC, but also in multipotent progenitors responsible for the formation of the hematopoietic colonies in CFC assay.

Moreover, transplantation of GALC.miR126T.LV-transduced HSPC into GALC +/− FVB/twi mice, resulted in long-term survival of treated animals. This data demonstrates that the suppression of GALC activity in the more primitive HSC by miRNA126, allows their long-term repopulation and differentiation potential, to be preserved. The presence of highly transduced cells in the BM ten weeks after HSCT, further confirmed that long-term HSC were rescued from GALC over-expression apoptosis.

Importantly, the post-transcriptional regulation by HSC-specific miRNA, permitted the use of a strong promoter, such as PGK, thereby reaching the same expression level of the transgene in the differentiated HSPC progeny, as that obtained with unregulated PGK GALC.LV. As discussed above, the level of GALC expression required for HSC gene therapy to be effective, is not known. However, even if a low enzyme expression level might be sufficient to obtain a clinical benefit, the use of a stronger promoter may allow the vector copy number(s) to be reduced, but reach the desired enzymatic expression. This issue could be relevant for the safety of clinical translation of HSC gene therapy.

CONCLUSIONS

The lentiviral vector platform represents a versatile and highly useful tool to study microRNA function. The bidirectional miRNA reporter vectors developed allow measuring miRNA activity at the single cell level in complex cell mixtures, adding a new dimension to conventional miRNA expression profiling approaches. Using this approach, we dissect the expression of several miRNAs in hematopoietic stem and progenitor cell (HSPC) populations with unprecedented resolution. Changing promoter and miRNA target design can result in lentiviral vectors capable of accomplishing stable miRNA knockdown, useful for generating loss-of-function phenotypes as a basis to elaborate the physiologic role of an miRNA. Proteomic analysis after stable miRNA knockdown will allow the identification of key targets for that miRNA that are modulated in the natural setting.

Besides addressing these basic biology questions, miRNA-regulated vectors have significant therapeutic potential. Added to the 3'UTR of a therapeutic transgene, miRNA target sequences can reduce ectopic transgene expression and thus alleviate or avoid transgene toxicity. In particular, hematopoietic stem cell (HSC) biology must not be disturbed by the gene therapy treatment, as HSC represent the guarantor for long-term disease correction by continuously supplying gene-modified daughter cells. The miRNAs characterized here, miR-126, miR-130a and miR-223 restrict unwanted transgene expression in HSPC, while allowing it in the differentiated progeny, and will be further developed into clinical gene therapy protocols.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

REFERENCES

Abonour R, Williams D A, Einhorn L, et al. Efficient retrovirus-mediated transfer of the multidrug resistance 1 gene into autologous human long-term rep opulating hematopoietic stem cells. Nat Med. 2000; 6:652-658.

Akashi K, Traver D, Miyamoto T, Weissman I L. A clonogenic common myeloid progenitor that gives rise to all myeloid lineages. Nature. 2000; 404:193-197.

Amendola, M., Venneri, M. A., Biffi, A., Vigna, E. & Naldini, L. Coordinate dual-gene transgenesis by lentiviral vectors carrying synthetic bidirectional promoters. Nature biotechnology 23, 108-116 (2005).

Armstrong R C. Isolation and characterization of immature oligodendrocyte lineage cells. Methods 1998; 16:282-292.

Barabe F, Kennedy J A, Hope K J, Dick J E. Modeling the initiation and progression of human acute leukemia in mice. Science. 2007; 316:600-604.

Bartel D P. MicroRNAs: genomics, biogenesis, mechanism, and function. Cell. 2004; 116:281-297.

Bartel D P. MicroRNAs: target recognition and regulatory functions. Cell. 2009; 136:215-233.

Betito S, Cuvillier O. Regulation by sphingosine 1-phosphate of Bax and Bad activities during apoptosis in a MEK-dependent manner. Biochem Biophys Res Commun. 2006; 340:1273-1277.

Biffi A, Capotondo A, Fasano S, et al. Gene therapy of metachromatic leukodystrophy reverses neurological damage and deficits in mice. J Clin Invest. 2006; 116: 3070-3082.

Biffi A, De Palma M, Quattrini A, et al. Correction of metachromatic leukodystrophy in the mouse model by transplantation of genetically modified hematopoietic stem cells. J Clin Invest. 2004; 113:1118-1129.

Biffi A, De Palma M, Quattrini A, et al. Correction of Metachromatic Leukodystrophy in the Mouse Model by Transplantation of Genetically Modified Hematopoietic Stem Cells. J Clin Invest. 2004; 113:1118-1129.

Boggs J M, Gao W, Hirahara Y. Myelin glycosphingolipids, galactosylceramide and sulfatide, participate in carbohydrate-carbohydrate interactions between apposed membranes and may form glycosynapses between oligodendrocyte and/or myelin membranes. Biochim Biophys Acta. 2008; 1780:445-455.

Brady R O, Schiffmann R. Enzyme-replacement therapy for metabolic storage disorders. Lancet Neurol. 2004; 3:752-756.

Brady R O. Enzyme replacement for lysosomal diseases. Annu Rev Med. 2006; 57:283-296.

Brennecke J, Stark A, Russell R B, Cohen S M. Principles of microRNA-target recognition. PLoS Biol. 2005; 3:e85.

Brogi A, Strazza M, Melli M, Costantino-Ceccarini E. Induction of intracellular ceramide by interleukin-1 beta in oligodendrocytes. J Cell Biochem. 1997; 66:532-541.

Brown B D, Cantore A, Annoni A, et al. A microRNA-regulated lentiviral vector mediates stable correction of hemophilia B mice. Blood. 2007; 110:4144-4152.

Brown B D, Gentner B, Cantore A, et al. Endogenous microRNA can be broadly exploited to regulate transgene expression according to tissue, lineage and differentiation state. Nat Biotechnol. 2007; 25:1457-1467.

Brown B D, Venneri M A, Zingale A, Sergi Sergi L, Naldini L. Endogenous microRNA regulation suppresses transgene expression in hematopoietic lineages and enables stable gene transfer. Nat Med. 2006; 12:585-591.

Capotondo A, Cesani M, Pepe S, et al. Safety of Arylsulfatase A Overexpression for Gene Therapy of Metachromatic Leukodystrophy. Hum Gene Ther. 2007; [Epub ahead of print] PMID: 17845130.

Chen C Z, Li L, Lodish H F, Bartel D P. MicroRNAs modulate hematopoietic lineage differentiation. Science. 2004; 303:83-86.

Chudakova D A, Zeidan Y H, Wheeler B W, et al. Integrin-associated Lyn kinase promotes cell survival by suppressing acid sphingomyelinase activity. J Biol Chem. 2008; 283:28806-28816.

Divaka ran V, Mann D L. The emerging role of microRNAs in cardiac remodeling and heart failure. Circ Res. 2008; 103:1072-1083.

Fazi F, Rosa A, Fatica A, et al. A minicircuitry comprised of microRNA-223 and transcription factors NH-A and C/EBPalpha regulates human granulopoiesis. Cell. 2005; 123:819-831.

Fish J E, Santoro M M, Morton S U, et al. miR-126 regulates angiogenic signaling and vascular integrity. Dev Cell. 2008; 15:272-284.

Gaziev J, Lucarelli G. Stem cell transplantation and gene therapy for hemoglobinopathies. Curr Hematol Rep. 2005; 4:126-131.

Gentner B, Schira G, Giustacchini A, et al. Stable knockdown of microRNA in vivo by lentiviral vectors. Nat Methods. 2009; 6:63-66.

Gentner B, Schira G, Giustacchini A, et al. Stable knockdown of microRNA in vivo by lentiviral vectors. Nat Methods. 2008.

Gritti A, Parati E A, Cova L, et al. Multipotential stem cells from the adult mouse brain proliferate and self-renew in response to basic fibroblast growth factor. J Neurosci. 1996; 16:1091-1100.

Haley B, Zamore P D. Kinetic analysis of the RNAi enzyme complex. Nat Struct Mol Biol. 2004; 11:599-606.

Harada J, Foley M, Moskowitz M A, Waeber C. Sphingosine-1-phosphate induces proliferation and morphological changes of neural progenitor cells. J Neurochem. 2004; 88:1026-1039.

He L, He X, Lowe S W, Hannon G J. microRNAs join the p53 network—another piece in the tumour-suppression puzzle. Nat Rev Cancer. 2007; 7:819-822.

Hofling A A, Devine S, Vogler C, Sands M S. Human CD34[+] hematopoietic progenitor cell-directed lentiviral-mediated gene therapy in a xenotransplantation model of lysosomal storage disease. Mol Ther. 2004; 9:856-865.

Huang Y, Tanimukai H, Liu F, Iqbal K, Grundke-Iqbal I, Gong C X. Elevation of the level and activity of acid ceramidase in Alzheimer's disease brain. Eur J Neurosci. 2004; 20:3489-3497.

Jana A, Pahan K. Oxidative stress kills human primary oligodendrocytes via neutral sphingomyelinase: implications for multiple sclerosis. J Neuroimmune Pharmacol. 2007; 2:184-193.

Johnidis J B, Harris M H, Wheeler R T, et al. Regulation of progenitor cell proliferation and granulocyte function by microRNA-223. Nature. 2008; 451:1125-1129.

Kennedy J A, Barabe F, Poeppl A G, Wang J C, Dick J E. Comment on "Tumor growth need not be driven by rare cancer stem cells". Science. 2007; 318:1722; author reply 1722.

Kiel M J, Yilmaz O H, Iwashita T, Terhorst C, Morrison S J. SLAM family receptors distinguish hematopoietic stem and progenitor cells and reveal endothelial niches for stem cells. Cell. 2005; 121:1109-1121.

Kitsera N, Khobta A, Epe B. Destabilized green fluorescent protein detects rapid removal of transcription blocks after genotoxic exposure. Biotechniques. 2007; 43:222-227.

Krutzfeldt J, Rajewsky N, Braich R, et al. Silencing of microRNAs in vivo with 'antagomirs'. Nature. 2005; 438:685-689.

Krutzfeldt J, Stoffel M. MicroRNAs: a new class of regulatory genes affecting metabolism. Cell Metab. 2006; 4:9-12.

Kuehbacher A, Urbich C, Zeiher A M, Dimmeler S. Role of Dicer and Drosha for endothelial microRNA expression and angiogenesis. Circ Res. 2007; 101:59-68.

Lagos-Quintana M, Rauhut R, Meyer J, Borkhardt A, Tuschl T. New microRNAs from mouse and human. RNA. 2003; 9:175-179.

Landgraf P, Rusu M, Sheridan R, et al. A mammalian microRNA expression atlas based on small RNA library sequencing. Cell. 2007; 129:1401-1414.

Lee J T, Xu J, Lee J M, et al. Amyloid-beta peptide induces oligodendrocyte death by activating the neutral sphingomyelinase-ceramide pathway. J Cell Biol. 2004; 164:123-131.

Lee R C, Feinbaum R L, Ambros V. The *C. elegans* heterochronic gene lin-4 encodes small RNAs with antisense complementarity to lin-14. Cell. 1993; 75:843-854.

Lund E, Guttinger S, Calado A, Dahl berg J E, Kutay U. Nuclear export of microRNA precursors. Science. 2004; 303:95-98.

Mechtcheriakova D, Wlachos A, Sobanov J, et al. Sphingosine 1-phosp hate phosphatase 2 is induced during inflammatory responses. Cell Signal. 2007; 19:748-760.

Mercer T R, Dinger M E, Mattick J S. Long non-coding RNAs: insights into functions. Nat Rev Genet. 2009; 10:155-159.

Naldini L, Blomer U, Gallay P, et al. In vivo gene delivery and stable transduction of nondividing cells by a lentiviral vector. Science. 1996; 272:263-267.

Ott M G, Schmidt M, Schwarzwaelder K, et al. Correction of X-linked chronic granulomatous disease by gene therapy, augmented by insertional activation of MDS1-EVI1, PRDM16 or SETBP1. Nat Med. 2006; 12:401-409.

Ott M G, Seger R, Stein S, Siler U, Hoelzer D, Grez M. Advances in the treatment of Chronic Granulomatous Disease by gene therapy. Curr Gene Ther. 2007; 7:155-161.

Pillai R S. MicroRNA function: multiple mechanisms for a tiny RNA? RNA. 2005; 11:1753-1761.

Pronk C J, Rossi D J, Mansson R, et al. Elucidation of the phenotypic, functional, and molecular topography of a myeloerythroid progenitor cell hierarchy. Cell Stem Cell. 2007; 1:428-442.

Reinhart B J, Slack F J, Basson M, et al. The 21-nucleotide let-7 RNA regulates developmental timing in *Caenorhabditis elegans*. Nature. 2000; 403:901-906.

Rivera J, Proia R L, Olivera A. The alliance of sphingosine-1-phosphate and its receptors in immunity. Nat Rev Immunol. 2008; 8:753-763.

Rohrbach M, Clarke J T. Treatment of lysosomal storage disorders: progress with enzyme replacement therapy. Drugs. 2007; 67:2697-2716.

Rohrbach M, Clarke J T. Treatment of lysosomal storage disorders: progress with enzyme replacement therapy. Drugs. 2007; 67:2697-2716.

Rosa A, Ballarino M, Sorrentino A, et al. The interplay between the master transcription factor PU.1 and miR- 424 regulates human monocyte/macrophage differentiation. Proc Natl Acad Sci USA. 2007; 104:19849-19854.

Sadelain M, Lisowski L, Samakoglu S, Rivella S, May C, Riviere I. Progress toward the genetic treatment of the beta-thalassemias. Ann N Y Acad Sci. 2005; 1054:78-91.

Sadelain M. Recent advances in globin gene transfer for the treatment of beta-thalassemia and sickle cell anemia. Curr Opin Hematol 2006; 13:142-148.

Sands M S, Vogler C, Torrey A, et al. Murine mucopolysaccharidosis type VII: long term therapeutic effects of enzyme replacement and enzyme replacement followed by bone marrow transplantation. J Clin Invest. 1997; 99:1596-1605.

Sano R, Tessitore A, Ingrassia A, d'Azzo A. Chemokine-induced recruitment of genetically modified bone marrow cells into the CNS of GM1-gangliosidosis mice corrects neuronal pathology. Blood. 2005; 106:2259-2268.

Schwarz D S, Hutvagner G, Du T, Xu Z, Aronin N, Zamore P D. Asymmetry in the assembly of the RNAi enzyme complex. Cell. 2003; 115:199-208.

Scurlock B, Dawson G. Differential responses of oligodendrocytes to tumor necrosis factor and other pro-apoptotic agents: role of ceramide in apoptosis. J Neurosci Res. 1999; 55:514-522.

Terstappen L W, Huang S, Safford M, Lansdorp P M, Loken M R. Sequential generations of hematopoietic colonies derived from single nonlineage-committed CD34$^+$ CD38$^-$ progenitor cells. Blood. 1991; 77:1218-1227.

Tomari Y, Zamore P D. Perspective: machines for RNAi. Genes Dev. 2005; 19:517-529.

Wang S, Aurora A B, Johnson B A, et al. The endothelial-specific microRNA miR-126 governs vascular integrity and angiogenesis. Dev Cell. 2008; 15:261-271.

Weil W M, Linton G F, Whiting-Theobald N, et al. Genetic correction of p67phox deficient chronic granulomatous disease using peripheral blood progenitor cells as a target for ret rovirus mediated gene transfer. Blood. 1997; 89:1754-1761.

Woods N B, Bottero V, Schmidt M, von Kalle C, Verma I M. Gene therapy: therapeutic gene causing lymphoma. Nature. 2006; 440:1123.

Wu Y P, Matsuda J, Kubota A, Suzuki K, Suzuki K. Infiltration of hematogenous lineage cells into the demyelinating central nervous system of twitcher mice. J Neuropathol Exp Neurol. 2000; 59:628-639.

Xiao C, Rajewsky K. MicroRNA control in the immune system: basic principles. Cell. 2009; 136:26-36.

Yeager A M, Brennan S, Tiffany C, Moser H W, Santos G W. Prolonged survival and remyelination after hematopoietic cell transplantation in the twitcher mouse. Science. 1984; 225:1052-1054.

Yeager A M, Shinn C, Shinohara M, Pardon D M. Hematopoietic cell transplantation in the twitcher mouse. The effects of pretransplant conditioning with graded doses of busulfan. Transplantation. 1993; 56:185-190.

Yesilipek M A. Stem cell transplantation in hemoglobinopathies. Hemoglobin. 2007; 31:251-256.

Yi R, Qin Y, Macara I G, Cullen B R. Exportin-5 mediates the nuclear export of pre-microRNAs and short hairpin RNAs. Genes Dev. 2003; 17:3011-3016.

The invention claimed is:

1. A method of regulating expression of a transgene comprising delivering a gene vector to a haematopoietic stem or progenitor cell, wherein the gene vector comprises at least one mir-126 and/or mir-130a target sequence operably linked to the transgene, wherein the transgene encodes interferon-alpha, lysosomal enzyme galactocerebrosidase or gp91 phox, and wherein expression of the transgene is prevented or reduced in the haematopoietic stem or progenitor cell but not in a differentiated cell.

2. The method of claim 1, wherein the gene vector comprises at least one mir-126 target sequence and at least one mir-130a target sequence.

3. The method of claim 2, wherein the gene vector comprises twice as many copies of the mir-130a target sequence as copies of the mir-126 target sequence.

4. The method of claim 1, wherein the gene vector is a viral vector.

5. The method of claim 1, wherein the gene vector is derivable from a lentivirus.

6. The method of claim 1, wherein the gene vector comprises a tissue-specific promoter.

7. The method of claim 6, wherein the tissue-specific promoter promotes expression in cells of the myeloid lineage.

8. The method of claim 6, wherein the tissue-specific promoter is selected from the group consisting of CD11 b, c-Fes, CYBB and TEK.

9. The method of claim 1, wherein the transgene encodes interferon-alpha, and wherein the gene vector comprises a TEK promoter operably linked to the transgene.

10. The method of claim 1, wherein the method is for increasing the chances of survival of the haematopoietic stem or progenitor cell in relation to gene therapy.

11. The method of claim 1, wherein the method is for preventing apoptosis of the haematopoietic stem or progenitor cell, whereby the apoptosis is caused by expression of the transgene.

12. The method of claim 1, wherein the method is for haematopoietic cell therapy.

* * * * *

```
                        SEQUENCE LISTING

<160> NUMBER OF SEQ ID NOS: 10

<210> SEQ ID NO 1
<211> LENGTH: 22
<212> TYPE: RNA
<213> ORGANISM: Artificial Sequence
<220> FEATURE:
<223> OTHER INFORMATION: miRNA sequence target

<400> SEQUENCE: 1
ucguaccgug aguaauaaug cg                                            22

<210> SEQ ID NO 2
<211> LENGTH: 98
<212> TYPE: DNA
<213> ORGANISM: Artificial Sequence
<220> FEATURE:
<223> OTHER INFORMATION: miR-126T sequence complementary to the miRNA

<400> SEQUENCE: 2
gcattattac tcacggtacg acgatgcatt attactcacg gtacgaacgc gtgcattatt    60
actcacggta cgatcacgca ttattactca cggtacga                           98

<210> SEQ ID NO 3
<211> LENGTH: 22
<212> TYPE: RNA
<213> ORGANISM: Artificial Sequence
<220> FEATURE:
<223> OTHER INFORMATION: miRNA sequence target

<400> SEQUENCE: 3
cagugcaaug uuaaaagggc au                                            22
```

```
<210> SEQ ID NO 4
<211> LENGTH: 106
<212> TYPE: DNA
<213> ORGANISM: Artificial Sequence
<220> FEATURE:
<223> OTHER INFORMATION: miR-130aT sequence complementary to the miRNA

<400> SEQUENCE: 4 atgcccttttt aacattgcac tgttcgaaat gcccttttaa cattgcactg acgcgtatgc    60
ccttttaaca ttgcactgat gcatatgccc ttttaacatt gcactg                   106

<210> SEQ ID NO 5
<211> LENGTH: 22
<212> TYPE: RNA
<213> ORGANISM: Artificial Sequence
<220> FEATURE:
<223> OTHER INFORMATION: miRNA sequence target

<400> SEQUENCE: 5
ugucaguuug ucaaauaccc ca                                              22

<210> SEQ ID NO 6
<211> LENGTH: 98
<212> TYPE: DNA
<213> ORGANISM: Artificial Sequence
<220> FEATURE:
<223> OTHER INFORMATION: miR-223T sequence complementary to the miRNA

<400> SEQUENCE: 6
ggggtatttg acaaactgac acgatgggt atttgacaaa ctgacaaccg gtggggtatt     60
tgacaaactg acatcacggg gtatttgaca aactgaca                            98

<210> SEQ ID NO 7
<211> LENGTH: 102
<212> TYPE: DNA
<213> ORGANISM: Artificial Sequence
<220> FEATURE:
<223> OTHER INFORMATION: 126T/130aT 2/2 combination sequence

<400> SEQUENCE: 7
gcattattac tcacggtacg acgatgcatt attactcacg gtacgaacgc gtatgcccttt   60 ttaacattgc actgatgcat atgcccttttt aacattgcac tg                      102

<210> SEQ ID NO 8
<211> LENGTH: 46
<212> TYPE: DNA
<213> ORGANISM: Artificial Sequence
<220> FEATURE:
<223> OTHER INFORMATION: 126T (2 targets)

<400> SEQUENCE: 8
gcattattac tcacggtacg acgatgcatt attactcacg gtacga                   46

<210> SEQ ID NO 9
<211> LENGTH: 155
<212> TYPE: DNA
<213> ORGANISM: Artificial Sequence
<220> FEATURE:
<223> OTHER INFORMATION: Triple combination target (126T/130aT/223T, 2
      targets each)

<400> SEQUENCE: 9
gcattattac tcacggtacg acgatgcatt attactcacg gtacgaacgc gtatgccctt    60
ttaacattgc actgatgcat atgcccttttt aacattgcac tgccccggtg gggtatttga  120
```

```
caaactgaca tcacggggta tttgacaaac tgaca                                    155

<210> SEQ ID NO 10
<211> LENGTH: 4
<212> TYPE: PRT
<213> ORGANISM: Artificial Sequence
<220> FEATURE:
<223> OTHER INFORMATION: Sequence motif

<400> SEQUENCE: 10

Pro Glu Ser Thr
1
```